(12) United States Patent
Bakos et al.

(10) Patent No.: US 11,134,952 B2
(45) Date of Patent: Oct. 5, 2021

(54) DUAL LEVER TO REDUCE FORCE TO FIRE IN CIRCULAR SURGICAL STAPLER

(71) Applicant: ETHICON LLC, Guaynabo, PR (US)

(72) Inventors: Gregory J. Bakos, Mason, OH (US); Disha V. Labhasetwar, Cincinnati, OH (US); Gregory G. Scott, Cincinnati, OH (US); Nicholas M. Morgan, West Chester, OH (US); Michael A. Jacobs, Villa Hills, KY (US); Michael J. Stokes, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 188 days.

(21) Appl. No.: 16/159,854

(22) Filed: Oct. 15, 2018

(65) Prior Publication Data

US 2020/0113567 A1 Apr. 16, 2020

(51) Int. Cl.
*A61B 17/115* (2006.01)
*A61B 90/00* (2016.01)
*A61B 17/00* (2006.01)

(52) U.S. Cl.
CPC .......... *A61B 17/1155* (2013.01); *A61B 90/08* (2016.02); *A61B 2017/00367* (2013.01); (Continued)

(58) Field of Classification Search
CPC ................. A61B 17/1155; A61B 90/08; A61B 2017/00367
See application file for complete search history.

(56) References Cited

U.S. PATENT DOCUMENTS

| 4,754,909 A | 7/1988 | Barker et al. |
| 5,205,459 A | 4/1993 | Brinkerhoff et al. |

(Continued)

FOREIGN PATENT DOCUMENTS

| CN | 100 463 659 C | 5/2007 |
| EP | 2 851 012 A1 | 3/2015 |

(Continued)

OTHER PUBLICATIONS

U.S. Appl. No. 16/159,848 entitled, "Latch to Prevent Back-Driving of Circular Surgical Stapler," filed Oct. 15, 2018.

(Continued)

*Primary Examiner* — Nathaniel C Chukwurah
*Assistant Examiner* — Lucas E. A. Palmer
(74) *Attorney, Agent, or Firm* — Frost Brown Todd LLC

(57) ABSTRACT

An apparatus includes a body assembly with a handle and a shaft portion, an end effector with a staple deck fixed to the shaft portion, an anvil, and a firing assembly. The end effector further includes a trocar and a staple driver both configured to actuate relative to the staple deck. The staple driver can actuate a distance between an unfired position and a fired position. The trocar can couple with the anvil to define a gap distance. The firing assembly includes a trigger pivotably coupled with the body assembly via a first pivot, a driver actuator configured to actuate the staple driver, and a linkage assembly pivotably coupled with the trigger via a second pivot and the driver actuator. Where the second pivot is proximal relative to the first pivot. The linkage assembly can drive the driver actuator is response to the trigger pivoting about the first pivot.

19 Claims, 36 Drawing Sheets

(52) U.S. Cl.
CPC ............... *A61B 2017/00477* (2013.01); *A61B 2090/0811* (2016.02)

(56) References Cited

U.S. PATENT DOCUMENTS

| | | | |
|---|---|---|---|
| 5,271,544 | A | 12/1993 | Fox et al. |
| 5,275,322 | A | 1/1994 | Brinkerhoff et al. |
| 5,285,945 | A | 2/1994 | Brinkerhoff et al. |
| 5,292,053 | A | 3/1994 | Bilotti et al. |
| 5,333,773 | A | 8/1994 | Main et al. |
| 5,350,104 | A | 9/1994 | Main et al. |
| 5,533,661 | A | 7/1996 | Main et al. |
| 6,269,997 | B1 | 8/2001 | Balazs et al. |
| 7,794,475 | B2 | 9/2010 | Hess et al. |
| 8,910,847 | B2 | 12/2014 | Nalagatla et al. |
| 9,289,207 | B2 | 3/2016 | Shelton, IV |
| 9,463,022 | B2 | 10/2016 | Swayze et al. |
| 9,498,222 | B2 | 11/2016 | Scheib et al. |
| 9,532,783 | B2 | 1/2017 | Swayze et al. |
| 9,572,573 | B2 | 2/2017 | Scheib et al. |
| 9,597,081 | B2 | 3/2017 | Swayze et al. |
| 9,724,100 | B2 | 8/2017 | Scheib et al. |
| 9,936,949 | B2 | 4/2018 | Measamer et al. |
| 2007/0295780 | A1* | 12/2007 | Shelton .................. A61B 17/32 227/176.1 |
| 2014/0158747 | A1 | 6/2014 | Measamer et al. |
| 2014/0166728 | A1* | 6/2014 | Swayze ............. A61B 17/1155 227/179.1 |
| 2014/0276736 | A1* | 9/2014 | Worrell ............. A61B 18/1445 606/33 |
| 2016/0374673 | A1* | 12/2016 | Stager .................. A61B 17/068 227/176.1 |
| 2016/0374684 | A1 | 12/2016 | DiNardo et al. |
| 2017/0238936 | A1* | 8/2017 | Mujawar ............ A61B 17/1285 |
| 2018/0008276 | A1* | 1/2018 | Bhatnagar ............ A61B 17/068 |
| 2019/0076210 | A1* | 3/2019 | Baril ...................... A61B 90/08 |
| 2019/0328389 | A1* | 10/2019 | Baril .................. A61B 17/1285 |
| 2020/0008806 | A1* | 1/2020 | Dinino ............... A61B 17/1285 |
| 2020/0046328 | A1* | 2/2020 | Zammataro ........... A61B 17/00 |
| 2020/0046362 | A1* | 2/2020 | Baril .................... A61B 17/128 |
| 2020/0046363 | A1* | 2/2020 | Baril .................... A61B 17/128 |

FOREIGN PATENT DOCUMENTS

| | | |
|---|---|---|
| EP | 2100561 B1 | 8/2018 |
| WO | WO 82/00968 A1 | 4/1982 |
| WO | WO 83/02247 A1 | 7/1983 |
| WO | WO 2005/037084 A2 | 4/2005 |
| WO | WO 2005/115254 A2 | 12/2005 |

OTHER PUBLICATIONS

U.S. Appl. No. 16/159,851 entitled, "Dual Stage Closure System for Circular Surgical Stapler," filed Oct. 15, 2018.
European Search Report, Partial, and Provisional Written Opinion dated Feb. 20, 2020 for Application No. EP 19202998.1, 15 pgs.
International Search Report and Written Opinion dated Feb. 28, 2020 for Application No. PCT/IB2019/058692, 21 pgs.

* cited by examiner

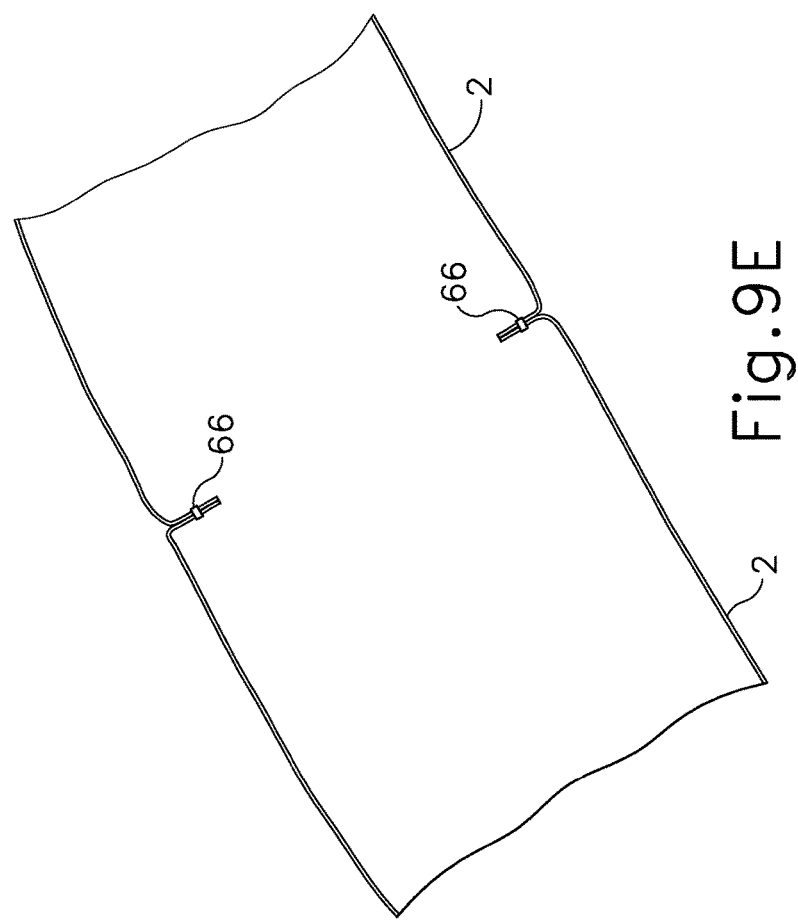
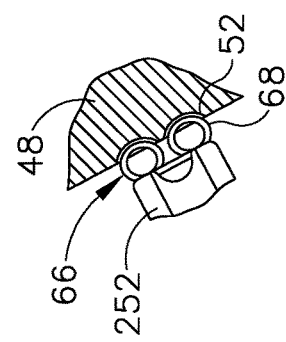

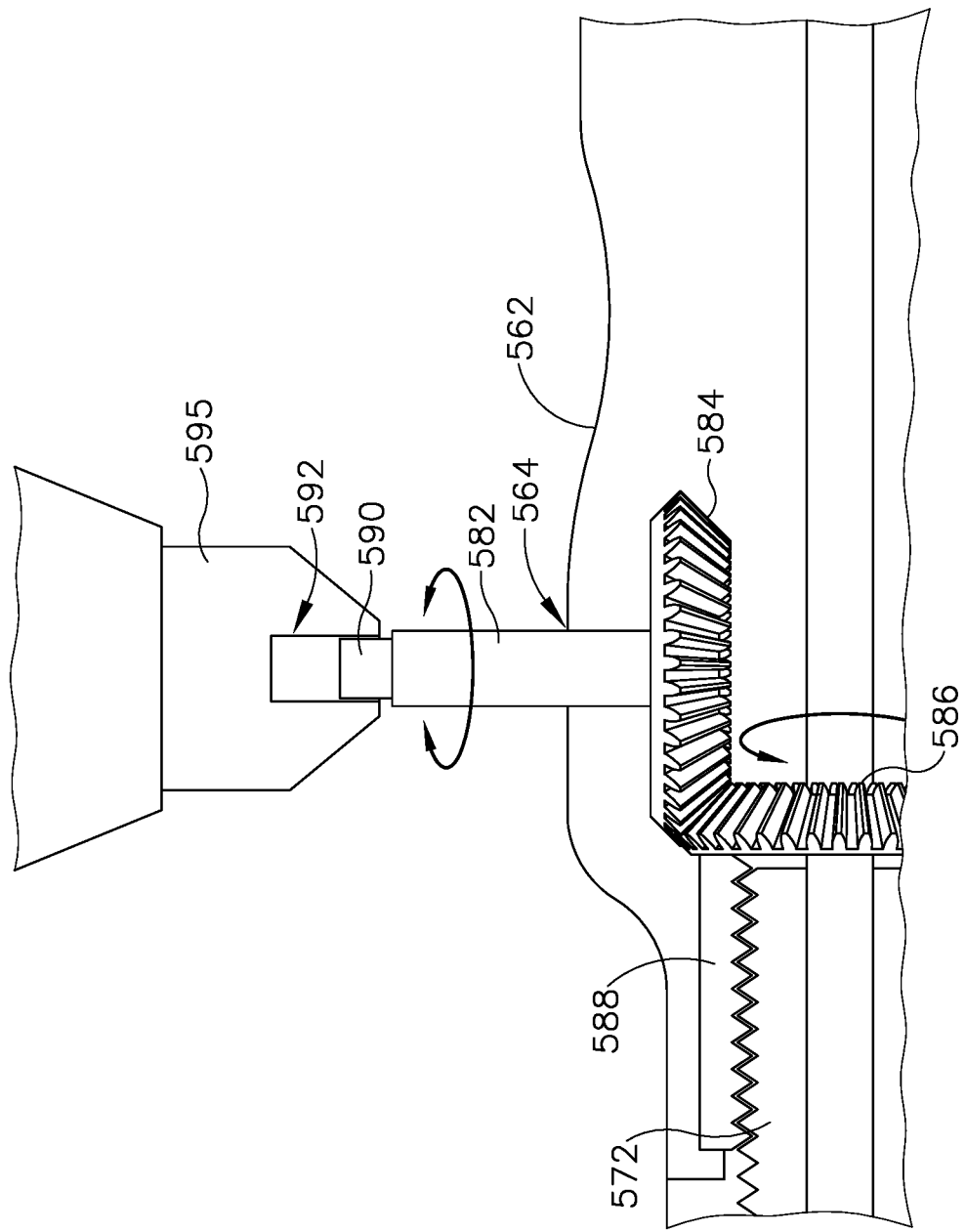

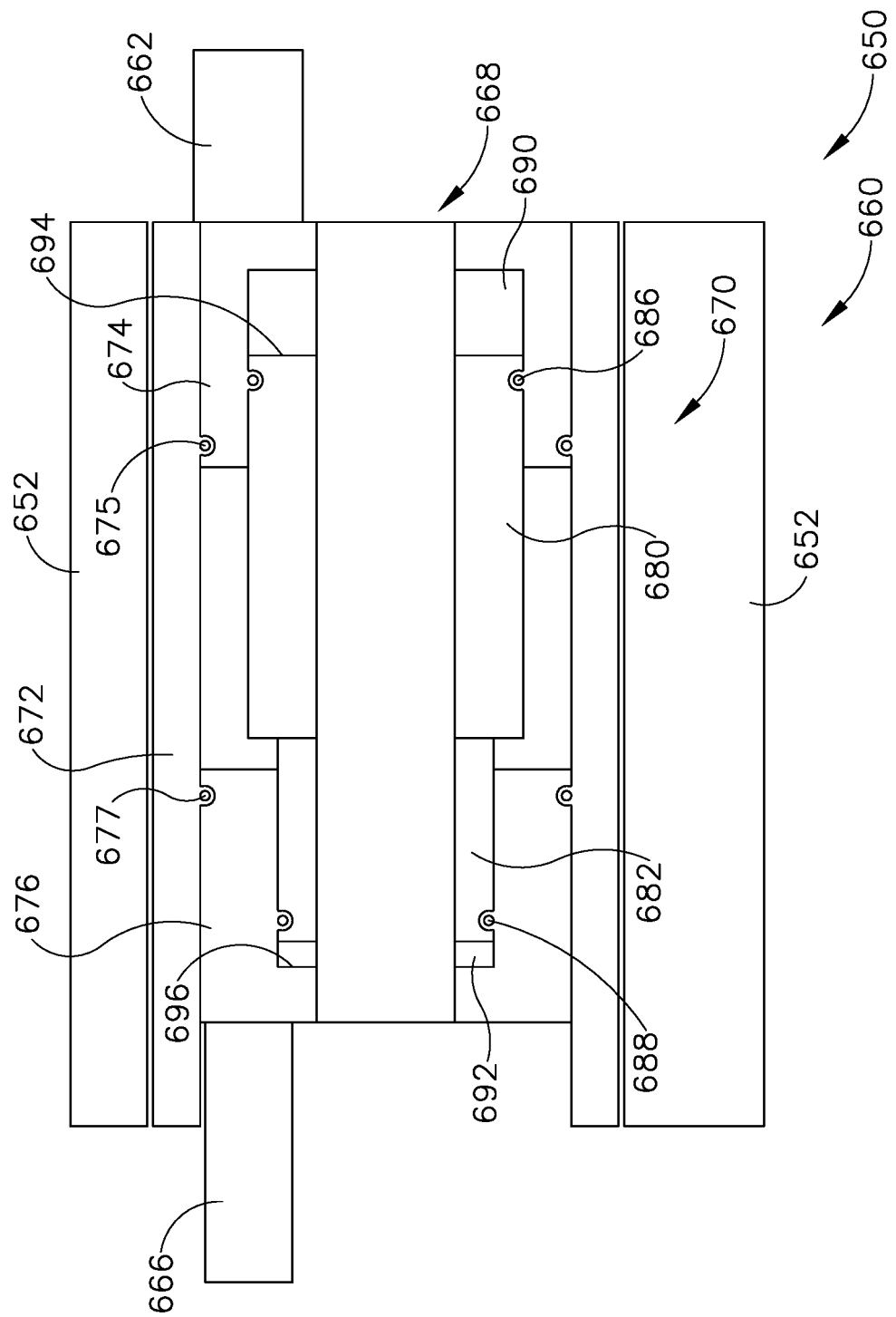

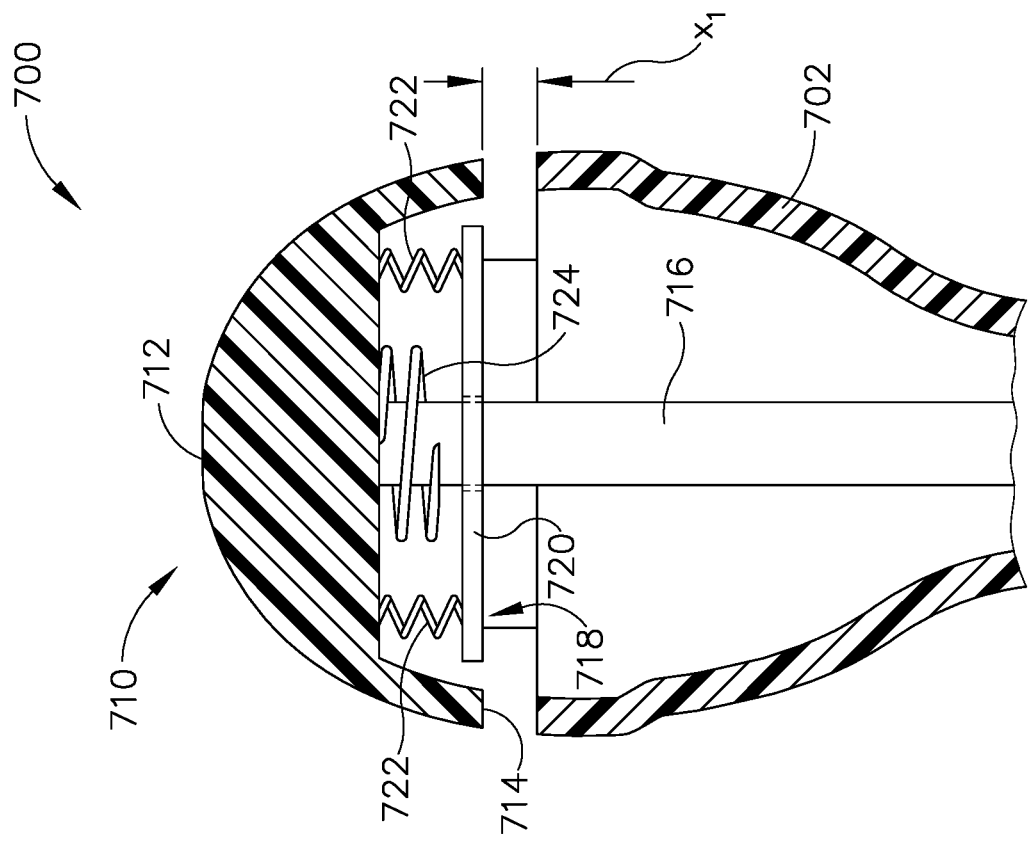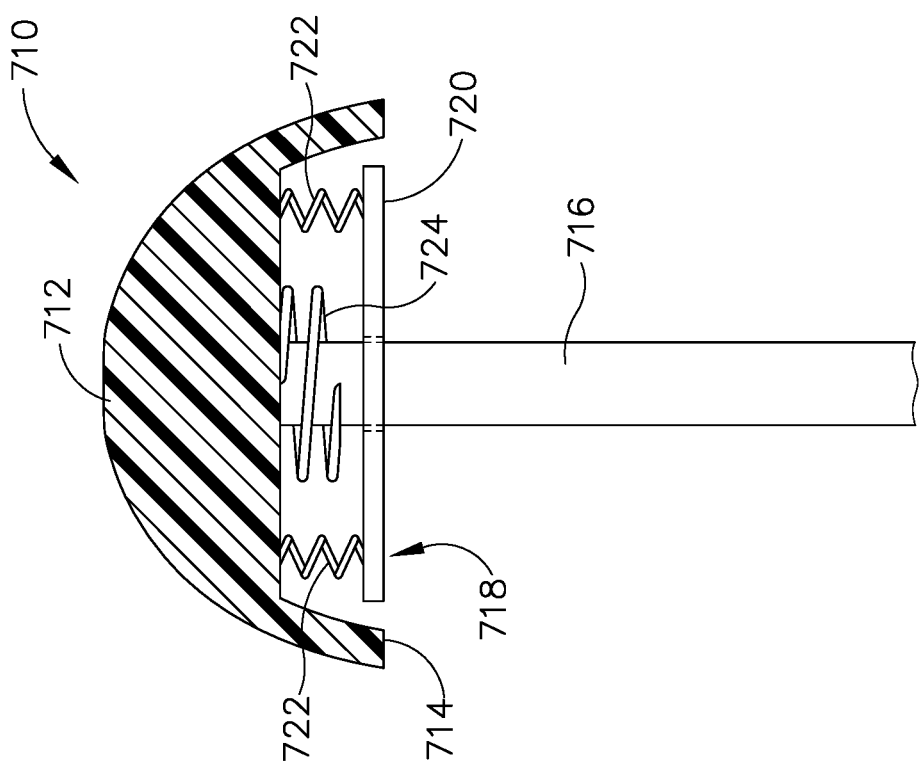

DUAL LEVER TO REDUCE FORCE TO FIRE IN CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9E depicts an enlarged longitudinal cross-section view of the first tubular portion and the second tubular portion after the stapling head assembly of FIG. 5 and the anvil of FIG. 2 have been removed, leaving a completed end-to-end anastomosis;

FIG. 10 depicts an enlarged partial cross-sectional view of an exemplary staple formed against the anvil of FIG. 2; assembly that may be readily incorporated into the surgical instrument of FIG. 1, with a portion of the body removed, showing a trigger in an unfired position and a lockout feature in a locked position;

FIG. 23 depicts a cross-sectional side view of the input shaft and the input bevel gear of the actuator handle assembly of FIG. 18 coupled with a motor driven rotating member;

FIG. 28 depicts a cross-sectional side view of an alternative actuator handle assembly that may be readily incorporated into the surgical instrument of FIG. 1;

FIG. 29 depicts a cross-sectional front view of an alternative anvil that may be readily incorporated into the surgical instrument of FIG. 1;

FIG. 30A depicts a cross-sectional front view of the anvil of FIG. 29 coupled with an alternative staple head assembly that may be readily incorporated into the surgical instrument of FIG. 1, where the staple head assembly has initially fired a plurality of staples against a proximal surface of the anvil such that the staples are initially forming, and the severing of tissue is incomplete;

Figure 1:
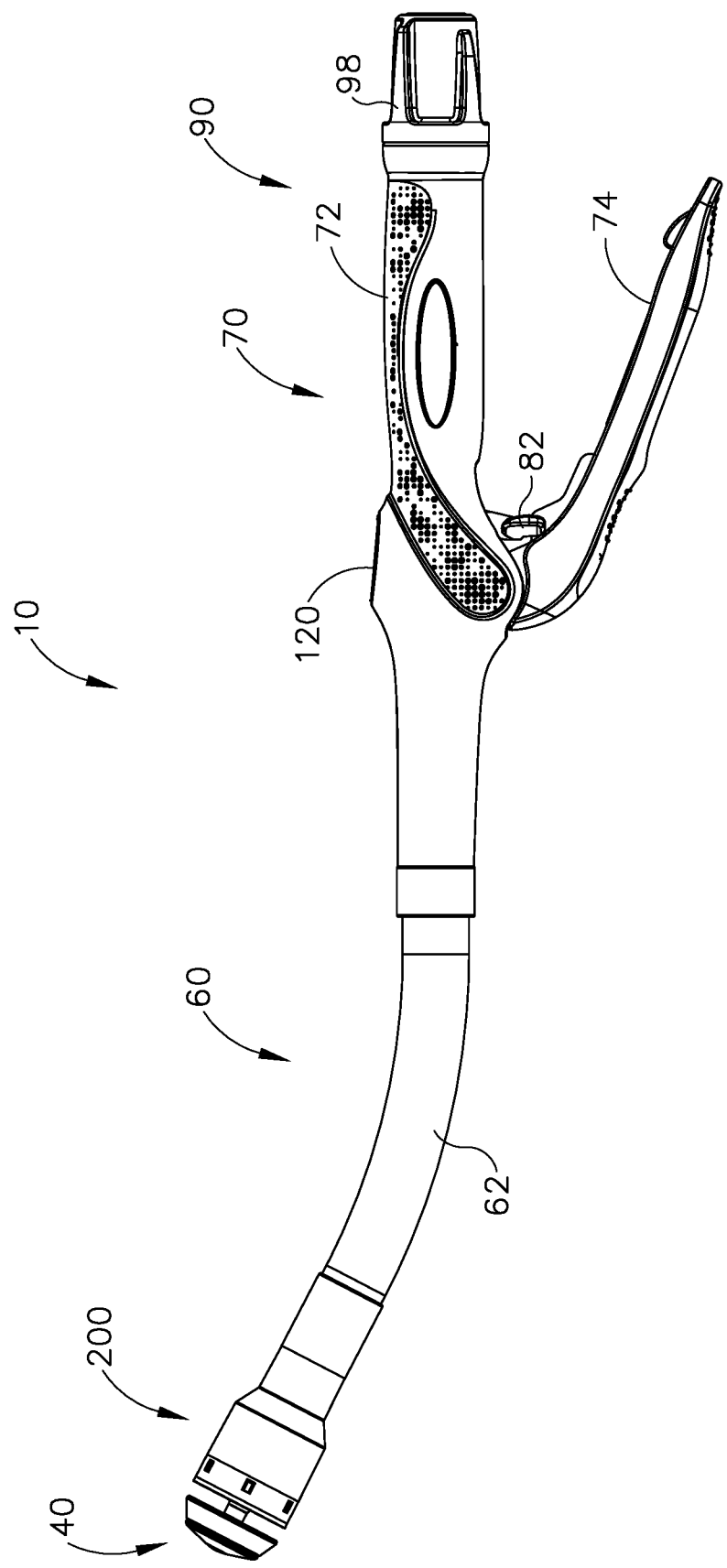
FIG. 1 depicts a side elevation view of an exemplary circular stapling surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-10 depict an exemplary circular surgical stapling instrument (10) having a stapling head assembly (200), a shaft assembly (60), and an actuator handle assembly (70), each of which will be described in more detail below. Shaft assembly (60) extends distally from actuator handle assembly (70), while stapling head assembly (200) is coupled to a distal end of shaft assembly (60). In brief, actuator handle assembly (70) is operable to actuate a staple driver member (250) of stapling head assembly (200) to drive a plurality of staples (66) out of stapling head assembly (200). Staples (66) are bent to form completed staples by an anvil (40) that is selectively attached at the distal end of instrument (10). Accordingly, tissue (2), as shown in FIGS. 9A-9E, may be stapled utilizing instrument (10).

In the present example, instrument (10) comprises a closure system and a firing system. As will be described in greater detail below, the closure system and anvil (40) are operable to clamp tissue between anvil (40) and stapling head assembly (200). As will also be described in greater detail below, the firing system and anvil (40) are operable to cut and staple tissue clamped between anvil (40) and stapling head assembly (200).

The closure system comprises a trocar (230), a trocar actuator (231), a connecting band portion (235), and an adjustment knob (98). Trocar actuator (231) is coupled to trocar (230) via connecting band portion (235). Anvil (40) may be selectively coupled to a distal end of trocar (230). Adjustment knob (98) is operable to longitudinally translate trocar (230) relative to stapling head assembly (200), thereby translating anvil (40) when anvil (40) is suitably coupled to trocar (230), and further clamping tissue between anvil (40) and stapling head assembly (200) as will be described in greater detail below.

The firing system comprises a trigger (74), a trigger actuation assembly (84), a driver actuator (64), and a staple driver member (250). Staple driver member (250) includes a knife member (240) configured to sever tissue when staple driver member (250) is actuated longitudinally. In addition, staples (66) are positioned distal to a plurality of staple drivers of staple driver member (250) such that staple driver member (250) also drives staples (66) distally when staple driver member (250) is actuated longitudinally. Thus, when trigger (74) is actuated and trigger actuation assembly (84) actuates staple driver member (250) via driver actuator (64), knife member (240) and staple drivers (252) substantially simultaneously sever tissue (2) and drive staples (66) distally relative to stapling head assembly (200) into tissue. The components and functionalities of the closure system and firing system will now be described in greater detail.

A. Exemplary Anvil

In the following discussion of anvil (40), the terms "distal" and "proximal" (and variations thereof) will be used with reference to the orientation of anvil (40) when anvil (40) is suitably coupled with trocar (230). Thus, proximal features of anvil (40) will be closer to the operator of instrument (10); while distal features of anvil (40) will be further from the operator of instrument (10).

Figure 3:
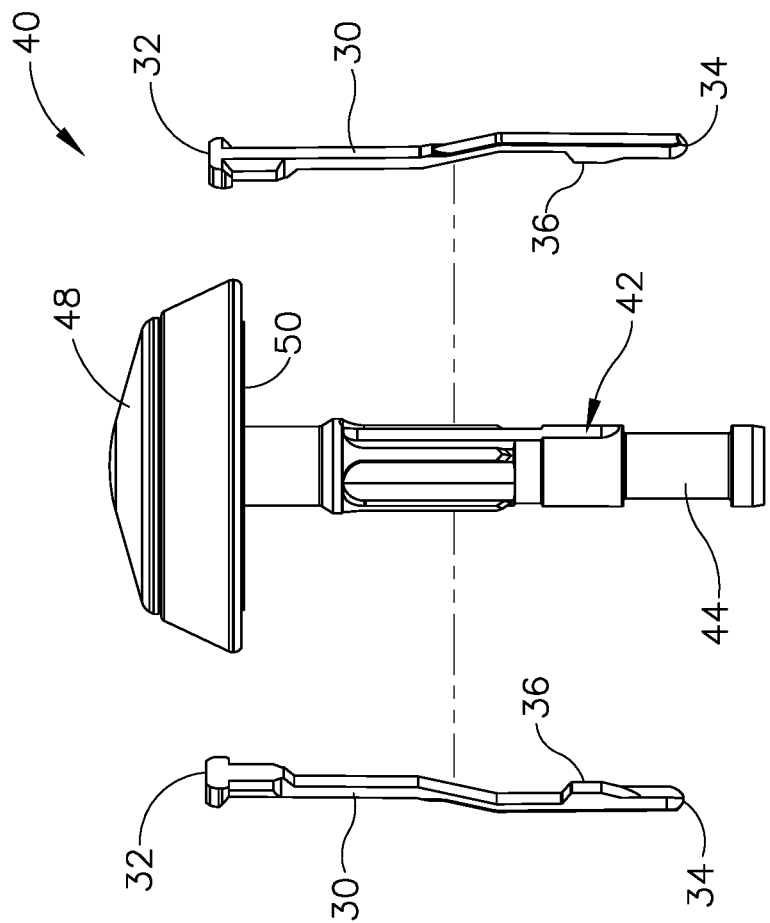
FIG. 3 depicts an exploded side elevational view of the anvil of FIG. 2.
Figure 2:
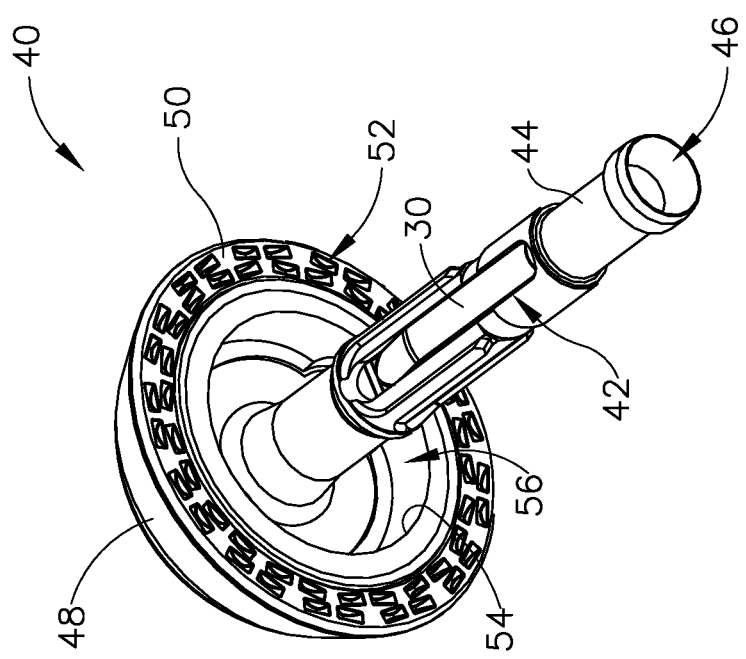
FIG. 2 depicts a perspective view of an exemplary anvil of the surgical instrument of FIG. 1.

As best seen in FIGS. 2-3, anvil (40) of the present example comprises a head (48) and a proximal shaft (44). As mentioned above and as will be described in greater detail below, anvil (40) of the present example may selectively couple to trocar (230) such that when coupled, movement of trocar (230) relative to stapling head assembly (200) also moves anvil (40) relative to stapling head assembly (200).

Head (48) includes a proximal surface (50) that defines a plurality of staple forming pockets (52). Staple forming pockets (52) are arranged in two concentric annular arrays. In some other versions, staple forming pockets (52) are arranged in three or more concentric annular arrays. Staple forming pockets (52) are configured to deform staples as the staples are driven into staple forming pockets (52). Accordingly, when anvil (40) is in the closed position and staples (66) are driven out of stapling head assembly (200) into staple forming pockets (52), each staple forming pocket (52) may deform a generally "U" shaped staple (66) into a "B" shape as is known in the art. As best seen in FIG. 2, proximal surface (50) terminates at an inner edge (54), which defines an outer boundary of an annular recess (56) surrounding proximal shaft (44).

Proximal shaft (44) defines a bore (46) and includes a pair of pivoting latch members (30) positioned in bore (46). As best seen in FIG. 3, each latch member (30) includes a "T" shaped distal end (32), a rounded proximal end (34), and a latch shelf (36) located distal to proximal end (34). "T" shaped distal ends (32) secure latch members (30) within bore (46). Latch members (30) are positioned within bore (46) such that proximal ends (34) are positioned at the proximal ends of lateral openings (42), which are formed through the sidewall of proximal shaft (44). Lateral openings (42) thus provide clearance for proximal ends (34) and latch shelves (36) to deflect radially outwardly from the longitudinal axis defined by proximal shaft (44). However, latch members (30) are configured to resiliently bias proximal ends (34) and latch shelves (36) radially inwardly toward the longitudinal axis defined by proximal shaft (44). Latch members (30) thus act as retaining clip to allow anvil (40) to be selectively secured to trocar (230) of stapling head assembly (200). It should be understood, however, that latch members (30) are merely optional. Anvil (40) may be removably secured to a trocar (230) using any other suitable components, features, or techniques.

In addition to or in lieu of the foregoing, anvil (40) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pub. No. 2016/0374684, the disclosures of which are incorporated by reference herein. Still other suitable configurations will be apparent to one of ordinary skill in the art in view of the teachings herein.

B. Exemplary Stapling Head Assembly

Figure 4:
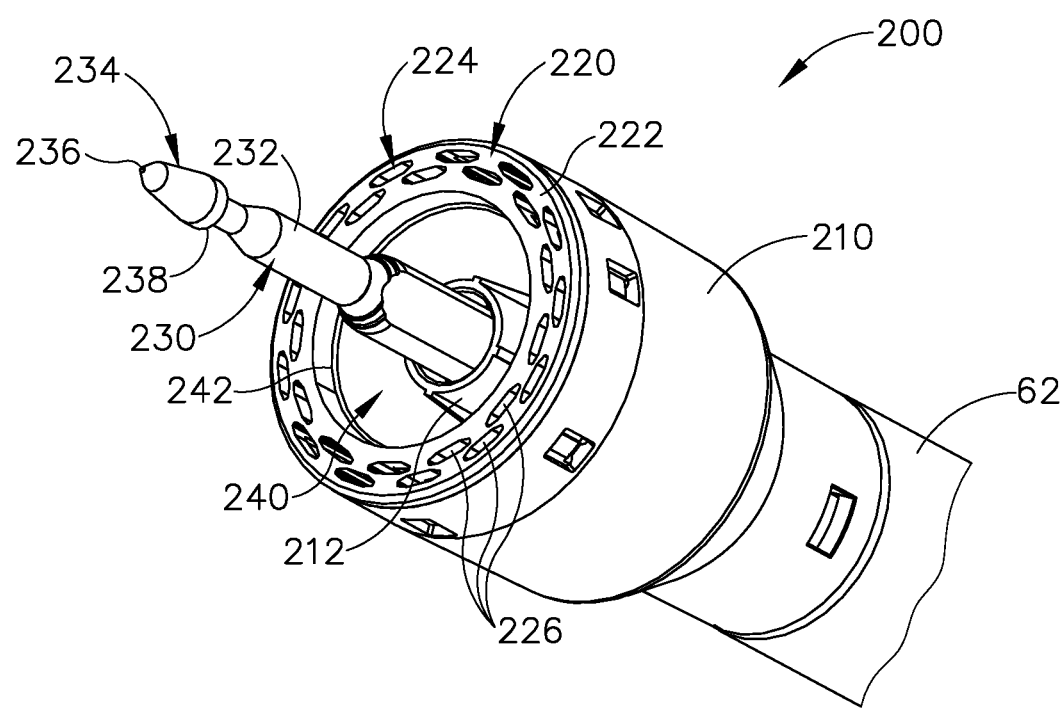
FIG. 4 depicts a perspective view of a stapling head assembly of the surgical instrument of FIG. 1.
Figure 5:
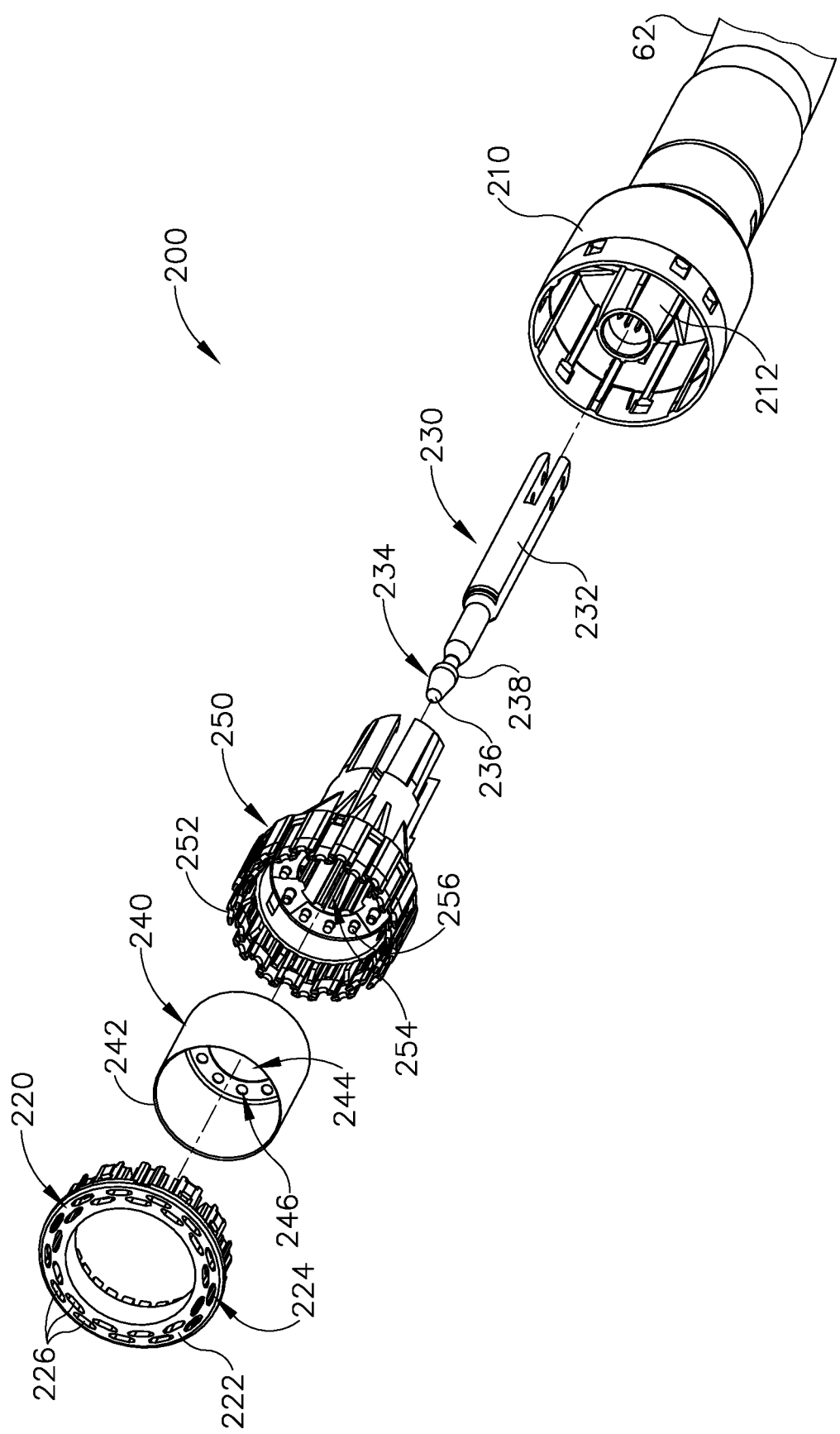
FIG. 5 depicts an exploded perspective view of the stapling head assembly of FIG. 5.

As best seen in FIGS. 4-5, stapling head assembly (200) of the present example is coupled to a distal end of shaft assembly (60) and comprises a tubular casing (210) housing a slidable staple driver member (250). A cylindraceous inner core member (212) extends distally within tubular casing (210). Tubular casing (210) is fixedly secured to an outer sheath (62) of shaft assembly (60), such that tubular casing (210) serves as a mechanical ground for stapling head assembly (200).

Trocar (230) is positioned coaxially within inner core member (212) of tubular casing (210). As mentioned above and as will be described in greater detail below, trocar (230) is operable to translate distally and proximally relative to tubular casing (210) in response to rotation of adjustment knob (98) relative to body (72) of handle assembly (70). Trocar (230) comprises a shaft (232) and a head (234). Head (234) includes a pointed tip (236) and an inwardly extending proximal surface (238). Shaft (232) thus provides a reduced outer diameter just proximal to head (234), with surface (238) providing a transition between that reduced outer diameter of shaft (232) and the outer diameter of head (234). While tip (236) is pointed in the present example, tip (236) is not sharp. Tip (236) will thus not easily cause trauma to tissue due to inadvertent contact with tissue. Head (234) and the distal portion of shaft (232) are configured for insertion in bore (46) of anvil (40). Proximal surface (238) and latch shelves (36) have complementary positions and configurations such that latch shelves (36) engage proximal surface (238) when proximal shaft (44) of anvil (40) is fully seated on trocar (230). Anvil (40) may thus secure to trocar (230) through a snap fitting between latch members (30) and head (234). In addition, or in the alternative, trocar (230) may include a magnetic portion (not shown) which may attract anvil (40) towards trocar (230). Still further configurations and arrangements for anvil (40) and trocar (230) will be apparent to one of ordinary skill in the art in view of the teachings herein.

Figure 9A:
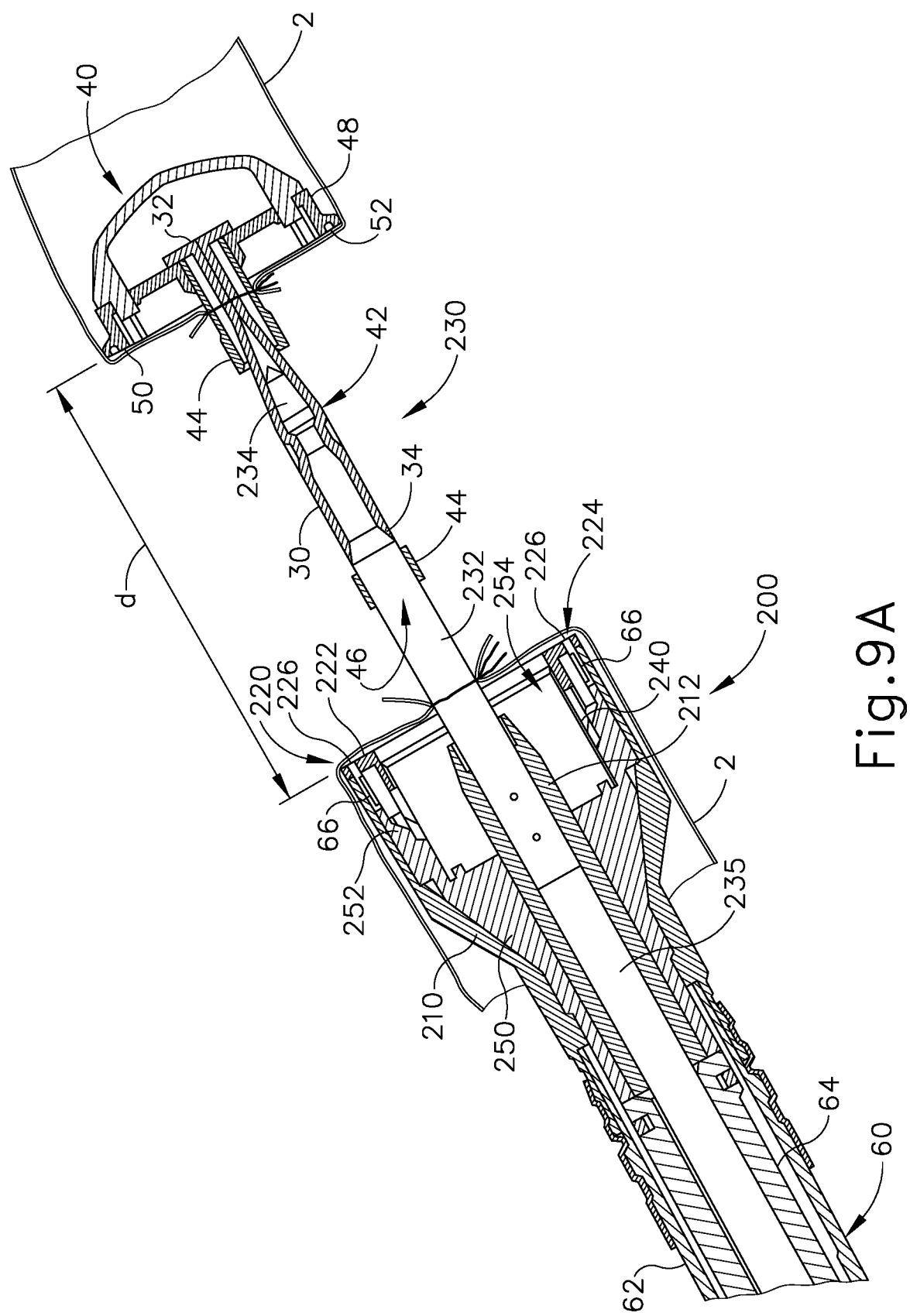
FIG. 9A depicts an enlarged longitudinal cross-section view of the stapling head assembly of FIG. 5, showing the anvil of FIG. 2 in a first open position, where the anvil is within a first tubular portion of tissue and the stapling head assembly is within a second tubular portion of tissue.
Figure 9B:
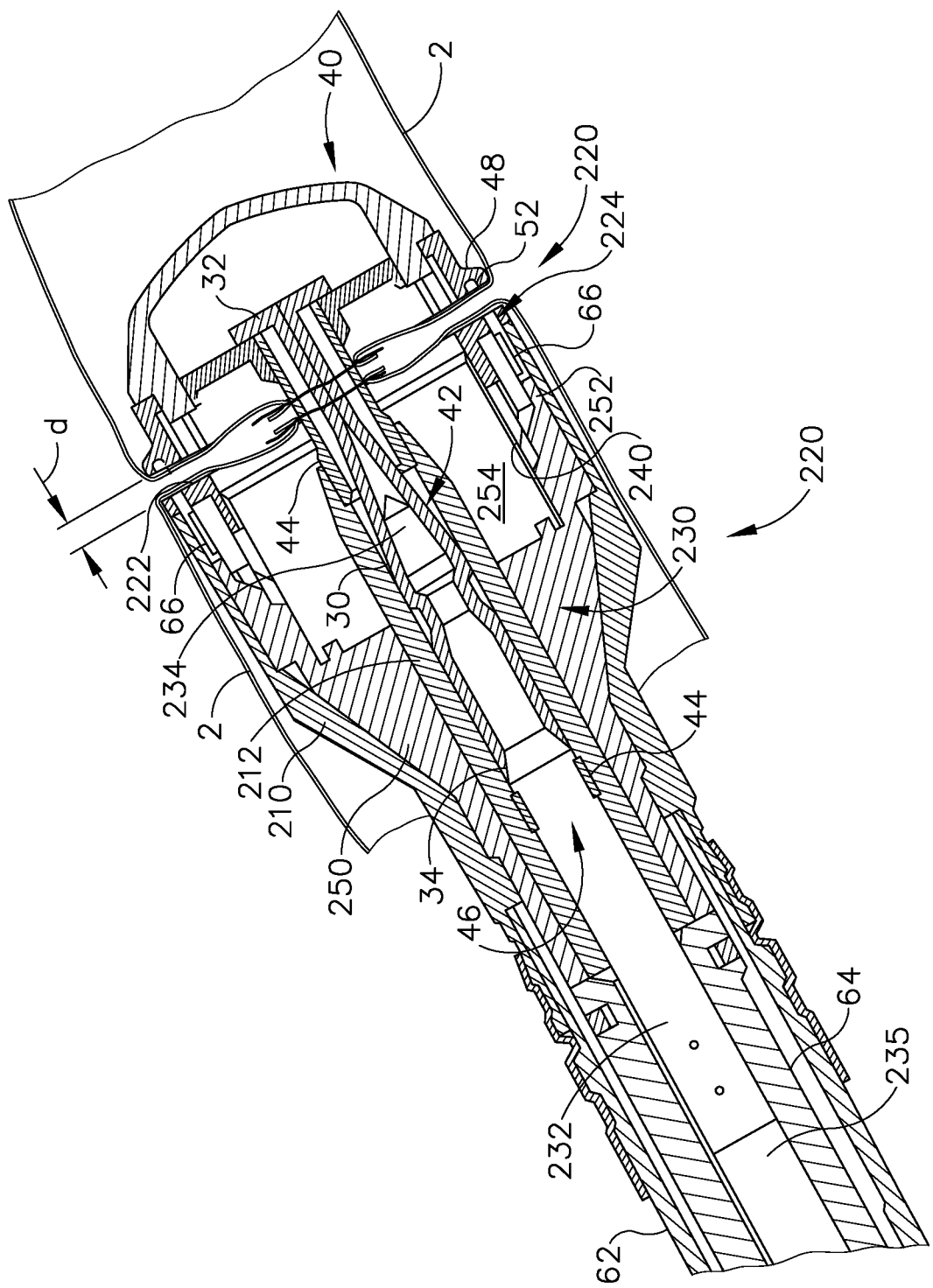
FIG. 9B depicts an enlarged longitudinal cross-sectional view of the stapling head assembly of FIG. 5, showing the anvil of FIG. 2 in a closed position, where the anvil is within the first tubular portion of tissue and the stapling head assembly is within the second tubular portion of tissue.

Staple driver member (250) is operable to actuate longitudinally within tubular casing (210) in response to rotation of trigger (74) of actuator handle assembly (70) as will be described in greater detail below. Staple driver member (250) includes two distally presented concentric annular arrays of staple drivers (252). Staple drivers (252) are arranged to correspond with the arrangement of staple forming pockets (52) described above. As best seen in FIGS. 9A-9B, each staple driver (252) is located underneath a corresponding staple (66). The arrangement of staple drivers (252) may be modified just like the arrangement of staple forming pockets (52) as described above. Staple driver member (250) also defines a bore (254) that is configured to coaxially receive core member (212) of tubular casing (210). An annular array of studs (256) project distally from a distally presented surface surrounding bore (254).

A cylindraceous knife member (240) is coaxially positioned within staple driver member (250). Knife member (240) includes a distally presented, sharp circular cutting edge (242). Knife member (240) is sized such that knife member (240) defines an outer diameter that is smaller than the diameter defined by the inner annular array of staple drivers (252). Knife member (240) also defines an opening that is configured to coaxially receive core member (212) of tubular casing (210). An annular array of openings (246) formed in knife member (240) is configured to complement the annular array of studs (256) of staple driver member (250), such that knife member (240) is fixedly secured to staple driver member (250) via studs (256) and openings (346). Therefore, when stapling driver member (250) is actuated relative to tubular casing (210), so is knife member (240). Other suitable structural relationships between knife member (240) and stapler driver member (250) will be apparent to those of ordinary skill in the art in view of the teachings herein.

A deck member (220) is fixedly secured to tubular casing (210). Deck member (220) includes a distally presented deck surface (222) defining two concentric annular arrays of staple openings (224), where each staple opening (224) has its own staple pocket (226) housing a staple (66). Staple openings (224) and staple pockets (226) are arranged to correspond with the arrangement of staple drivers (252) and staple forming pockets (52) described above. Accordingly, when staple driver member (250) is actuated distally relative to tubular casing (210) in response to rotation of trigger (74), each staple driver (252) drives a corresponding staple (66) out of its staple pocket (226) and through a corresponding staple opening (224) of deck member (220). When anvil (40) is in the closed position, staples (66) are driven into a corresponding staple forming pockets (52) to bend legs (68) of the staples (66), thereby stapling the material located between anvil (40) and stapling head assembly (200).

The arrangement of staple openings (224) may be modified just like the arrangement of staple forming pockets (52) as described above. It should also be understood that various structures and techniques may be used to contain staples (66) within stapling head assembly (200) before stapling head assembly (200) is actuated. Such structures and techniques that are used to contain staples within stapling head assembly (200) may prevent the staples from inadvertently falling out through staple openings (224) before stapling head assembly (200) is actuated. Various suitable forms that such structures and techniques may take will be apparent to those of ordinary skill in the art in view of the teachings herein.

As best seen in FIG. 5, deck member (220) defines an inner diameter that is just slightly larger than the outer diameter defined by knife member (240). Deck member (220) is thus configured to allow knife member (240) to translate distally to a point where cutting edge (242) is distal to deck surface (222).

In addition to or in lieu of the foregoing, stapling head assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or U.S. Pub. No. 2016/0374684, the disclosures of which are incorporated by reference herein. Still other suitable configurations will be apparent to one of ordinary skill in the art in view of the teachings herein.

C. Exemplary Shaft Assembly

Stapling head assembly (200) and trocar (230) are positioned at a distal end of shaft assembly (60), as shown in FIGS. 9A-9D. Shaft assembly (60) of the present example comprises an outer tubular member (62), a driver actuator (64), and connecting band portion (235). Outer tubular member (62) is coupled to tubular casing (210) of stapling head assembly (200) and to a body (72) of actuator handle assembly (70), thereby providing a mechanical ground for the actuating components therein. As seen in FIGS. 9A-9B, the proximal end of driver actuator (64) is coupled to a trigger actuation assembly (84) of actuator handle assembly (70), as described below. The distal end of driver actuator (64) is coupled to staple driver member (250) such that the rotation of trigger (74) longitudinally actuates staple driver member (250). As shown in FIGS. 9A-9D, driver actuator (64) comprises a tubular member having an open longitudinal axis such that trocar actuator (231) and connecting band portion (235), which are coupled to trocar (230), may actuate longitudinally within and relative to driver actuator (64). Other components may be disposed within driver actuator (64) as will be apparent to one of ordinary skill in the art in view of the teachings herein.

In the present example, shaft assembly (60) extends distally from actuator handle assembly (70) with a preformed bend. In some versions, the preformed bend is configured to facilitate positioning of stapling head assembly (200) within a patient's colon. Various suitable bend angles or radii that may be used will be apparent to those of ordinary skill in the art in view of the teachings herein. As mentioned above, actuator (231) is coupled with trocar (230) via flexible band portion (235). Flexible band portion (235) extends from a distal end of actuator (231), located proximal to the preformed bend, to couple with trocar (230), located distal to the preformed bend. Flexible band portion (235) may be dimensioned to flex during translation along the longitudinal profile of the preformed bend of shaft assembly (60). In such cases, trocar actuator (231) may be slidably housed within actuator handle assembly (70), while trocar (230) is slidably housed within tubular casing (210). Flexible band portion (235) may be connected to both trocar (230) and actuator (231) via pins or any other suitable means as would be apparent to one having ordinary skill in the art in view of the teachings herein.

Shaft assembly (60) may be further constructed in accordance with at least some of the teachings of U.S. Pat. Nos. 5,205,459; 5,271,544; 5,275,322; 5,285,945; 5,292,053;

5,333,773; 5,350,104; 5,533,661; 8,910,847; and/or 9,936,949, the disclosures of which are incorporated by reference herein; and/or in accordance with other configurations as will be apparent to one of ordinary skill in the art in view of the teachings herein.

D. Exemplary Actuator Handle Assembly

Referring now to FIGS. 6-8B, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 8A) to a fired position (shown in FIG. 8B) actuates driver actuator (64) described above. A spring (78) is coupled to body (72) and trigger (74) to bias trigger (74) towards the unfired position. Lockout feature (82) is a pivotable member that is coupled to body (72). In a first, locked position, as shown in FIG. 8A, lockout feature (82) is pivoted upwards and away from body (72) such that lockout feature (82) engages trigger (74) and mechanically resists actuation of trigger (74) by a user. In a second, unlocked position, such as that shown in FIGS. 1 and 8B, lockout feature (82) is pivoted downward such that trigger (74) may be actuated by the user. Accordingly, with lockout feature (82) in the second position, trigger (74) can engage trigger actuation assembly (84) to fire instrument (10).

Figure 8A:
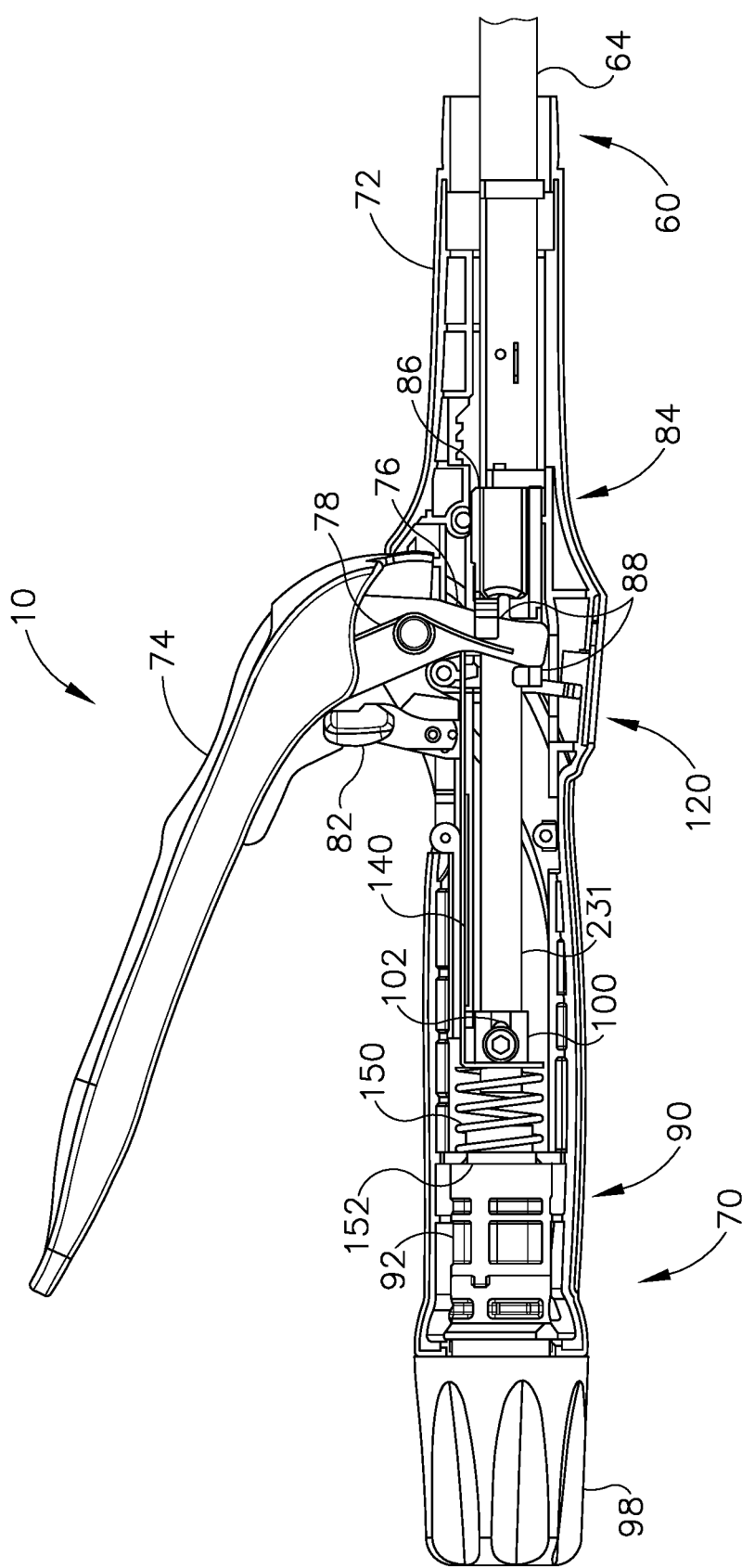
FIG. 8A depicts an enlarged side elevation view of an exemplary actuator handle assembly of the surgical instrument of FIG. 1 with a portion of the body removed, showing a trigger in an unfired position and a lockout feature in a locked position.
Figure 8B:
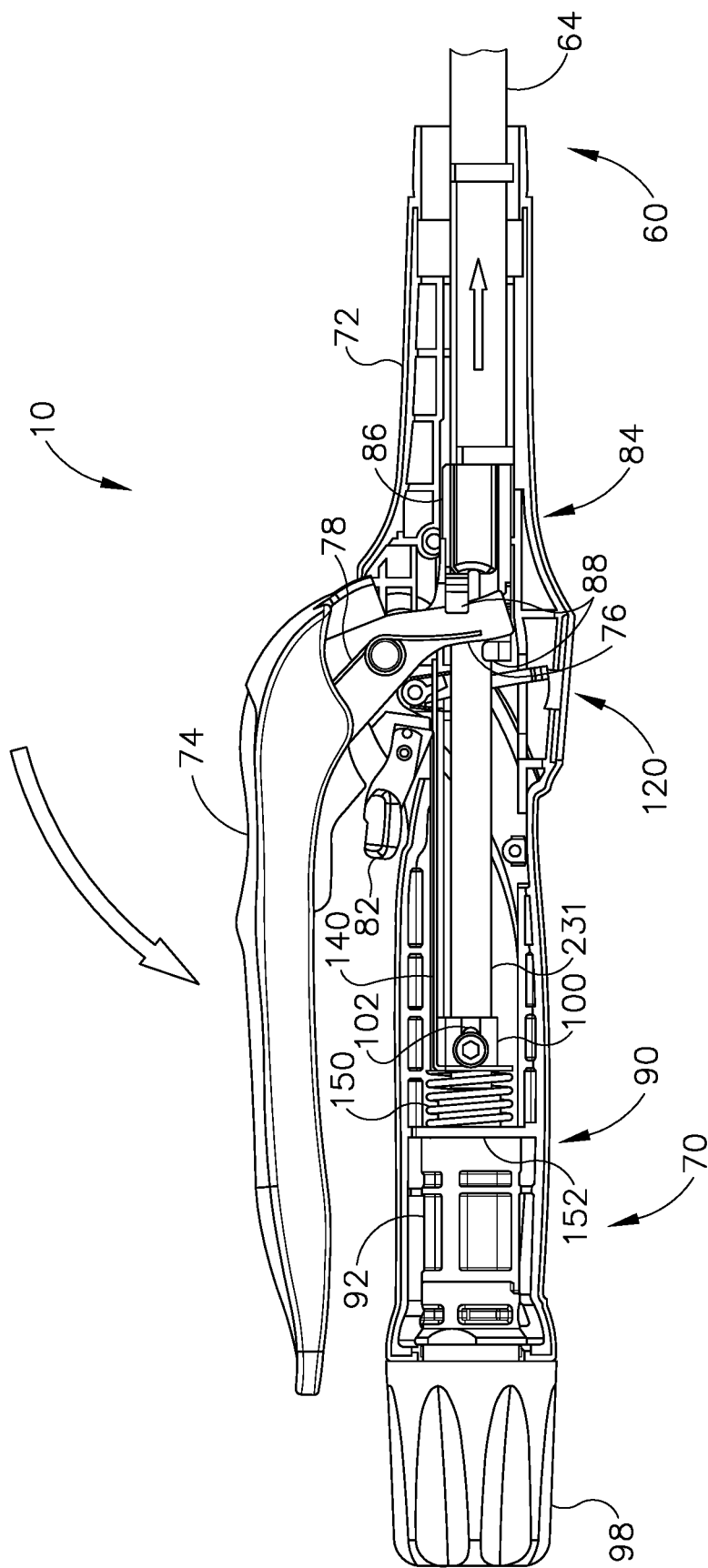
FIG. 8B depicts an enlarged side elevation view of the actuator handle assembly of FIG. 8A, showing the trigger in a fired position and the lockout feature in an unlocked position.

As shown in FIGS. 8A-8B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. Nos. 5,205,459; 5,271,544; 5,275,322; 5,285,945; 5,292,053; 5,333,773; 5,350,104; 5,533,661; 8,910,847; and/or 9,936,949 the disclosures of which are incorporated by reference herein; and/or in accordance with other configurations as will be apparent to one of ordinary skill in the art in view of the teachings herein.

Figure 6:
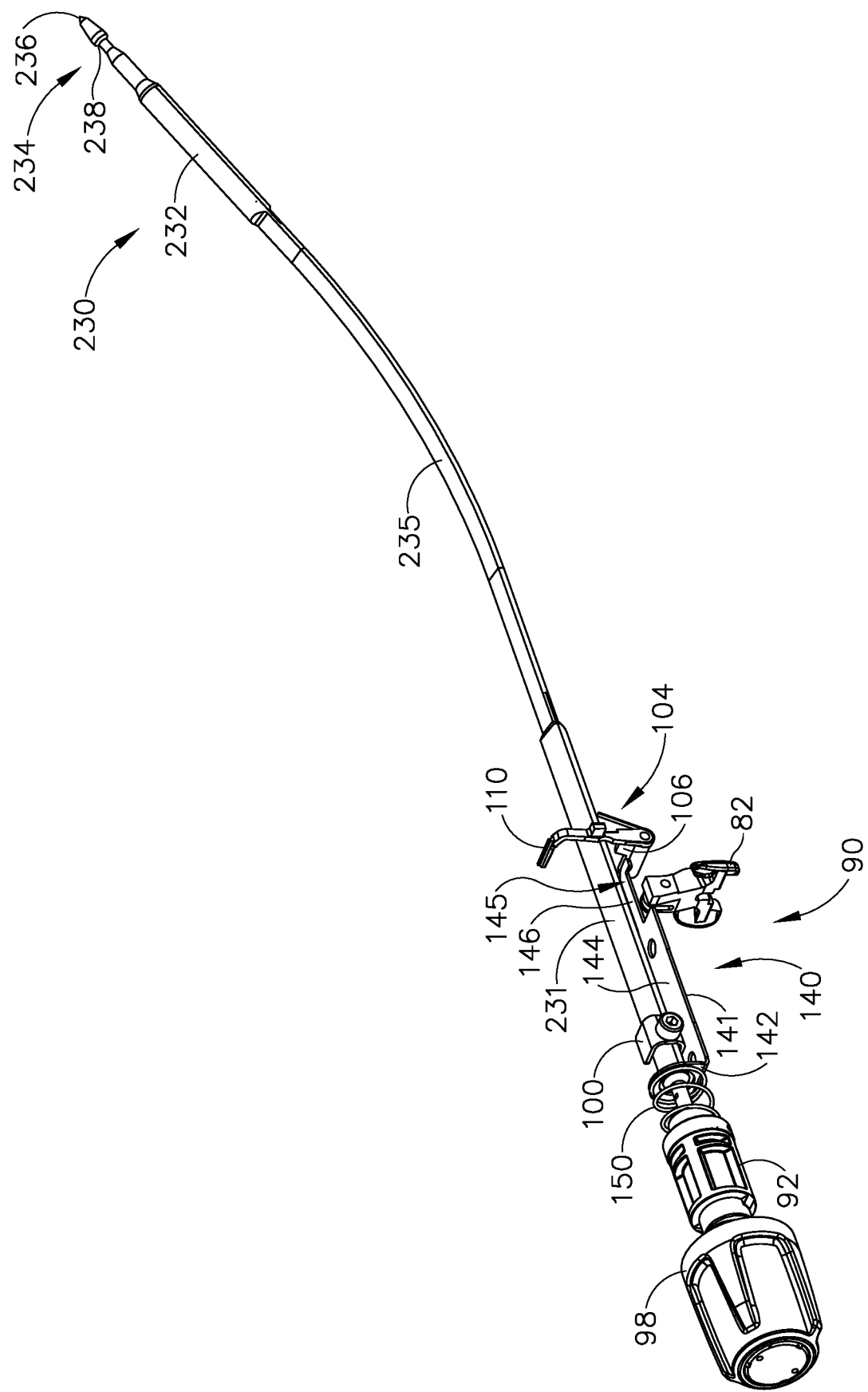
FIG. 6 depicts a perspective view of an exemplary closure system of the surgical instrument of FIG. 1.
Figure 7:
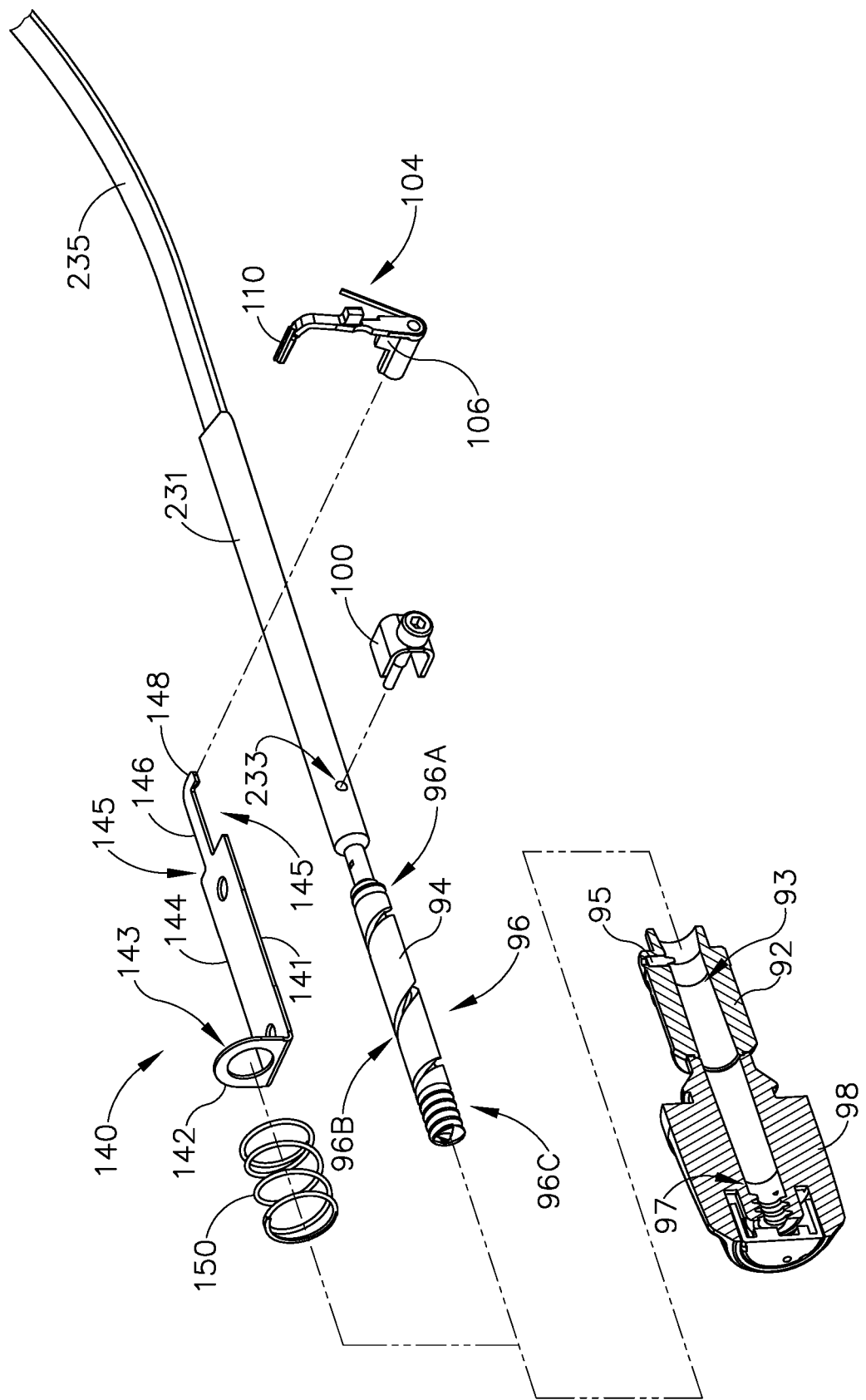
FIG. 7 depicts an exploded perspective view of the closure system of FIG. 1.

Body (72) also houses trocar actuation assembly (90) configured to actuate trocar (230) longitudinally in response to rotation of adjustment knob (98). As best shown in FIGS. 6-7, trocar actuation assembly (90) of the present example comprises adjustment knob (98), a grooved shank (94), and a sleeve (92). Grooved shank (94) is slidably housed within a channel (93) defined by both adjustment knob (98) and sleeve (92). Grooved shank (94) of the present example is located at a proximal end of trocar actuator (231). In other versions, grooved shank (94) and trocar actuator (231) may alternatively be separate components that engage to transmit longitudinal movement. While grooved shank (94) is configured to translate within body (72), grooved shank (94) does not rotate within body (72). Adjustment knob (98) is rotatably supported by the proximal end of body (72) and is operable to rotate sleeve (92), which is engaged with grooved shank (94) via an internal tab (95). Adjustment knob (98) also defines internal threading (97) as will be described in greater detail below. Grooved shank (94) of the present example comprises a continuous groove (96) formed in the outer surface of grooved shank (94). Accordingly, when adjustment knob (98) is rotated, internal tab (95) of sleeve (92) rides within groove (96) and grooved shank (94) is longitudinally actuated relative to sleeve (92). Since grooved shank (94) is located at the proximal end of trocar actuator (231), rotating adjustment knob (98) in a first direction advances trocar actuator (231) distally relative to actuator handle assembly (70). When trocar (230) is coupled with anvil (40), anvil (40) also advances distally relative to stapling head assembly (200) thereby increasing the distance between proximal surface (50) of the anvil (40) and distally presented deck surface (222) of deck member (220), otherwise known as a gap distance d. By rotating adjustment knob (98) in the opposite direction, trocar actuator (231) is actuated proximally relative to actuator handle assembly (70) to reduce the gap distance d between anvil (40) and stapling head assembly (200) when trocar (230) is coupled with anvil (40). Thus, trocar actuation assembly (90) is operable to actuate trocar (230) in response to rotating adjustment knob (98). Other suitable configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 7, distal portion (96A) comprises a fine pitch or a high number of grooves over a short axial length of grooved shank (94). Middle portion (96B) comprises a section with comparably coarser pitch or fewer grooves per axial length such that relatively few rotations are required for internal tab (95) of sleeve (92) to traverse along axial distance. When anvil (40) is in an initial, distal position in relation to stapling head assembly (200) (as shown in FIG. 9A) the internal tab (95) of sleeve (92) is positioned in middle portion (96B). Accordingly, the gap distance d may be quickly reduced through relatively few rotations of adjustment knob (98) while the internal tab (95) of sleeve (92) traverses middle portion (96B). Proximal portion (96C) of the present example is substantially like distal portion (96A) and comprises a fine pitch or a high number of grooves over a short axial distance of grooved shank (94) such that many rotations are required to traverse the short axial distance. Proximal portion (96C) of the present example is engaged by the internal threading (97) defined by knob (98) when anvil (40) is substantially near to stapling head assembly (200) (as shown in FIG. 9B), such that indicator bar (110) moves within indicator window (120) along scale (130) to indicate that the anvil gap is within a desired operating range, as will be described in more detail below. Accordingly, when grooved shank (94) reaches a proximal position where the proximal portion (96C) of groove (96) engages internal threading (97) of knob (98), each rotation of adjustment knob (98) may reduce the gap distance d by a relatively small amount to provide for fine tuning. Internal tab (95) of sleeve (92) may be disengaged from groove (96) when proximal portion (96C) is engaged with internal threading (97) of knob (98).

Trocar actuation assembly (90) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or 9,936, 949 the disclosures of which are incorporated by reference herein; and/or in accordance with other configurations as will be apparent to one of ordinary skill in the art in view of the teachings herein.

As noted above, gap distance d corresponds to the distance between anvil (40) and stapling head assembly (200). When instrument (10) is inserted into a patient, this gap distance d may not be easily viewable. Accordingly, a moveable indicator bar (110) is provided to be visible through an indicator window (120) positioned opposite to trigger (74). As will be described in greater detail below, indicator bar (110) is operable to move in response to rotation of adjustment knob (98) such that the position of indicator bar (110) is representative of the gap distance d. Indicator window (120) further comprises a scale (130) which indicates that the anvil gap is within a desired operating range (e.g., a green colored region or "green zone") and a corresponding staple compression representation at each end of scale (130). By way of example only, a first staple image (132) depicts a large staple height while a second staple image (134) depicts a small staple height. Accordingly, a user can view the position of the coupled anvil (40) relative to the stapling head assembly (200) via indicator bar (110) and scale (130). The user may then adjust the positioning of anvil (40) via adjustment knob (98) accordingly.

In the example shown in FIGS. 6-7, a U-shaped clip (100) is attached to an intermediate portion of trocar actuator (231) via a through hole (233) located distally of grooved shank (94). In the present example, an extension of trocar actuator (231) engages a slot in the housing of handle assembly (70) to prevent trocar actuator (231) from rotating about its axis when adjustment knob (98) is rotated. It may be necessary to calibrate the proper placement of trocar actuator (231) within instrument (10) such that indicator bar (110) may show a proper gap distance d during exemplary use. U-shaped clip (100) of the present example further includes an elongated slot (102) on each of its opposite sides for receiving an attachment member, such as a screw, bolt, pin, etc., to selectively adjust the longitudinal position of elongated slot (102) of U-shaped clip (100) relative to trocar actuator (231) for purposes of calibrating indicator bar (110) relative to scale (130). In some versions, the attachment member (e.g., screw, bolt, pin, etc.) engages with a portion of body (72) to substantially prevent trocar actuator (231) from rotating about its axis when adjustment knob (98) is rotated.

As shown in FIGS. 6-7, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (143) to slidably mount onto trocar actuator (231) and/or grooved shank (94). A coil spring (150) is interposed between flange (142) and a boss (152) of body (72) to bias flange (142) against U-shaped clip (100). Accordingly, when U-shaped clip (100) actuates distally with trocar actuator (231) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (231) and/or grooved shank (94) translate proximally, thereby compressing coil spring (150). In some versions, indicator bracket (140) may be fixedly attached to trocar actuator (231) and/or grooved shank (94).

In the present example, a portion of lockout feature (82) abuts a surface (141) of indicator bracket (140) when indicator bracket (140) is in a longitudinal position that does not correspond to when gap distance d is within a desired operating range (e.g., a green colored region or "green zone"). When gap distance d is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 7, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (not shown) to show the relative gap distance d between proximal surface (50) of anvil (40) and distally presented deck surface (222) of deck member (220).

Of course indicator bracket (140), indicator (104), and/or actuator handle assembly (70) may be further constructed in accordance with at least some of the teachings of U.S. Pat. Nos. 5,205,459; 5,271,544; 5,275,322; 5,285,945; 5,292,053; 5,333,773; 5,350,104; 5,533,661; and/or 8,910,847; and/or 9,936,949 the disclosures of which are incorporated by reference herein; and/or in accordance with other configurations as will be apparent to one of ordinary skill in the art in view of the teachings herein.

E. Exemplary Use of Circular Stapling Surgical Instrument

FIGS. 8A-8B and FIGS. 9A-9E show an exemplary use of circular stapling surgical instrument (10) in accordance with the description above. As mentioned above, anvil (40) may selectively couple with trocar (230) such that movement of trocar (230) relative to tubular casing (210) and deck member (220) leads to movement of anvil (40) relative to tubular casing (210) and deck member (220). With anvil (40) as a separate component, it should be understood that anvil (40) may initially be inserted and secured to a portion of tissue (2) prior to being coupled with trocar (230). By way of example only, anvil (40) may be inserted into and secured to a first tubular portion of tissue (2) while stapling head assembly (200) is inserted into and secured to a second tubular portion of tissue (2). For instance, the first tubular portion of tissue (2) may be sutured to or about a portion of anvil (40), and the second tubular portion of tissue (2) may be sutured to or about trocar (230).

As shown in FIG. 9A, anvil (40) may then be coupled to trocar (230) in accordance with the description above, such as a snap fitting between latch members (30) of anvil (40) and head (234) of trocar (230). In FIG. 9A, trocar (230) is shown in a distal most actuated position. Trocar (230) may be actuated to the distal most actuated position by rotation of knob (98) in accordance with the description above. Such an extended position for trocar (230) may provide a larger area to which tissue (2) may be coupled prior to attachment of anvil (40). The extended position of trocar (230) may also provide for easier attachment of anvil (40) to trocar (230). At the position shown in FIG. 9A, trigger (74) is locked in the position shown in FIG. 8A by lockout feature (82), as lockout feature (82) may not pivot to unlock trigger (74) due to interference caused by surface (141) of indicator bracket (140) in accordance with the description above.

As mentioned above, when anvil (40) is coupled to trocar (230), rotation of adjustment knob (98) may translate both trocar (230) and anvil (40), thereby enlarging or reducing gap distance d. For instance, as shown sequentially in FIGS. 9A-9B, anvil (40) is shown actuating proximally relative to actuator handle assembly (70) from an initial, open position (FIG. 9A) to a closed position (FIG. 9B) where gap distance d is brought within a suitable predetermined range. It should be understood that in the position shown in FIG. 9A, grooved shank (94) is in a distal position where the middle portion (96B) of groove (96) engages internal tab (95) of sleeve (92).

When gap distance d is brought within a suitable predetermined range, indicator bar (110) may move within indicator window (120) to show the relative gap distance d is within a desired operating range (e.g. a green colored region or "green zone") in accordance with the description above. Likewise, it should be understood that in the position shown in FIG. 9B, grooved shank (94) is in a proximal position where the proximal portion (96C) of groove (96) engages internal threading (97) of knob (98). Therefore, each rotation of adjustment knob (98) may reduce the gap distance d by a relatively small amount to provide for fine tuning.

Figure 9C:
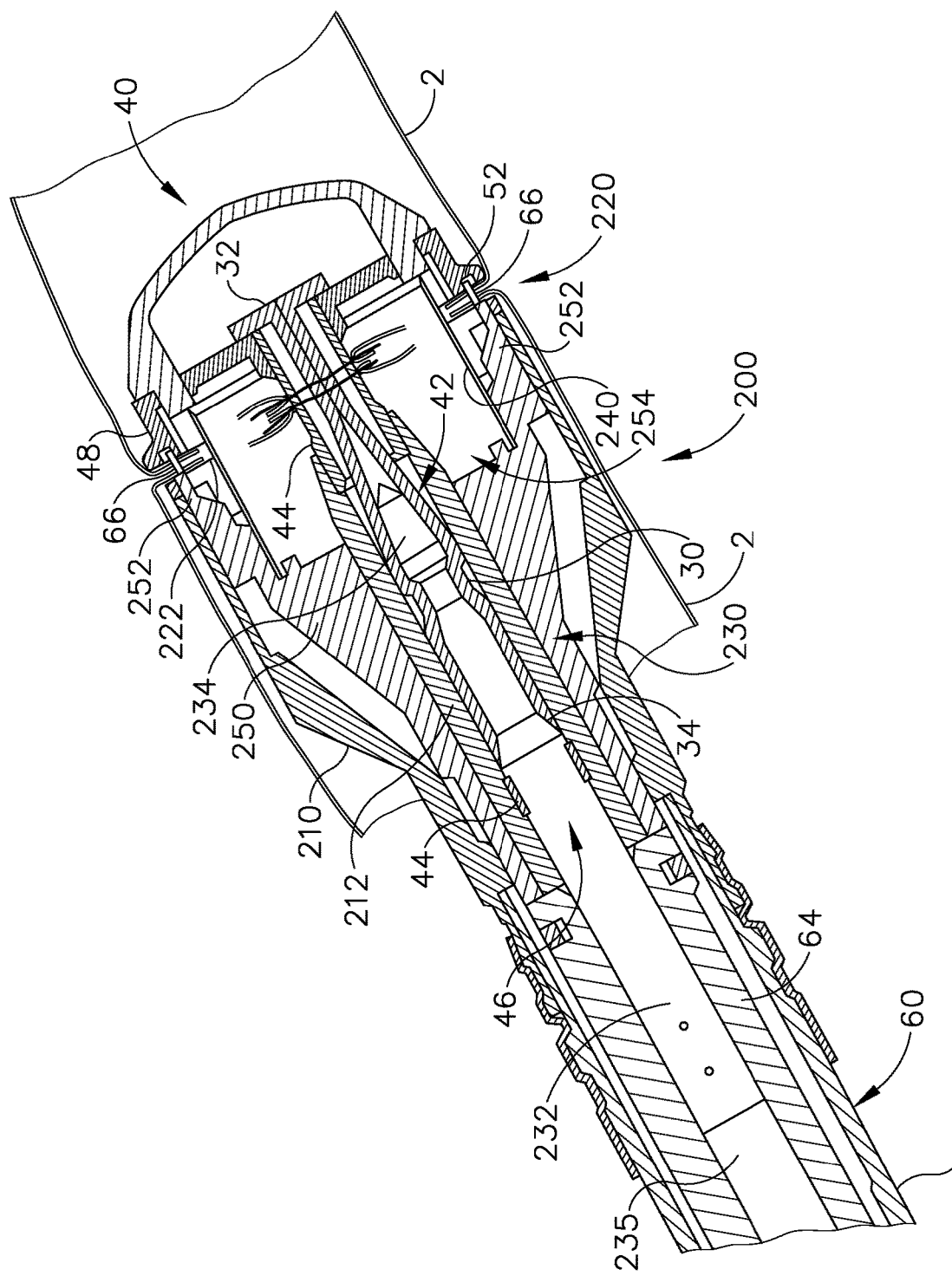
FIG. 9C depicts an enlarged longitudinal cross-sectional view of the stapling head assembly of FIG. 5, showing the anvil of FIG. 2 in the closed position, were an exemplary staple driver and blade are in a fired position such that the first tubular portion of tissue and the second tubular portion of tissue are stapled together with excess tissue severed.

As shown between FIGS. 8A-8B, when gap distance d is brought within a suitable predetermined range, lockout feature (82) may be pivoted relative to body (72) to an unlocked position such that trigger (74) may pivot relative to body (72) to engage trigger actuation assembly (84) in accordance with the description above. As shown in FIG. 8B, with lockout feature (82) pivoted into the unlocked position, trigger (74) is pivoted toward body (72) such that trigger arms (76) drive against tabs (88) to distally actuate slidable trigger carriage (86) and driver actuator (64). As shown in FIG. 9C, distal actuation of driver actuator (64) drives slidable staple driver member (250), staples drivers (252), and cylindraceous knife member (240) distally. Distal advancement of staple drivers (252) drive staples (66) against corresponding staple forming pockets (52) thereby stapling tissue (2) between anvil (40) and stapling head assembly (200) to form a continuous tubular portion of tissue (2). Additionally, distal advancement of cylindraceous knife member (240) severs excess tissue located radially interior to newly formed staples (66). Stapling head assembly (200) is operable to staple and sever tissue (2) by a user pivoting a trigger (74) of actuator handle assembly (70), as will be described in greater detail below.

Figure 9D:
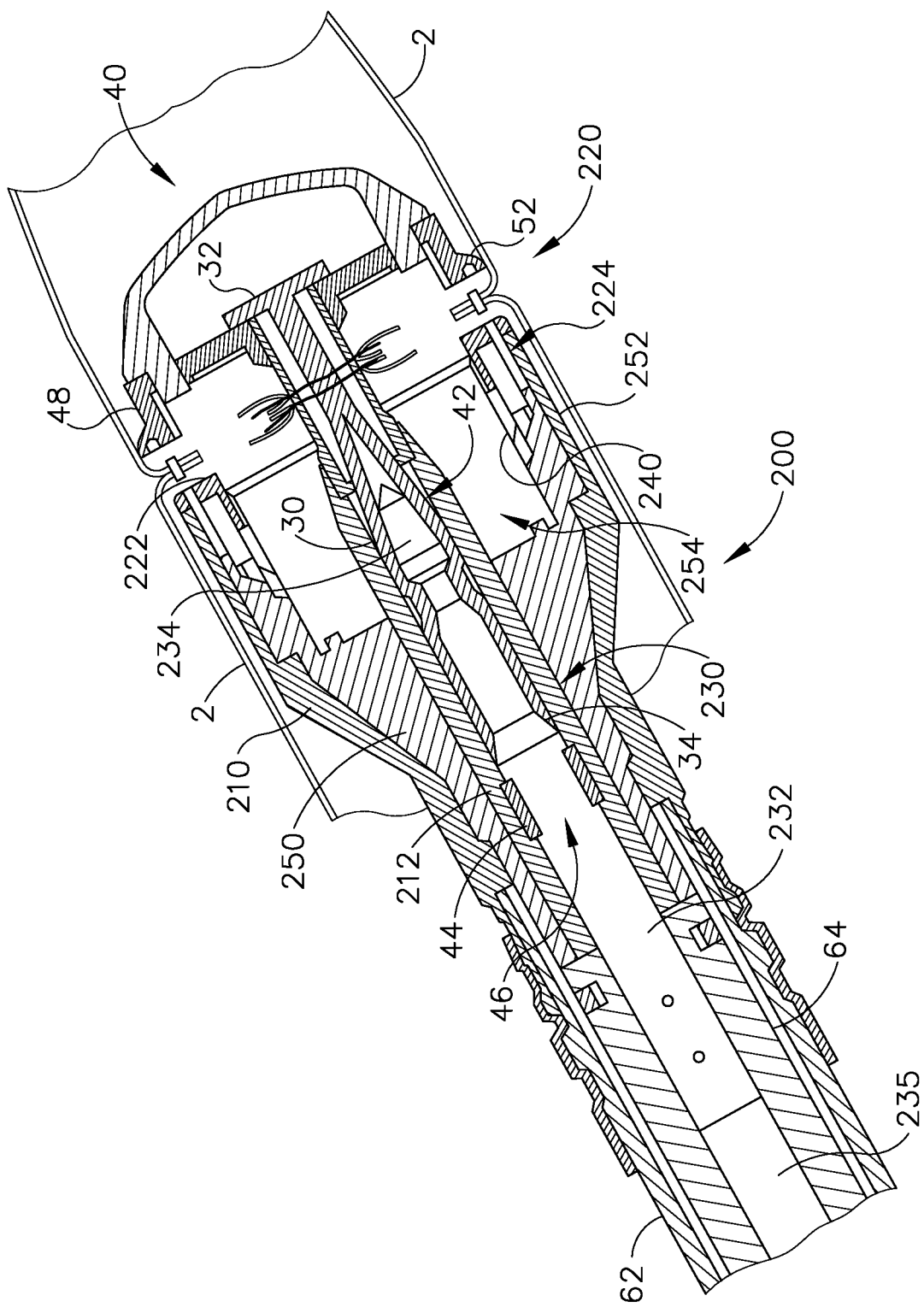
FIG. 9D depicts an enlarged longitudinal cross-sectional view of the stapling head assembly of FIG. 5, showing the anvil of FIG. 2 in a second open position, where the first tubular portion of tissue and the second tubular portion of tissue are attached.

As best shown in FIG. 9D, once trigger (74) has been actuated to staple and sever tissue (2), a user may then turn rotatable knob (98) to distally advance anvil (40), thereby releasing portions of tissue (2) grasped between proximal surface (50) of anvil (40) and distally presented deck surface (222) of deck member (220). As best shown in FIG. 9E, with previously grasped tissue (2) released, a user may then remove instrument (10), thereby leaving a continuous tubular portion of tissue (2) behind.

II. Exemplary Alternative Actuation Handle Assemblies for Circular Stapling Surgical Instrument In some instances, the operator may fail to sufficiently actuate trigger (74) in order to suitably actuate slidable trigger carriage (86), driver actuator (64), staple driver (250), and knife (240) in accordance with the description above. For example, the operator may lack the hand strength that is necessary to fully actuate trigger (74) from the open position to the fired position. If the operator fails to fully actuate trigger (74) from the open position to the fired position, staples (66) may not fully form, and thus fail to fully secure an anastomosis. Therefore, it may be desirable to provide a trigger actuation assembly designed to require a reduced input force, as compared to the force required by trigger (74) to suitably actuate trigger carriage (86) via trigger arms (76) and tabs (88), to fire staple driver (250) and knife (240) in order to suitably form staples (66) in accordance with the description herein.

Various examples of how instrument (10) may be reconfigured to reduce the input force to suitably actuate trigger (74) will be described in greater detail below; while other examples will be apparent to those of ordinary skill in the art according to the teachings herein. It should be understood that the examples described below may function substantially similar to instrument (10) described above. In particular, the circular surgical stapling instruments described below may be used to staple tissue in an annular array and sever excess tissue that is interior to the annular array of staples to provide a substantially smooth transition between anastomosed lumen sections.

A. Exemplary Trigger Actuation Assemblies with Linkage Assemblies

Figure 11A:
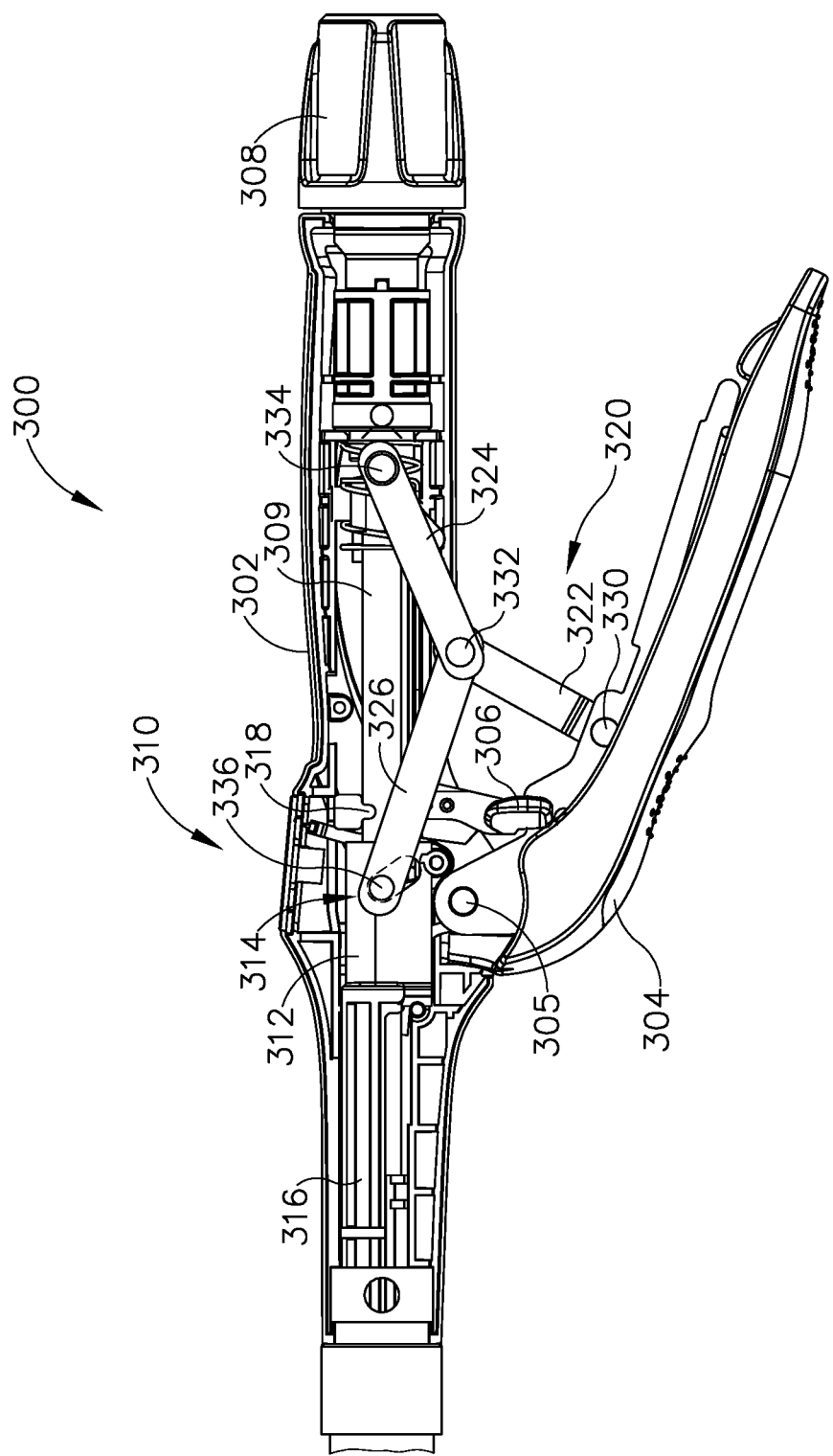
FIG. 11B depicts an elevational side view of the actuator handle assembly of FIG. 11A, with a portion of the body removed, showing the trigger in a partially fired position and the lockout feature in an unlocked position.
FIG. 11C depicts an elevational side view of the actuator handle assembly of FIG. 11A, with a portion of the body removed, showing the trigger in a fired position and the lockout feature in the unlocked position.
Figure 11B:
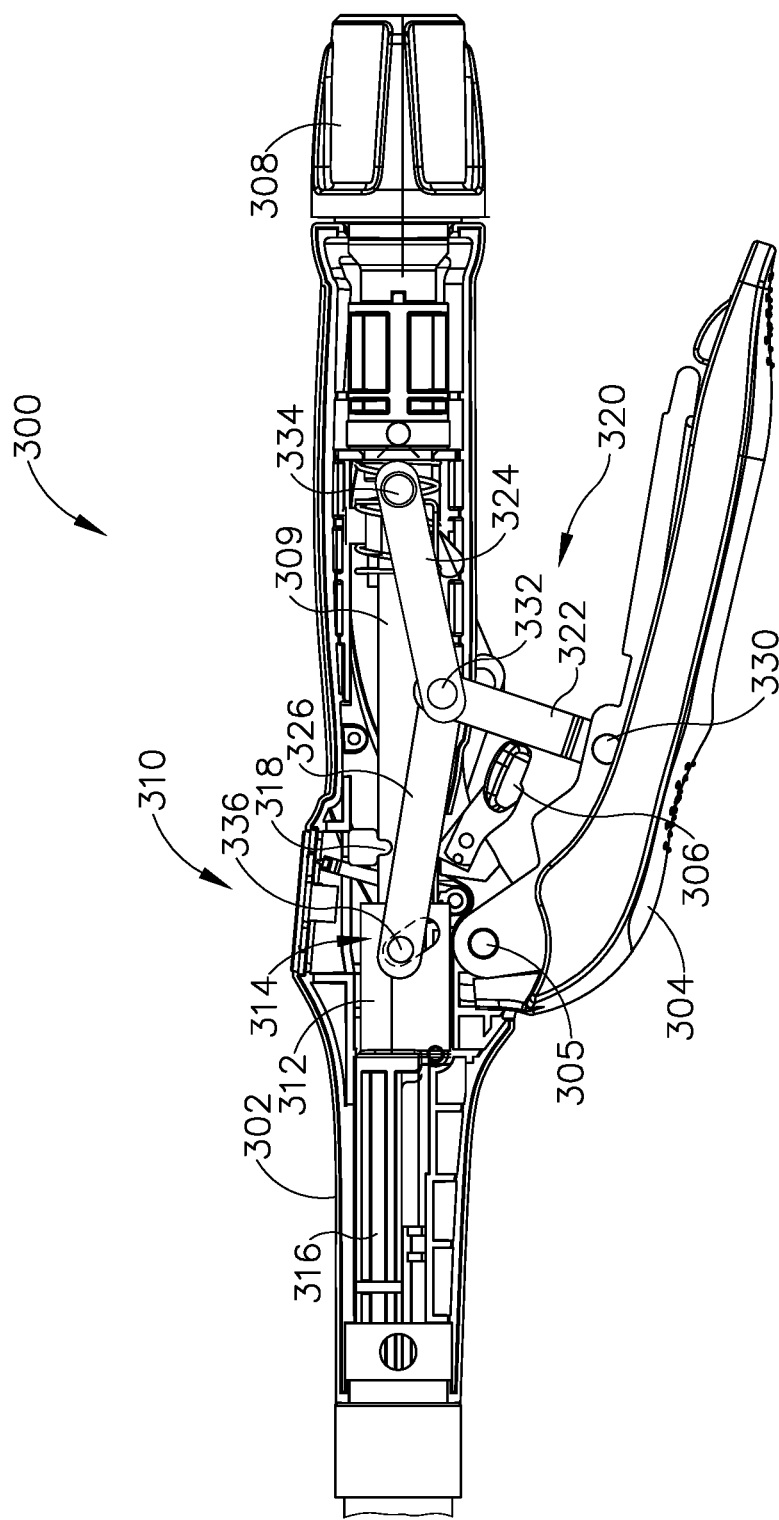
Figure 11C:
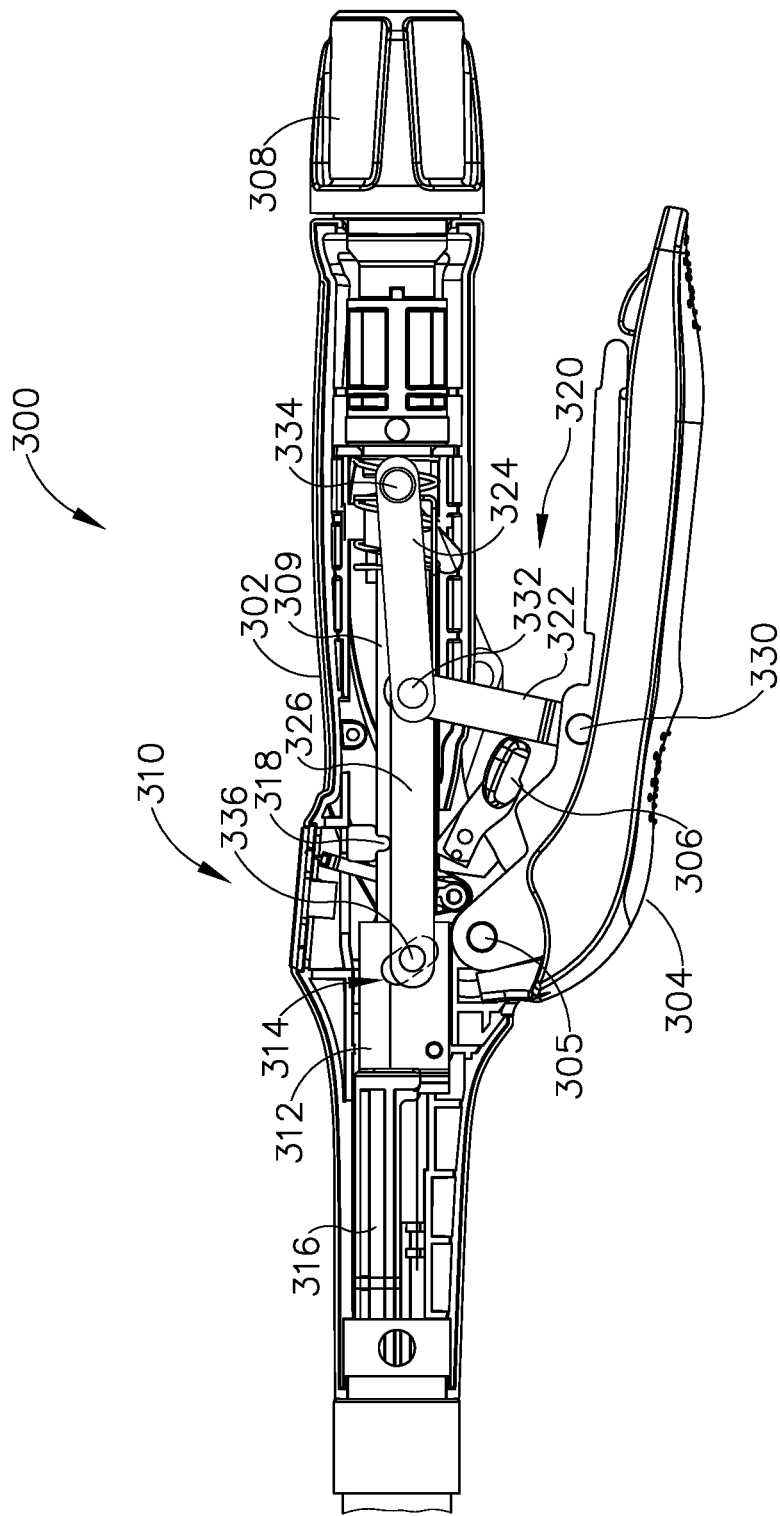

FIGS. 11A-11C show an exemplary alternative actuator handle assembly (300) that may be readily incorporated into instrument (10) described above. Actuator handle assembly (300) is substantially similar to actuator handle assembly (70) described above, with differences elaborated below. Therefore, if not explicitly shown or described, actuator handle assembly (300) may have the various features and functionality of actuator handle assembly (70) described above.

Actuator handle assembly (300) includes a body (302), a trigger (304), a lockout feature (306), an adjustment knob (308), and a trocar actuator (309); which are substantially similar to body (72), trigger (74), lockout feature (82), adjustment knob (98), and trocar actuator (231), described above, respectively, with differences elaborated below. Additionally, actuator handle assembly (300) includes an alternative trigger actuation assembly (310) configured to reduce the input force required to suitably actuate staple driver (250) and knife (240) in accordance with the description above to fully form staples (66).

Trigger actuation assembly (310) includes a slidable trigger carriage (312) and driver actuator (316); which are substantially similar to slidable trigger carriage (86) and driver actuator (64) described above, with differences elaborated below. Therefore, trigger carriage (312) is slidably housed within body (302), while driver actuator (316) is coupled to trigger carriage (312) on one end; and coupled to staple driver (250) and knife (240) on the other end. Trigger (304) is pivotably coupled to body (302) via a trigger pivot (305). Similar to trigger (74), trigger carriage (86), and driver actuator (64) described above, trigger (304) is operable to pivot relative to body (302) in order to translate trigger carriage (312) and driver actuator (316) to thereby actuate staple driver (250) and knife (240) in accordance with the description above. However, instead of trigger (304) driving trigger carriage (312) via tabs (88) and trigger arms (76), trigger actuation assembly (310) includes a linkage assembly (320) coupled between trigger (304) and trigger carriage (312) in order to suitably actuate carriage (312) in accordance with the description herein.

Linkage assembly (320) includes an input link (322), a body link (324), an actuating link (326), and a constraining body (318). Input link (322) is pivotably attached to trigger (304) via trigger pivot pin (330), body link (324) is pivotably attached to body (302) via body connecting pin (334), and actuating link (326) is slidably and pivotably connected to trigger carriage (312) via carriage connecting pin (336) and a channel (314) defined by trigger carriage (312). Input link (322), body link (324) and actuating link (326) are all pivotably connected to each other via a connecting pin (332). Connecting pin (332) is configured to actuate relative to body (302) when trigger (304) is actuating in accordance with the description herein. Because connecting pin (332) is attached to all three of input link (322), body link (324), and actuating link (326), connecting pin (332) has a range of motion determined by the links (322, 324, 326).

When the operator is ready to fire knife (240) and staple driver (250) in accordance with the description above, the operator may pivot locking feature (306) to the unlocked position such that trigger (304) may be pivoted relative to body (302). Next, as shown between FIGS. 11A-11B, the operator may pivot trigger (304) relative to body (302) through a first range of motion. During the first range of motion, input link (322) is configured to transfer forces from pivoting trigger (304) onto both actuating link (326) and body link (324) such that links (326, 324) rotate about pins (336, 334), respectively. As mentioned above, body link (324) is coupled to body (302) via body connecting pin (334). Body link (324) helps constrain and define the motion of input link (322) and actuating link (326) during the first range of motion as shown in FIGS. 11B-11A. In other words, body link (324) helps ensure both input link (322) and actuating link (326) consistently follow the same motion when the operator pivots trigger (304) about trigger pivot (305).

Because connecting pin (334) motion is constrained by body link (324), rotation of actuating link (326) relative to connecting pin (332) during the first range of motion causes actuating link (326) to drive carriage (312) distally via contact between carriage connecting pin (336) and channel (314). During the first range of motion, carriage (312) and driver actuator (316) may actuate distally in order to initially sever tissue and fire staples (66) against anvil (40) in accordance with the description above. Of course, carriage (312) and driver actuator (316) may be distally actuated any other suitable distance as would be apparent to one of ordinary skill in the art in view of the teachings herein.

Next, the operator may further pivot trigger (304) through a second range of motion as shown in FIGS. 11B-11C in order to actuate carriage (312) and driver actuator (316) further in the distal direction such that the firing of knife (240) and staple driver (250) is completed to suitably sever tissue and suitably compress staples (66) in accordance with the description herein. As will be described in greater detail below, linkage assembly (320) provides for mechanical advantage to reduce the force required to complete the firing stroke in accordance with the description herein. At the end of the firing stroke, knife (240) may be configured to break a washer housed within annular recess (56) in order to tactilely and/or audibly confirm completion of the firing process. While optional, this may also increase the force required to complete the firing stroke.

Once the operator pivots trigger (304) far enough such that linkage assembly (320) reaches the position shown in FIG. 11B, actuating link (326) rotates into contact within constraining body (318). Constraining body (318) is fixed relative to body (302). Therefore, when constraining body (318) abuts against actuating link (326), constraining body (318) prevents actuating link (326) from over-rotating (in the counter-clockwise direction) about carriage connecting pin (336) above constraining body (318).

Over-rotation of actuating link (326) about carriage connecting pin (336) above constraining body (318) may allow connecting pin (336) to proximally translate relative to channel (314) without also distally actuating carriage (312) relative to body (302). In other words, over-rotation of actuating link (326) above constraining body (318) may allow for movement of connecting pin (336) that fails to actuate carriage (312) relative to body (302).

As shown between FIGS. 11B-11C, because constraining body (318) prevents over-rotation of actuating link (326) about carriage connecting pin (336), connecting pin (336) and actuating link (326) may drive carriage (312) distally during the second range of motion. In particular, as connecting pin (332) is actuated by input link (322) about the path defined by body link (324), constraining body (318) contacts actuating link (326) such that movement of link (326) caused by actuation of connecting pin (332) is transferred into linear motion of carriage connecting pin (336) in the direction aligned with carriage (312) suitably firing knife (240) and staple driver (250). Additionally, linkage assembly (320) increases the mechanical advantage to complete the firing stroke, thereby reducing the input force required to suitably staple and sever tissue captured between anvil (40) and staple head assembly (200).

Once the firing stroke is complete, the operator may release trigger (304) or pivot trigger (304) away from body (302). Trigger (304) may be biased to the position shown in FIG. 11A such that linkage assembly (320) actuates knife (240) and staple driver (250) proximally in accordance with the description herein.

Figure 12A:
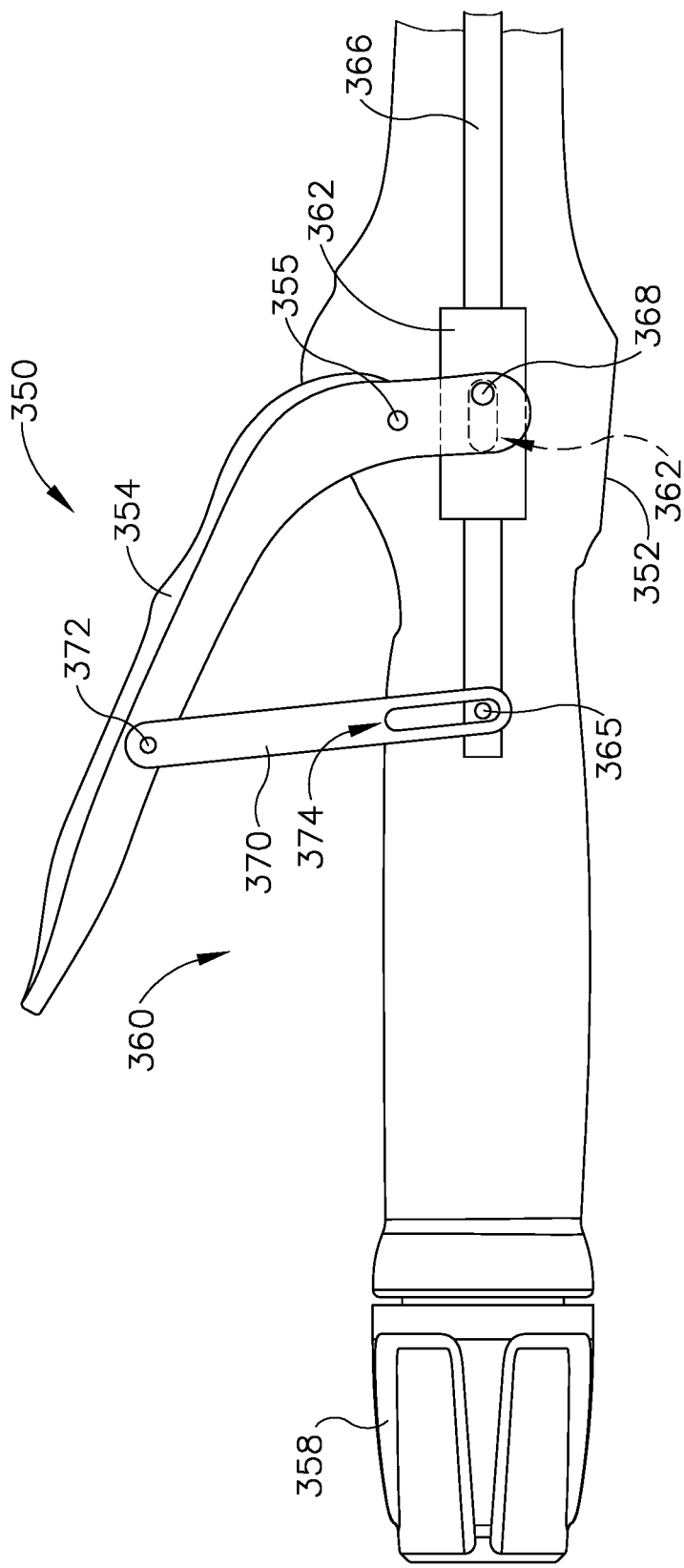
FIG. 12A depicts an elevational side view of an alternative actuator handle assembly that may be readily incorporated into the surgical instrument of FIG. 1, with a portion of the body removed, showing a trigger in an unfired position.
Figure 12B:
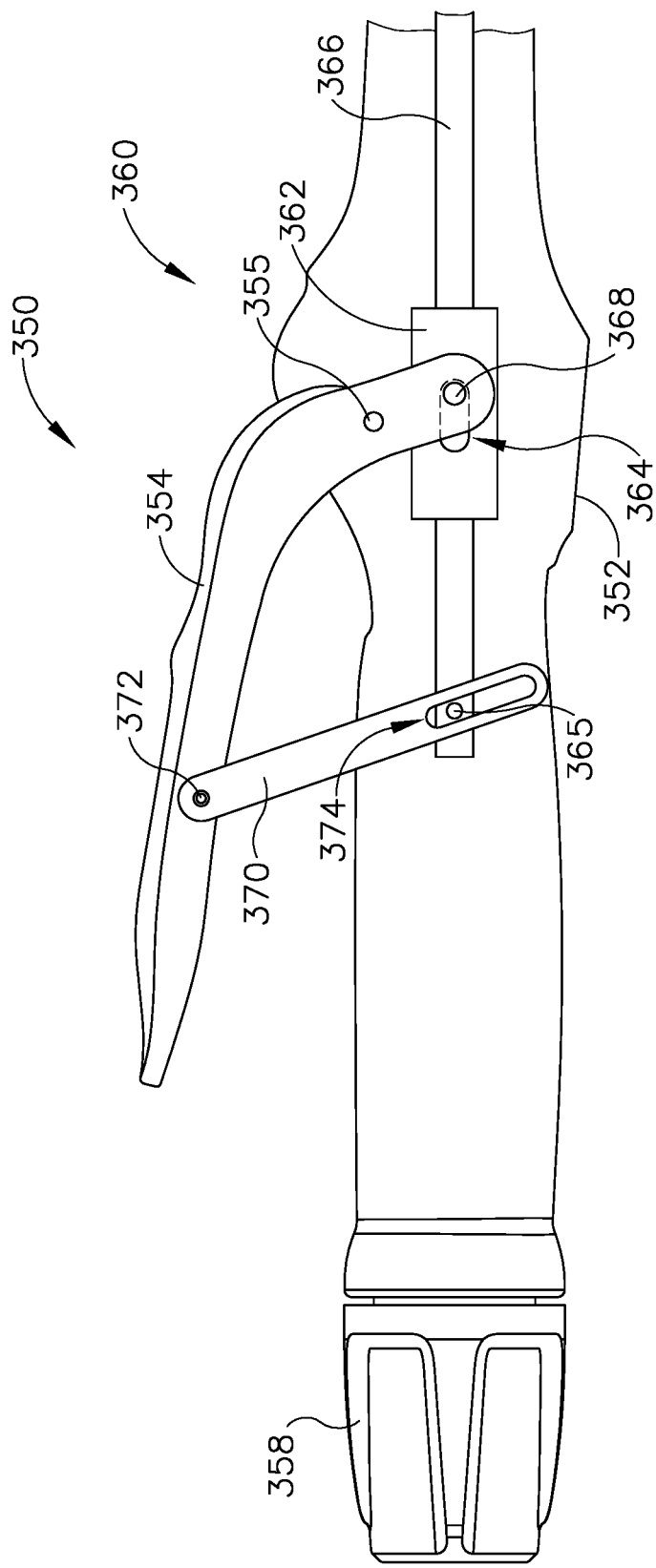
FIG. 12B depicts an elevational side view of the actuator handle assembly of FIG. 12A, with a portion of the body removed, showing the trigger in a partially fired position.
Figure 12C:
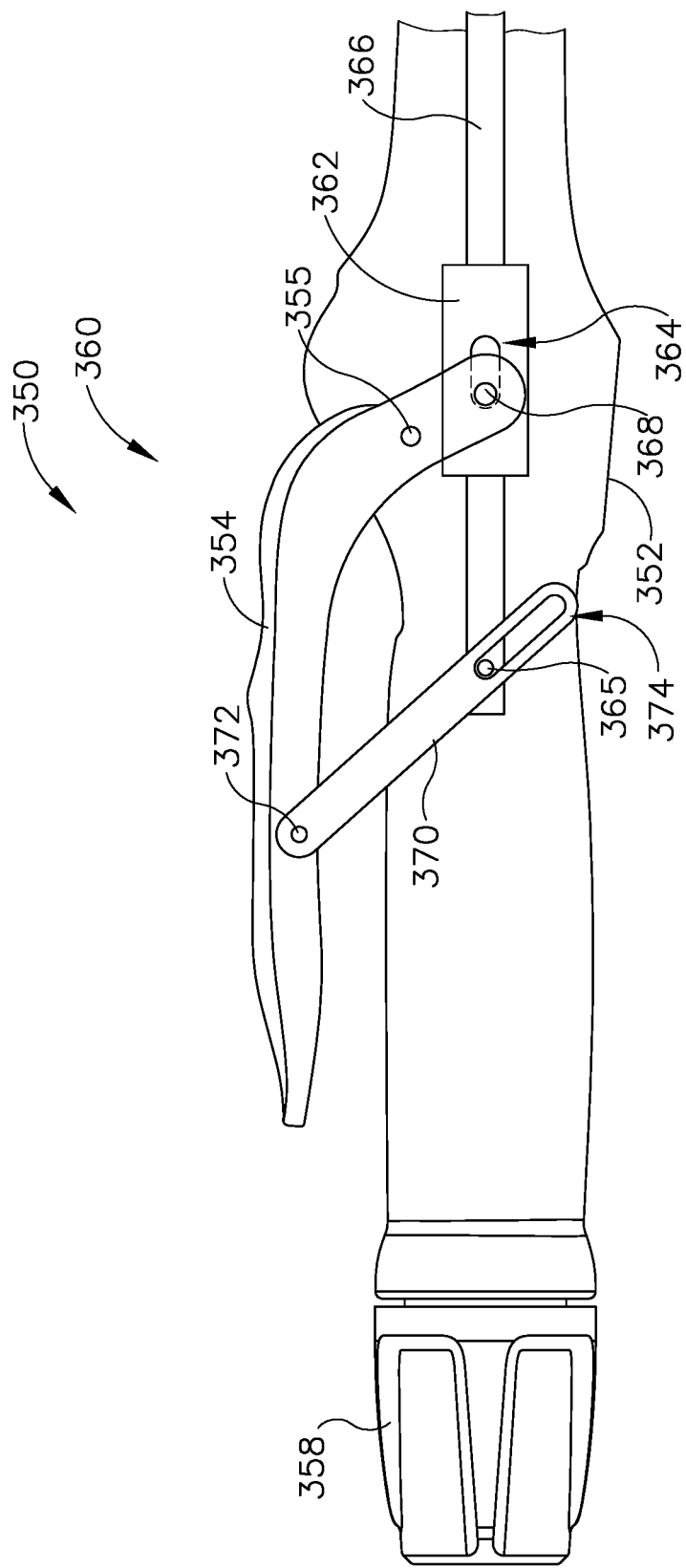
FIG. 12C depicts an elevational side view of the actuator handle assembly of FIG. 12A, with a portion of the body removed, showing the trigger in a fired position.

FIGS. 12A-12C show an exemplary alternative actuator handle assembly (350) that may be readily incorporated into instrument (10) described above. Actuator handle assembly (350) is substantially similar to actuator handle assembly (70) described above, with differences elaborated below. Therefore, if not explicitly shown or described, actuator handle assembly (350) may have the various features and functionality of actuator handle assembly (70) described above.

Actuator handle assembly (350) includes a body (352), a trigger (354), and an adjustment knob (358); which are substantially similar to body (72), trigger (74), and adjustment knob (98), described above, respectively, with differences elaborated below. Additionally, actuator handle assembly (350) includes an alternative trigger actuation assembly (360) configured to reduce the input force required to suitably actuate staple driver (250), and knife (240) in accordance with the description above to fully form staples (66).

Trigger actuation assembly (360) includes a slidable trigger carriage (362) and driver actuator (366); which are substantially similar to slidable trigger carriage (86) and driver actuator (64) described above, with differences elaborated below. Therefore, trigger carriage (362) is slidably housed within body (352); while driver actuator (366) is coupled to trigger carriage (362) on one end and coupled to staple driver (250) and knife (240) on the other end. Trigger (354) is pivotably coupled to body (352) via a trigger pivot (355). Similar to trigger (74), trigger carriage (86), and driver actuator (64) described above, trigger (354) is operable to pivot relative to body (352) in order to translate trigger carriage (362) and driver actuator (366) to thereby actuate staple driver (250) and knife (240) in accordance with the description above. However, instead of trigger (354) driving trigger carriage (362) via tabs (88) and trigger arms (76), trigger actuation assembly (360) includes a trigger pin (368) and a driving link (370) coupled with trigger (354) in order to actuate carriage (362) and driver actuator (366) distally.

Trigger pin (368) is attached to trigger (354) and is slidably housed within a channel (364) defined by carriage (362). As will be described in greater detail below, trigger pin (368) is configured to abut against a distal end of channel (364) in order to drive carriage (362) distally during a first range of motion (as shown between FIGS. 12A-12B). Driving link (370) is pivotably connected to trigger (354) via a pivotable coupling (372). Additionally, driving link (370) defines an elongated slot (374) that slidably houses a carriage pin (365). Carriage pin (365) is relative to carriage (362). Carriage pin (365) is slidably housed within slot (374). Additionally, driving link (370) is configured to rotate about carriage pin (365). As will be described in greater detail below, a proximal end of slot (374) is configured to abut against carriage pin (365) during a second range of motion such that driving link (370) may actuate carriage (362) distally.

As shown between FIGS. 12A-12B, when the operator is ready to fire knife (240) and staple driver (250) in accordance with the description above, the operator may pivot trigger (354) relative to body (352) about trigger pivot (355) through a first range of motion. During the first range of motion, trigger pin (368) abuts against a distal end of carriage channel (364) such that as trigger (354) pivots in the first range of motion, trigger pin (368) drives carriage (362) distally. Carriage (362) and driver actuator (366) may actuate distally in order to initially sever tissue and fire staples (66) against anvil (40) in accordance with the description above. Of course, carriage (362) and driver actuator (366) may be distally actuated any other suitable distance as would be apparent to one of ordinary skill in the art in view of the teachings herein.

It should be understood that during the first range of motion, driving link (370) rotates relative to carriage pin (365), while carriage pin (365) translates within slot (374) from a distal end of slot (374) to a proximal end of slot (374). Thus, driving link (370) does not assist in distally driving carriage (362) during the first range of motion.

Next, the operator may further pivot trigger (354) through a second range of motion as shown in FIGS. 12B-12C in order to actuate carriage (362) and driver actuator (366) further in the distal direction such that the firing of knife (240) and staple driver (250) is completed to suitably sever tissue and suitably compress staples (66) in accordance with the description herein. Driving link (370) provides a mechanical advantage during the second range of motion thereby reducing the input force required to suitably staple and sever tissue captured between anvil (40) and staple head assembly (200). At the end of the firing stroke, knife (240) may be configured to break a washer housed within annular recess (56) in order to tactilely and/or audibly confirm completion of the firing process. While optional, this may also increase the force required to complete the firing stroke.

Once the operator pivots trigger (354) far enough such that driving link (370) reaches the position shown in FIG. 12B, carriage pin (365) abuts against a proximal end of slot (374). As the operator pivots trigger (354) through the second range of motion, the proximal end of slot (374) defined by driving link (370) engages carriage pin (365) such that driving link (370) actuates carriage (362) in the distal direction during the second range of motion. Additionally, trigger pin (368) disengages a distal end of carriage channel (364) such that trigger pin (368) no longer drives carriage (362). As trigger (354) pivots through the second range of motion, driving link (370) pivots about both coupling (372) and carriage pin (365). The engagement between driving link (370) and carriage pin (365) provides for a mechanical advantage during the second range of motion to complete the firing stroke, thereby reducing the input force required to suitably staple and sever tissue captured between anvil (40) and staple head assembly (200).

Once the firing stroke is complete, the operator may release trigger (354) or pivot trigger (354) away from body (352). Trigger (354) may be biased to the position shown in FIG. 12A such that driving link (370) and trigger pin (368) actuate knife (240) and staple driver (250) proximally in accordance with the description herein.

Figure 13A:
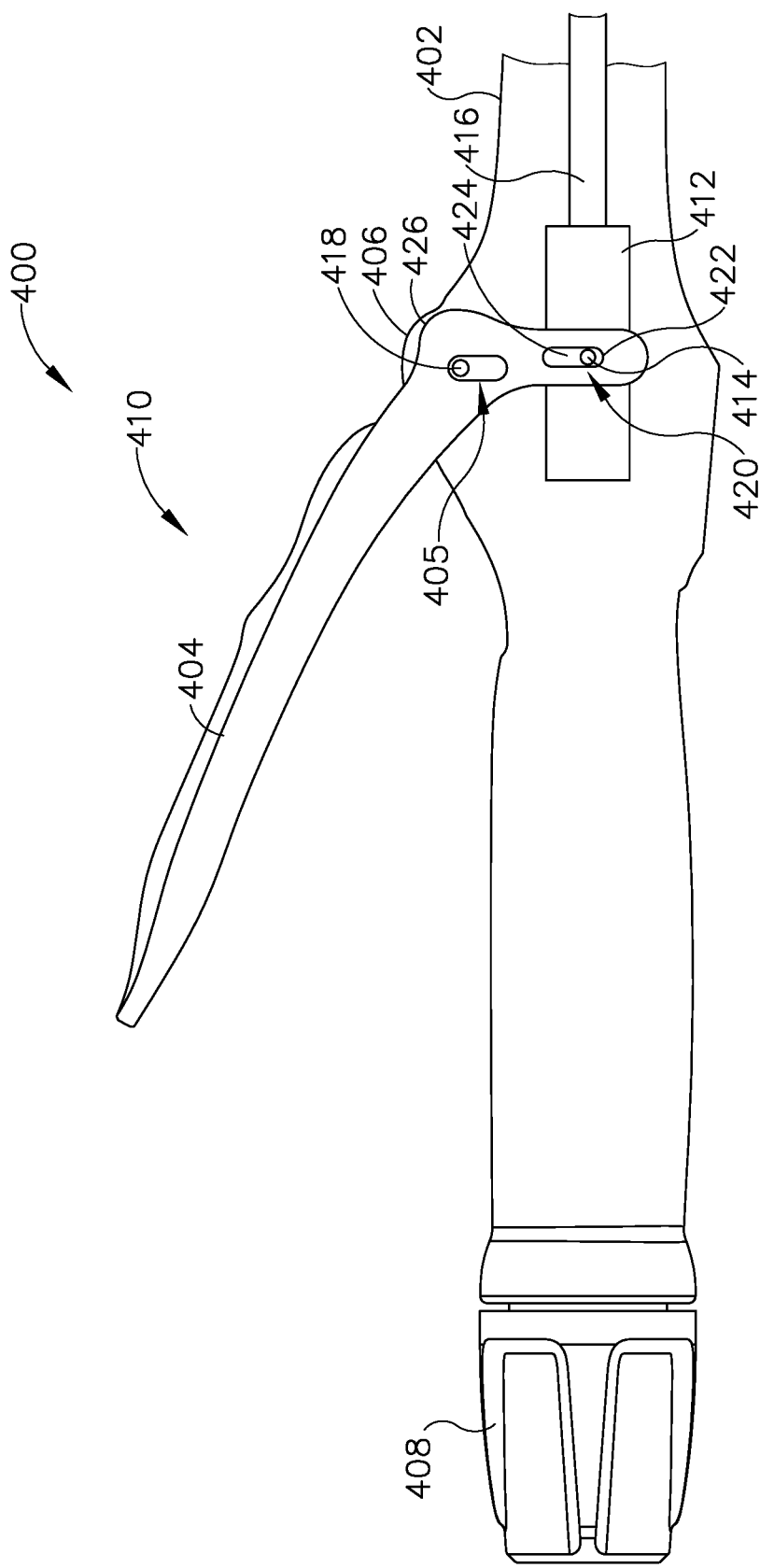
FIG. 13A depicts an elevational side view of an alternative actuator handle assembly that may be readily incorporated into the surgical instrument of FIG. 1, with a portion of the body removed, showing a trigger in an unfired position.
Figure 13B:
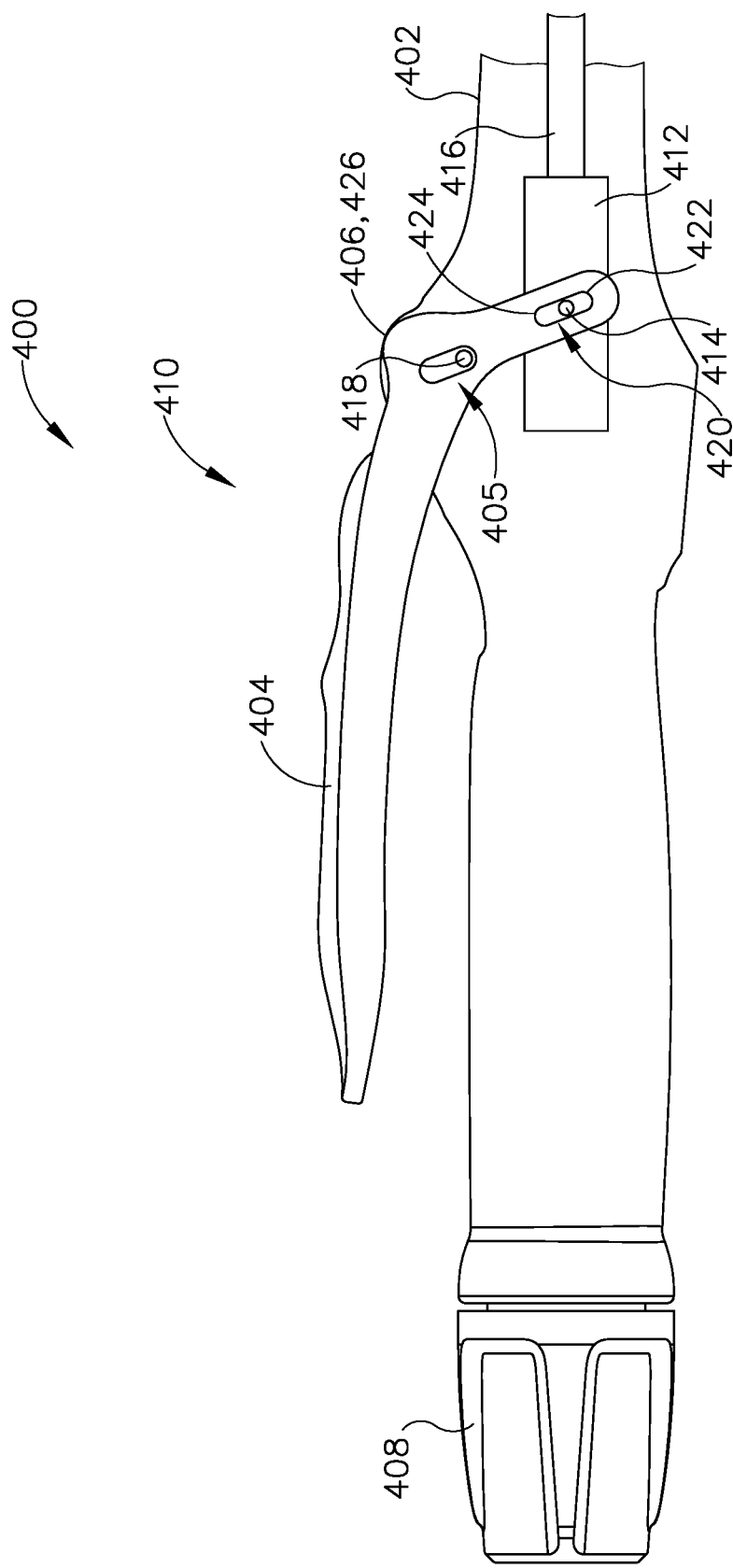
FIG. 13B depicts an elevational side view of the actuator handle assembly of FIG. 13A, with a portion of the body removed, showing the trigger in a fired position.

B. Exemplary Alternative Trigger Actuation Assembly with Variable Trigger Pivot FIGS. 13A-13B show an exemplary alternative actuator handle assembly (400) that may be readily incorporated into instrument (10) described above. Actuator handle assembly (400) is substantially similar to actuator handle assembly (70) described above, with differences elaborated below. Therefore, if not explicitly shown or described, actuator handle assembly (400) may have the various features and functionality of actuator handle assembly (70) described above.

Actuator handle assembly (400) includes a body (402), a trigger (404), and an adjustment knob (408); which are substantially similar to body (72), trigger (74), and adjustment knob (98), described above, respectively, with differences elaborated below. Additionally, actuator handle assembly (400) includes an alternative trigger actuation assembly (410) configured to reduce the input force required to suitably actuate staple driver (250), and knife (240) in accordance with the description above to fully form staples (66).

Trigger actuation assembly (410) includes a slidable trigger carriage (412) and driver actuator (416); which are substantially similar to slidable trigger carriage (86) and driver actuator (64) described above, with differences elaborated below. Therefore, trigger carriage (412) is slidably housed within body (402), while driver actuator (416) is coupled to trigger carriage (412) on one end and coupled to staple driver (250) and knife (240) on a distal end. Trigger (404) is pivotably coupled to body (402) via a variable trigger pivot (418) housed within a pivot slot (405) defined by body (402). Similar to trigger (74), trigger carriage (86), and driver actuator (64) described above, trigger (404) is operable to pivot relative to body (402) in order to translate trigger carriage (412) and driver actuator (416) to thereby actuate staple driver (250) and knife (240) in accordance with the description above. However, instead of trigger (404) driving trigger carriage (412) via tabs (88) and trigger arms (76), trigger (404) is coupled with carriage (412) via a trigger slot (420) and a pin (414) that help drive carriage (412). As will be described in greater detail below, as trigger (404) pivots toward body (402), the distance between variable trigger pivot (418) and pin (414) changes in order to increase the mechanical advantage of trigger (404) during the final stages of firing.

As mentioned above, carriage (412) includes a pin (414). Pin (414) is housed within a slot (420) defined by trigger (404). Trigger (404) is configured to drive carriage (412) via the interaction between slot (420) and pin (414) as trigger (404) pivots toward body (402). Slot (420) of trigger (404) extends from a distal end (422) to a proximal end (424). It should be understood that slot (420) of trigger (404) is fixed relative to variable pivot (418) of trigger (404).

As mentioned above, trigger (404) is pivotably coupled to body (402) via variable trigger pivot (418) housed within a pivot slot (405) defined by body (402). Additionally, trigger (404) includes a camming surface (426) while body (402) includes a corresponding camming surface (406). As shown between FIGS. 13A-13B, camming surfaces (406, 426) are configured to abut against each other while trigger (404) pivots toward body (402) in order to actuate trigger (404) laterally toward the center of body (402). In other words, camming surfaces (406, 426) abut against each other in order to drive variable trigger pivot (418) downwardly within pivot slot (405) defined by body (402).

Therefore, during exemplary use when the operator is ready to fire knife (240) and staple driver (250) in accordance with the description above, the operator may pivot trigger (404) relative to body (402). During the initial pivoting of trigger (404) relative to body (402), carriage pin (414) is within distal end (422) of trigger slot (420), and therefore a first distance away from variable trigger pivot (418). Trigger slot (420) still engages carriage pin (414) in order to distally actuate carriage (412) in accordance with the description herein. However, as trigger (404) is pivoted closer to body (402), camming surfaces (406, 426) engage each other to drive variable trigger pivot (418) downwardly within pivot slot (405). This, in turn, drives carriage pin (414) toward proximal end (424) of trigger slot (420). Therefore, interaction between camming surfaces (406, 426) drives variable trigger pivot (418) closer to carriage pin (414), which in turn increase the mechanical advantage during firing of driver actuator (416).

Once the firing stroke is complete, the operator may release trigger (404) or pivot trigger (404) away from body (402). Trigger (404) may be biased to the position shown in FIG. 13A such that trigger slot (420) and carriage pin (414) actuate knife (240) and staple driver (250) proximally in accordance with the description herein.

C. Exemplary Alternative Trigger Actuation Assembly with Compound Gear

Figure 14A:
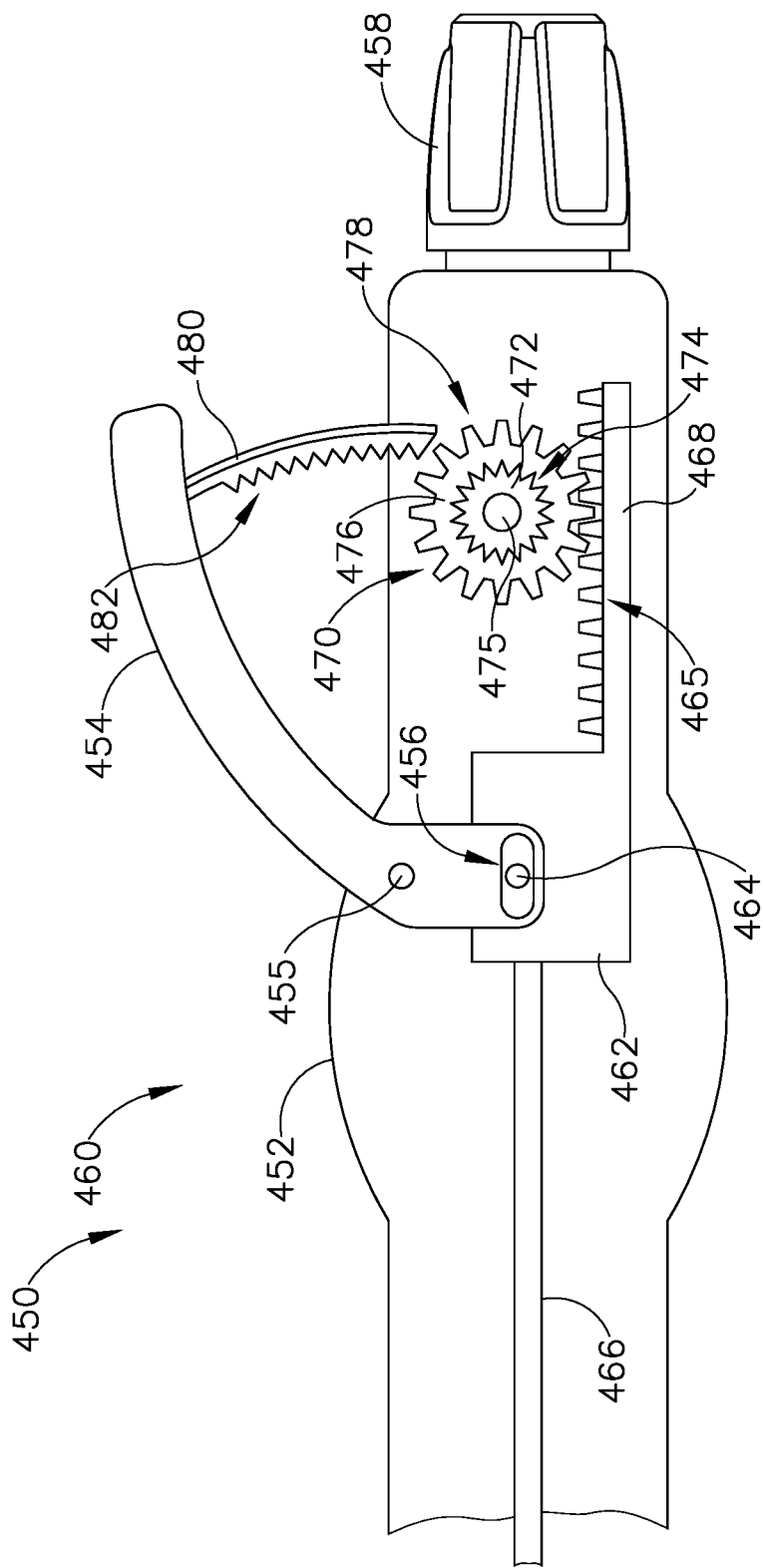
FIG. 14A depicts an elevational side view of an alternative actuator handle assembly that may be readily incorporated into the surgical instrument of FIG. 1, with a portion of the body removed, showing a trigger in an unfired position.
Figure 14B:
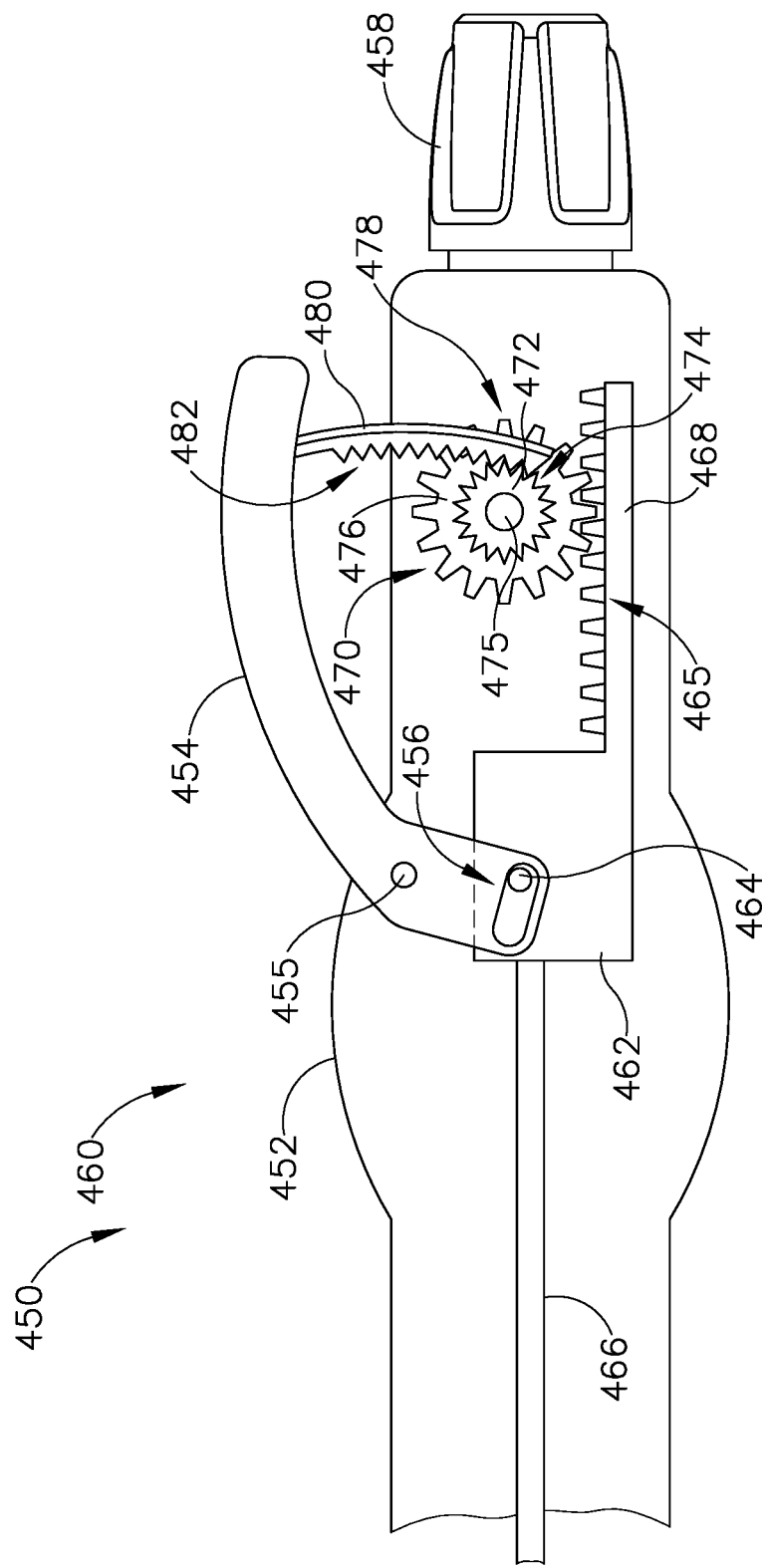
FIG. 14B depicts an elevational side view of the actuator handle assembly of FIG. 14A, with a portion of the body removed, showing the trigger in a fired position.

FIGS. 14A-14B show an exemplary alternative actuator handle assembly (450) that may be readily incorporated into instrument (10) described above. Actuator handle assembly (450) is substantially similar to actuator handle assembly (70) described above, with differences elaborated below. Therefore, if not explicitly shown or described, actuator handle assembly (450) may have the various features and functionality of actuator handle assembly (70) described above.

Actuator handle assembly (450) includes a body (452), a trigger (454), and an adjustment knob (458); which are substantially similar to body (72), trigger (74), and adjustment knob (98), described above, respectively, with differences elaborated below. Additionally, actuator handle assembly (450) includes an alternative trigger actuation assembly (460) configured to reduce the input force required to suitably actuate staple driver (250), and knife (240) in accordance with the description above to fully form staples (66).

Trigger actuation assembly (460) includes a slidable trigger carriage (462) and driver actuator (466); which are substantially similar to slidable trigger carriage (86) and driver actuator (64) described above, with differences elaborated below. Therefore, trigger carriage (462) is slidably housed within body (452), while driver actuator (466) is coupled to trigger carriage (462) on one end and coupled to staple driver (250) and knife (240) on a distal end. Trigger (454) is pivotably coupled to body (452) via a trigger pivot (455). Similar to trigger (74), trigger carriage (86), and driver actuator (64) described above, trigger (454) is operable to pivot relative to body (452) in order to translate trigger carriage (462) and driver actuator (466) to thereby actuate staple driver (250) and knife (240) in accordance with the description above. However, instead of trigger (454) driving trigger carriage (462) via tabs (88) and trigger arms (76), trigger actuation assembly (460) includes an input rack (480), a compound pinion gear (470), and proximally extending output rack (468) configured to provide a mechanical advantage to actuate trigger carriage (462) distally to complete a firing stroke.

Trigger (454) defines a slot (456) that houses a pin (464). Pin (464) is attached to trigger carriage (462) such that actuation of pin (464) leads to actuation of trigger carriage (462). Slot (456) may interact with pin (464) such that initially pivoting trigger (454) about trigger pivot (455) is configured to initially drive trigger carriage (462) distally.

As mentioned above, trigger actuation assembly (460) includes a compound pinion gear (470) and a proximally extending output rack (468). Compound pinion gear (470) is pivotably coupled with body (452) via pivot pin (475). Compound pinion gear (470) includes an input gear (472) having a plurality of input teeth (474), and an output gear (476) having a plurality of output teeth (478). Input gear (472) and output gear (476) are configured to rotate together about pivot pin (475). Input gear (472) has a smaller diameter than output gear (476), which allows compound pinion gear (470) to act as a torque amplifier in order to provide a mechanical advantage during the firing of carriage (462).

Trigger actuation assembly (460) includes input rack (480) connected to, and extending downwardly from, trigger (454). As shown in FIG. 14B, input rack (480) includes a plurality of teeth (482) configured to selectively mesh with teeth (474) of input gear (472). In particular, input rack (480) is configured to couple with input gear (472) as trigger (454) is pivoted toward body (452). When coupled with each other, input rack (480) is configured to rotate input gear (472), and therefore output gear (476), in response to pivoting of trigger (454). Pivoting trigger (454) toward body (452) causes rotation of input gear (472), and therefore rotation of output gear (476), in a first angular direction; while pivoting of trigger (454) away from body (452) causes rotation of input gear (472), and therefore rotation of outpour gear (476), in a second, opposite, angular direction.

Proximally extending output rack (468) is fixed relative to carriage (462) such that actuation of output rack (468) causes corresponding actuation of carriage (462). Output rack (468) is slidably coupled with body (452) such that output rack (468) may translate proximally and distally relative to body (452), but also such that output rack (468) is rotationally constrained relative to body (452). Proximally extending output rack (468) includes a plurality of teeth (465) dimensioned to mesh with teeth (478) of output gear (476). Therefore, rotation of output gear (476) causes translation of output rack (468). In particular, rotation of output gear (476) in the first angular direction drives translation of output rack (468) in a distal direction; while rotation of output gear (476) in the second, opposite, angular direction drives translation of output rack (468) in a proximal direction. Therefore, when input rack (480) is suitably meshed with input gear (472), pivoting trigger (454) toward body (452) causes output rack (468) to translate distally, while pivoting trigger (454) away from body (452) causes output rack (468) to translate proximally.

Because input gear (472) and output gear (476) have different diameters, but rotate together, output gear (476) has an amplified torque value compared to the input torque provided by the operator pivoting trigger (454). This amplified torque value creates a mechanical advantage that may reduce the amount of input force required for the operator to suitably actuate trigger carriage (462) in accordance with the description above.

It should be understood that input rack (480) may be dimensioned to couple with input gear (472) during any suitable portion of the firing stroke as would be apparent to one having ordinary skill in the art in view of the teachings herein. Before input gear (472) and input rack (480) couple, trigger (454) may actuate carriage (462) via pin (464) and slot (456), although this is merely optional.

Once the firing stroke is complete, the operator may release trigger (454) or pivot trigger (454) away from body (452). Trigger (454) may be biased to the position shown in FIG. 14A such that trigger actuation assembly (460) actuates knife (240) and staple driver (250) proximally in accordance with the description herein.

Figure 15:
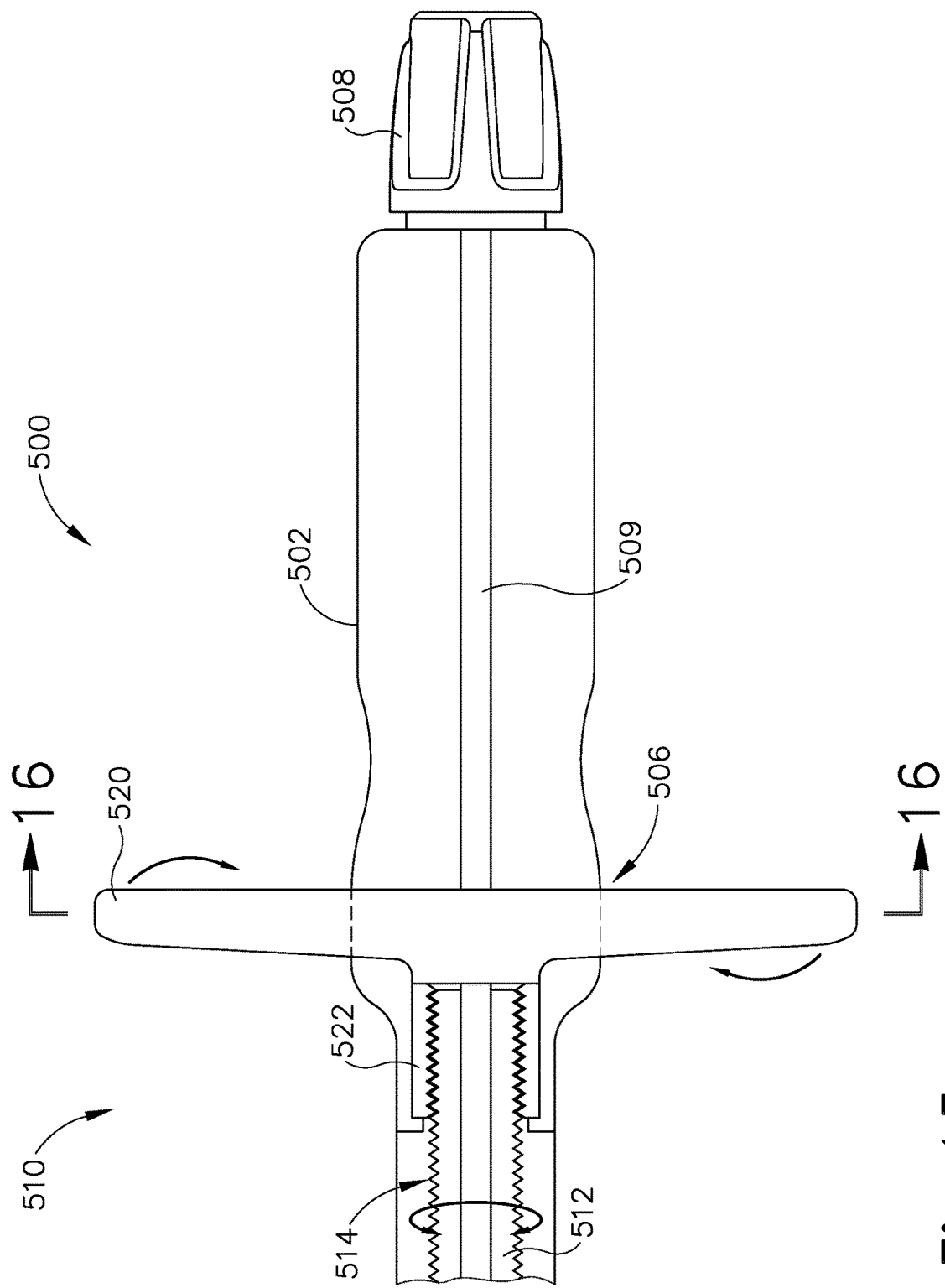
FIG. 15 depicts a cross-sectional side view of an alternative actuator handle assembly that may be readily incorporated into the surgical instrument of FIG. 1.
Figure 16:
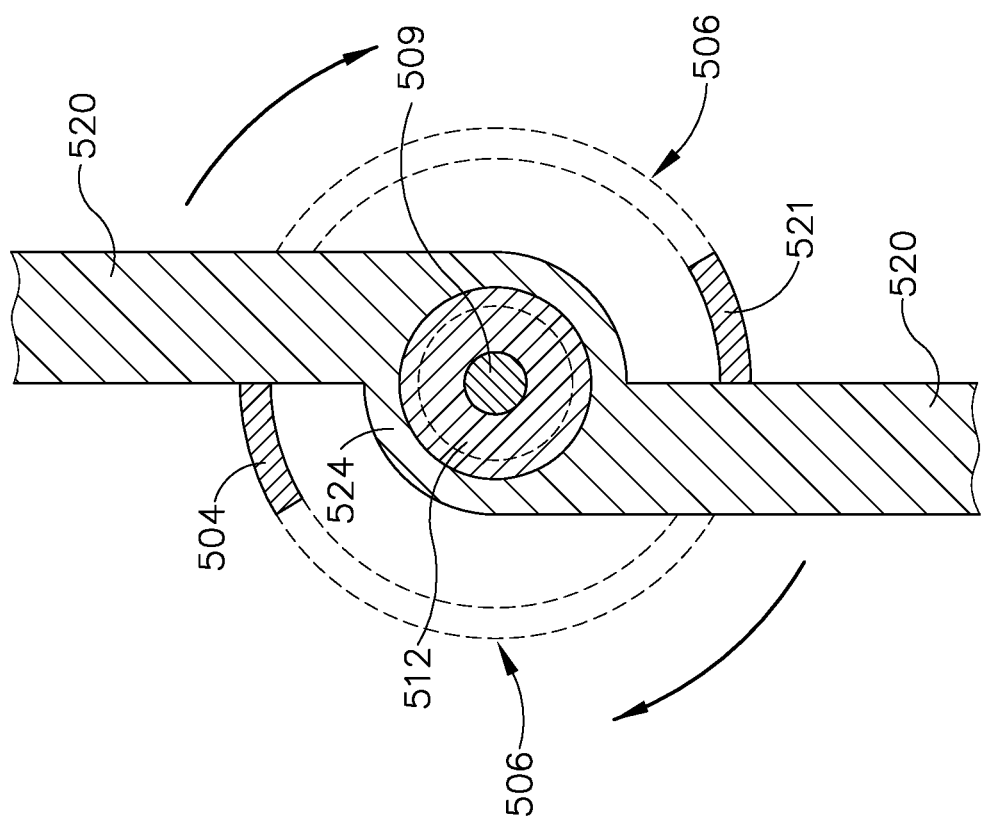
FIG. 16 depicts a cross-sectional view, taken along line 16-16 of FIG. 15, of the actuator handle assembly of FIG. 15.

D. Exemplary Alternative Trigger Actuation Assemblies with Rotating Drive Nut FIGS. 15-16 show an exemplary alternative actuator handle assembly (500) that may be readily incorporated into instrument (10) described above. Actuator handle assembly (500) is substantially similar to actuator handle assembly (70) described above, with differences elaborated below. Therefore, if not explicitly shown or described, actuator handle assembly (500) may have the various features and functionality of actuator handle assembly (70) described above.

Actuator handle assembly (500) includes a body (502), an adjustment knob (508), and trocar actuator (509); which are substantially similar to body (72), adjustment knob (98), and trocar actuator (231) described above, respectively, with differences elaborated below. Additionally, actuator handle assembly (500) includes an alternative firing assembly (510) configured to reduce the input force required to suitably actuate staple driver (250), and knife (240) in accordance with the description above to fully form staples (66).

Firing assembly (510) includes a translating carriage (512); which are substantially similar to slidable trigger carriage (86) described above. While not explicitly shown, it should be understood that carriage (512) is coupled with a driver actuator (not shown) which is substantially similar to driver actuator (64) described above. Therefore, carriage (512) is slidably housed within body (502), while driver actuator (not shown) is coupled to carriage (512) on one end and coupled to staple driver (250) and knife (240) on the other end. Carriage (512) is rotationally constrained relative to body (502) such that while carriage (512) may translate longitudinally relative to body (502), carriage (512) may not rotate about its own longitudinal axis relative to body (502). Additionally, carriage (512) include threading (514) that suitably meshes with threading of axially restrained driving nut (522). As will be described in greater detail below, carriage (512) is configured to translate in response to rotation of axially restrained driving nut (522) in order to fire staple driver (250) and knife (240) in accordance with the description above.

Firing assembly (510) also includes a rotating drive handle (520) rotatably disposed within body (502). Rotating drive handle (520) may rotate about the longitudinal axis of handle assembly (500) but may not otherwise translate relative to body (502). In particular, as best shown in FIG. 16, body (502) includes a pair of ribs (504) that define a rotating pathway (506). Additionally, rotating drive handle (520) defines a longitudinal through hole path to slidably receive trocar actuator (509) or any other suitable translating components as would be apparent to one having ordinary skill in the art in view of the teachings herein. Rotating drive handle (520) may rotate within rotating pathway (506) between ribs (504). Therefore, in the current example, rotating drive handle (520) may rotate about 180 degrees before contacting the opposing rib (504) defining pathway (506). While two ribs (504) are used in the current example, any other suitable number of ribs may be used as would be apparent to one having ordinary skill in the art in view of the teachings herein. For example, one rib (504), three ribs (504), or four ribs (504) may be used.

Rotating drive handle (520) is coupled with axially restrained driving nut (522) such that drive handle (520) and driving nut (522) rotate relative to body (502) together. Therefore, when the operator desires to actuate carriage (512), the operator may rotate handle (520) about the longitudinal axis of body (502) in a first angular direction in order to distally translate carriage (512) to fire knife (240) and staple driver (250). In particular, meshing of threads (514) and axial restrained nut (522) allow rotation of nut (522) to translate carriage (512) due to the fact that carriage (512) is rotationally constrained yet slidably coupled with body (502). Axially restrained nut (522) and threads (514) of translating carriage (512) may be dimensioned such that rotation of drive handle (520) from one rib (504) to the other rib (504) allows carriage (512) to fully actuate knife (240) and staple driver (250) to a fully fired position. Alternatively, the operator may rotate drive handle (520) about the longitudinal axis of body (502) in a second, opposite, angular direction in order to proximally translate carriage (512).

Rotating drive handle (520) has a pair of handles extending laterally away from body (502). Rotating drive handle (520) may extend away from body (502) any suitable distance in order to provide a mechanical advantage to reduce the amount of force required to rotate drive handle (520) in order to distally translate carriage (512) to suitably fire knife (240) and staple driver (250) in accordance with the description above.

Figure 17:
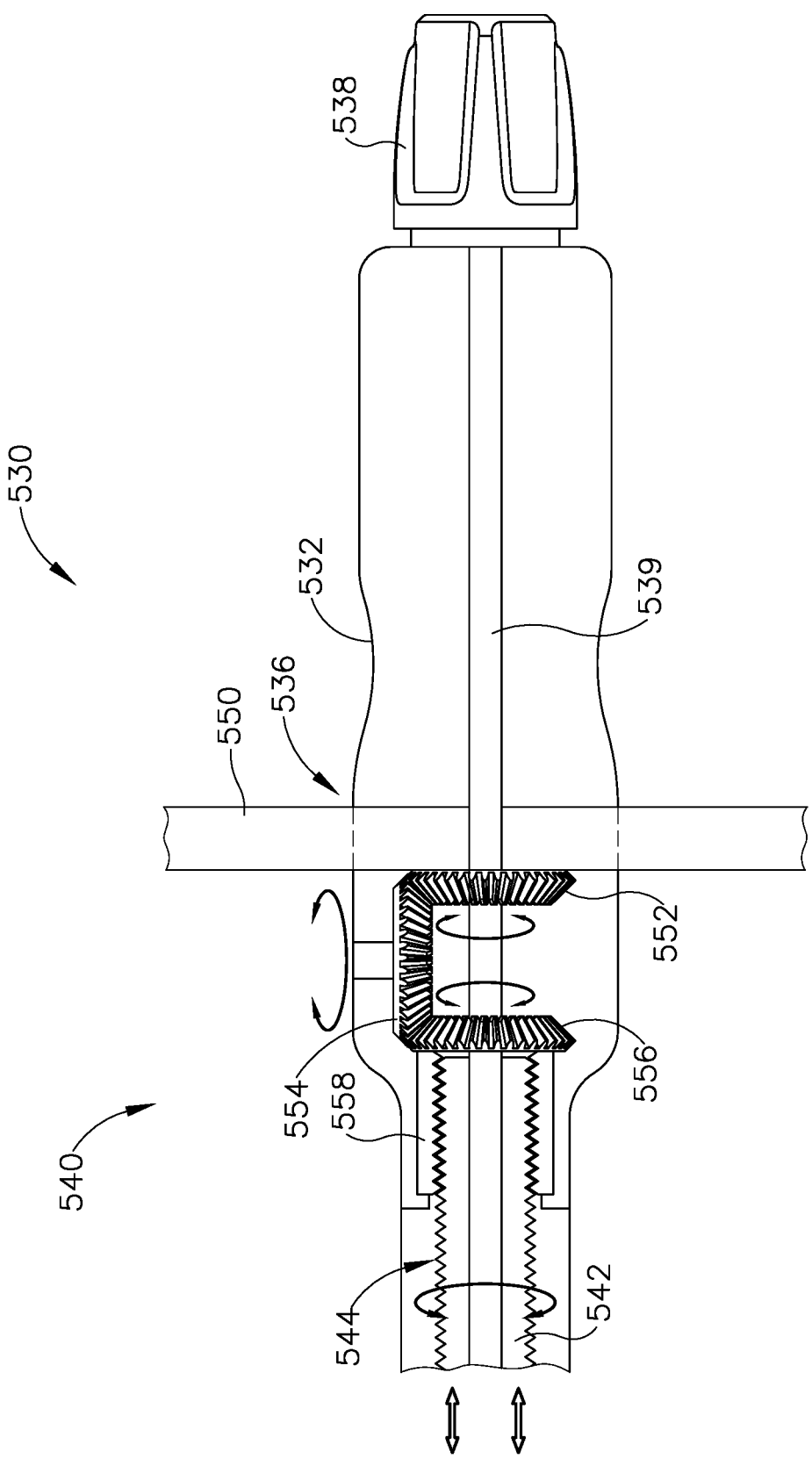
FIG. 17 depicts a cross-sectional side view of an alternative actuator handle assembly that may be readily incorporated into the surgical instrument of FIG. 1.

FIG. 17 shows an exemplary alternative actuator handle assembly (530) that may be readily incorporated into instrument (10) described above. Actuator handle assembly (530) is substantially similar to actuator handle assembly (70) described above, with differences elaborated below. Therefore, if not explicitly shown or described, actuator handle assembly (530) may have the various features and functionality of actuator handle assembly (70) described above.

Actuator handle assembly (530) includes a body (532), an adjustment knob (538), and trocar actuator (539); which are substantially similar to body (72), adjustment knob (98), and trocar actuator (231) described above, respectively, with differences elaborated below. Additionally, actuator handle assembly (530) includes an alternative firing assembly (540) configured to reduce the input force required to suitably actuate staple driver (250) and knife (240) in accordance with the description above to fully form staples (66).

Firing assembly (540) includes a translating carriage (542), which is substantially similar to slidable trigger carriage (86) described above. While not explicitly shown, it should be understood that slidable carriage (542) is coupled with a driver actuator (not shown), which is substantially similar to driver actuator (64) described above. Therefore, carriage (542) is slidably housed within body (532), while driver actuator (not shown) is coupled to carriage (542) on one end and coupled to staple driver (250) and knife (240) on the other end. Carriage (542) is rotationally constrained relative to body (532) such that while carriage (542) may translate longitudinally relative to body (532), carriage (542) may not rotate about its own longitudinal axis relative to body (532). Additionally, carriage (542) includes teeth (544) that suitably meshes with threading of axially restrained driving nut (558). As will be described in greater detail below, carriage (542) is configured to translate in response to rotation of axially restrained driving nut (558) in order to fire staple driver (250) and knife (240) in accordance with the description above.

Similar to firing assembly (510) described above, firing assembly (540) also includes a rotating drive handle (550) rotatably disposed within body (532). Therefore, rotating drive handle (550) may rotate about the longitudinal axis of handle assembly (530); but may not otherwise translate relative to body (532). In particular, similar to body (502) described above, body (532) includes a pair of ribs (not shown) that defines a rotating pathway (536). Additionally, rotating drive handle (550) defines a longitudinal through path to slidably receive trocar actuator (539) or any other suitable translating components as would be apparent to one having ordinary skill in the art in view of the teachings herein. Rotating drive handle (550) may rotate within rotating pathway (536) between ribs (not shown). Therefore, in the current example, rotating drive handle (550) may rotate about 180 degrees before contacting the opposing rib (not shown) defining pathway (506). While two ribs are used in the current example, any other suitable number of ribs may be used as would be apparent to one having ordinary skill in the art in view of the teachings herein. For example, one rib, three ribs, or four ribs may be used.

Unlike firing assembly (510) described above, rotating drive handle (550) is not directly coupled with axially restrained driving nut (558). Instead, axially restrained driving nut (558) is directly coupled to an output bevel gear (556), while rotating drive handle (550) is coupled with an input bevel gear (552). Bevel gears (552, 556) are coupled together via an intermediary bevel gear (554). Therefore, rotation of drive handle (550) in a first angular direction about the longitudinal axis of handle (530) causes rotation of input bevel gear (552) in the first angular direction about the longitudinal axis of handle (530), which in turn drives rotation of intermediary bevel gear (554) in a first angular direction about an axis perpendicular to the longitudinal axis of handle (530), which in turn drives output bevel gear (556) in a second, opposite, angular direction about the longitudinal axis of handle (530). Rotation of output bevel gear (556) in the second angular direction drives axially restrained driving nut (558) in the second angular direction. Rotation of axially restrained driving nut (558) in the second angular direction drives carriage (542) distally due to the meshing of driving nut (558) and teeth (544) of carriage (542). The operator may continue to rotate handle (550) to suitably fire knife (240) and staple driver (250) in accordance with the description above.

Alternatively, the operator may rotate handle (550) about the longitudinal axis of body (532) in the second, opposite, angular direction in order to proximally translate carriage (542) in accordance with the description herein.

Rotating drive handle (550) has a pair of handles extending laterally away from body (532). Rotating drive handle (550) may extend away from body (532) any suitable distance in order to provide a mechanical advantage to reduce the amount of force required to rotate drive handle (550) in order to distally translate carriage (542) to suitably fire knife (240) and staple driver (250) in accordance with the description above.

Figure 18:
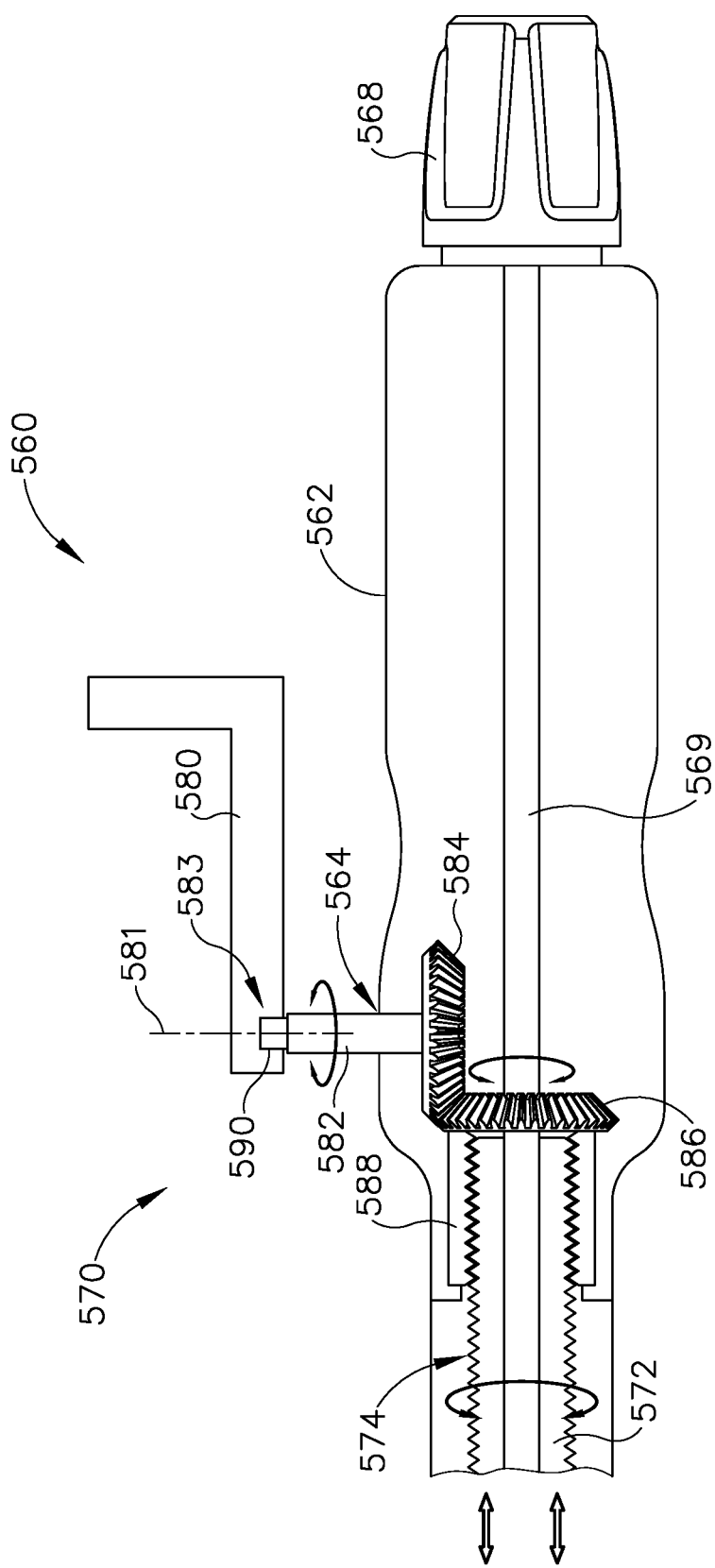
FIG. 18 depicts a cross-sectional side view of an alternative actuator handle assembly that may be readily incorporated into the surgical instrument of FIG. 1.
Figure 19:
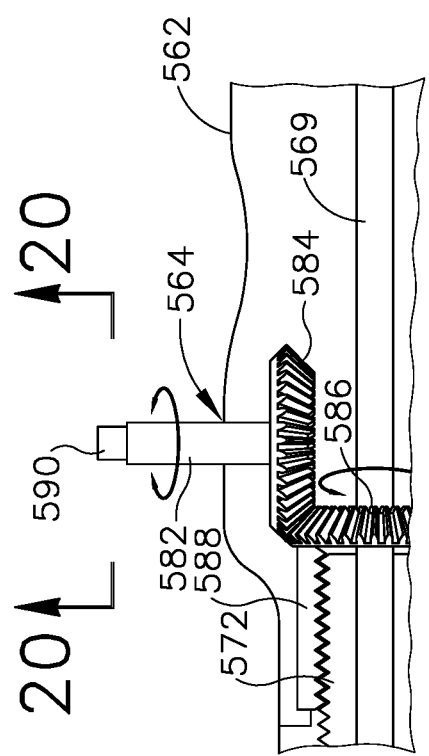
FIG. 19 depicts a cross-sectional side view of an input shaft and input bevel gear of the actuator handle assembly of FIG. 18.

FIG. 18 shows an exemplary alternative actuator handle assembly (560) that may be readily incorporated into instrument (10) described above. Actuator handle assembly (560) is substantially similar to actuator handle assembly (70) described above, with differences elaborated below. Therefore, if not explicitly shown or described, actuator handle assembly (560) may have the various features and functionality of actuator handle assembly (70) described above.

Actuator handle assembly (560) includes a body (562), an adjustment knob (568), and trocar actuator (569); which are substantially similar to body (72), adjustment knob (98), and trocar actuator (231) described above, respectively, with differences elaborated below. Additionally, actuator handle assembly (560) includes an alternative firing assembly (570) configured to reduce the input force required to suitably actuate staple driver (250) and knife (240) in accordance with the description above to fully form staples (66).

Firing assembly (570) includes a translating carriage (572); which is substantially similar to slidable carriage (86) described above. While not explicitly shown, is should be understood that translating carriage (572) is coupled with a driver actuator (not shown), which is substantially similar to driver actuator (64) described above. Therefore, carriage (572) is slidably housed within body (562), while driver actuator (not shown) is coupled to carriage (572) on one end and coupled to staple driver (250) and knife (240) on the other end. Carriage (572) is rotationally constrained relative to body (562) such that while carriage (572) may translate longitudinally relative to body (562), carriage (572) may not rotate about its own longitudinal axis relative to body (562). Additionally, carriage (572) include teeth (574) that suitably meshes with threading of axially restrained driving nut (588). As will be described in greater detail below, carriage (572) is configured to translate in response to rotation of axially restrained driving nut (588) in order to fire staple driver (250) and knife (240) in accordance with the description above.

Firing assembly (570) also includes a rotating driver handle (580), an input shaft (582), an input bevel gear (584), and an output bevel gear (586). Axially restrained driving nut (588) is directly coupled to output bevel gear (586) such that rotation of output bevel gear (586) drives rotation of axially restrained driving nut (588) in the same angular direction. Input bevel gear (584) suitably meshes with output bevel gear (586) such that rotation of input bevel gear (584) about an axis (581) perpendicular to the longitudinal axis of handle (560) drives rotation of output bevel gear (586) and axially restrained driving nut (588) about the longitudinal axis of handle (560).

Input bevel gear (584) is directly connected to input shaft (582) such that rotation of input shaft (582) about axis (581) drives rotation of input bevel gear (584) about axis (581) in the same angular direction. Input bevel gear (584) is rotatably housed within body (562) such that input bevel gear (584) may rotate about axis (581); but may not longitudinally translate relative to body (562). In some examples, as will be described in greater detail below, input bevel gear (584) and input shaft (582) may be configured to translate relative to body (562) along axis (581) in order to selectively disengage with output bevel gear (586). Input shaft (582) extends from input bevel gear (584), through an opening defined by body (562) and terminates in male coupling feature (590). Male coupling feature (590) is dimensioned to attach with a female coupling feature (583) of rotating driver handle (580) such that rotation of driver handle (580) about axis (581) also drives rotation of input shaft (582) about axis (581).

Rotation of handle (580) about axis (581) in a first angular direction rotates input shaft (582) and input bevel gear (584) in the first angular direction about axis (581). Input bevel gear (584) meshes with output bevel gear (586) in order to rotate output bevel gear (586) and axially restrained driving nut (588) in a first angular direction about the longitudinal axis of handle assembly (560). Rotation of axially restrained driving nut (588) in the first angular direction about the longitudinal axis of handle assembly (560) drives carriage (572) distally due to the meshing of driving nut (588) and teeth (574) of carriage (542). The operator may continue to rotate handle (580) about axis (581) to suitably fire knife (240) and staple driver (250) in accordance with the description above. When firing is complete, the operator may rotate handle (580) about axis (581) in a second, opposite, angular direction in order to proximally translate carriage (572) in accordance with the description herein.

Rotating drive handle (550) extends longitudinally away from axis (581) in order to provide a mechanical advantage for rotating input shaft (582) to reduce the amount of force required to distally translate carriage (572) to suitably fire knife (240) and staple driver (250) in accordance with the description above.

It should be understood that driver handle (580) may be either permanently affixed to input shaft (582) or configured to selectively couple with input shaft (582). In examples where input shaft (582) and rotating handle (580) are configured to selectively couple, coupling features (583, 590) may decouple and couple by actuating handle (580) along axis (581) when coupling features (583, 590) are suitably aligned. When suitably coupled, coupling features (583, 590) may permit actuating handle (580) to transfer torque to input shaft (582) such that handle (580) may suitably rotate input shaft (582) in accordance with the description herein. While in the current example input shaft (582) includes a male coupling feature (590) and handle (580) includes a female coupling feature (583), these features may be reversed such that handle (580) include a male coupling and input shaft (582) includes a female coupling.

Figure 22:
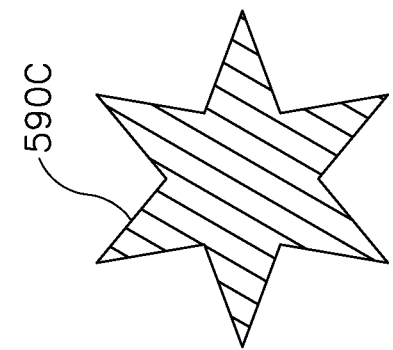
FIG. 22 depicts a cross-sectional view taken along line 20-20 of FIG. 19, of yet another exemplary male coupling of the input shaft.
Figure 21:
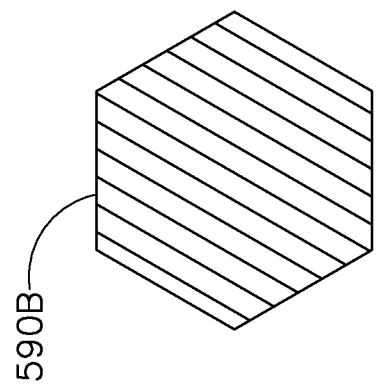
FIG. 21 depicts a cross-sectional view taken along line 20-20 of FIG. 19, of another exemplary male coupling of the input shaft.
Figure 20:
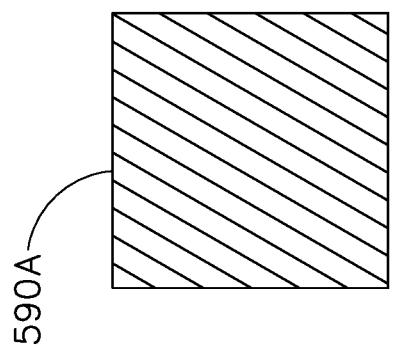
FIG. 20 depicts a cross-sectional view taken along line 20-20 of FIG. 19, of an exemplary male coupling of the input shaft.

FIGS. 20-22 show exemplary cross-sectional configurations of male coupling feature (590) that may be used in order to suitably transfer torque between handle (580) and input shaft (582). It should be understood that female coupling feature (583) may be dimensioned to correspond with the cross-section of male coupling features (590A, 590B, 590C). In FIG. 20, male coupling feature (590A) has a square cross-sectional shape. In FIG. 21, male coupling feature (590B) has a hexagonal cross-sectional shape. In FIG. 22, male couple feature (590C) has a star cross-sectional shape. Any other suitable cross-sectional shape for male coupling feature (590) may be used as would be apparent to one having ordinary skill in the art in view of the teachings herein.

Figure 24:
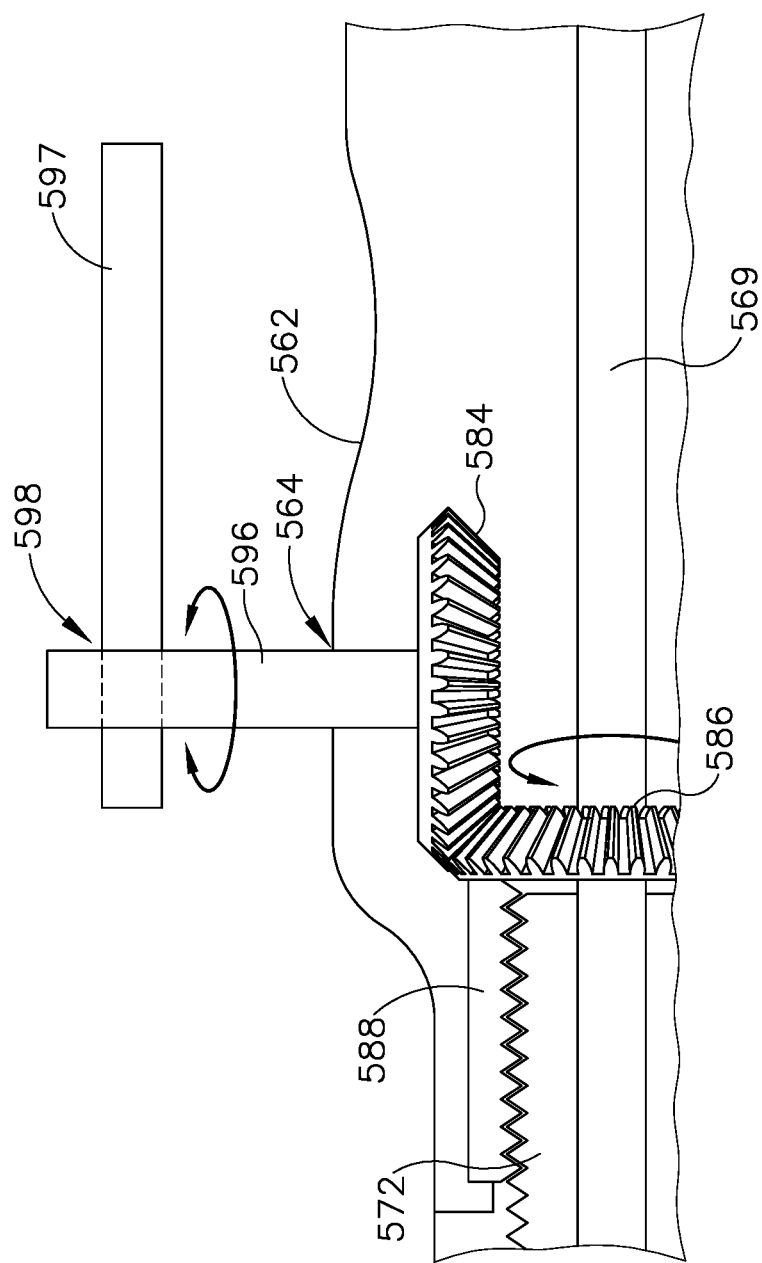
FIG. 24 depicts a cross-sectional side view of an alternative input shaft and the input bevel gear of the actuator handle assembly of FIG. 18, coupled with a rotating handle.

While a rotating handle (580) with a female coupling feature (583) may be used to rotate input shaft (582), other alternative rotational input devices be may be used as would be apparent to one having ordinary skill in the art in view of the teachings herein. For example, as shown in FIG. 23, a motor driven rotating body (585) having a female coupling (592) may be used to drive input shaft (582) about axis (581) in accordance with the description herein. Or, as shown in FIG. 24, an alternative input shaft (596) defining a through hole (598) that selectively receives a rotating bar (597) may be used.

As mentioned above, in some instances, input shaft (582) and input bevel gear (584) may be configured to actuate along axis (581). In particular, input shaft (582) and bevel gear (584) may be configured to actuate along axis (581) such that bevel gear (584) may selectively decouple with output bevel gear (586). Additionally, carriage (572) and or driving nut (588) may be biased in a proximal direction by a biasing element (579). In such instances, driving nut (588) may not be axially restrained, but may be able to actuate between a proximal position and a distal position. Therefore, after a firing process is complete, the operator may actuate input bevel gear (584) along axis (581) to disengage from output bevel gear (586) such that biasing element may actuate carriage (572) and nut (588) proximally to suitably return knife (240) and staple driver (250) to the pre-fired position without having to further rotate handle (580) about axis (581).

Figure 25:
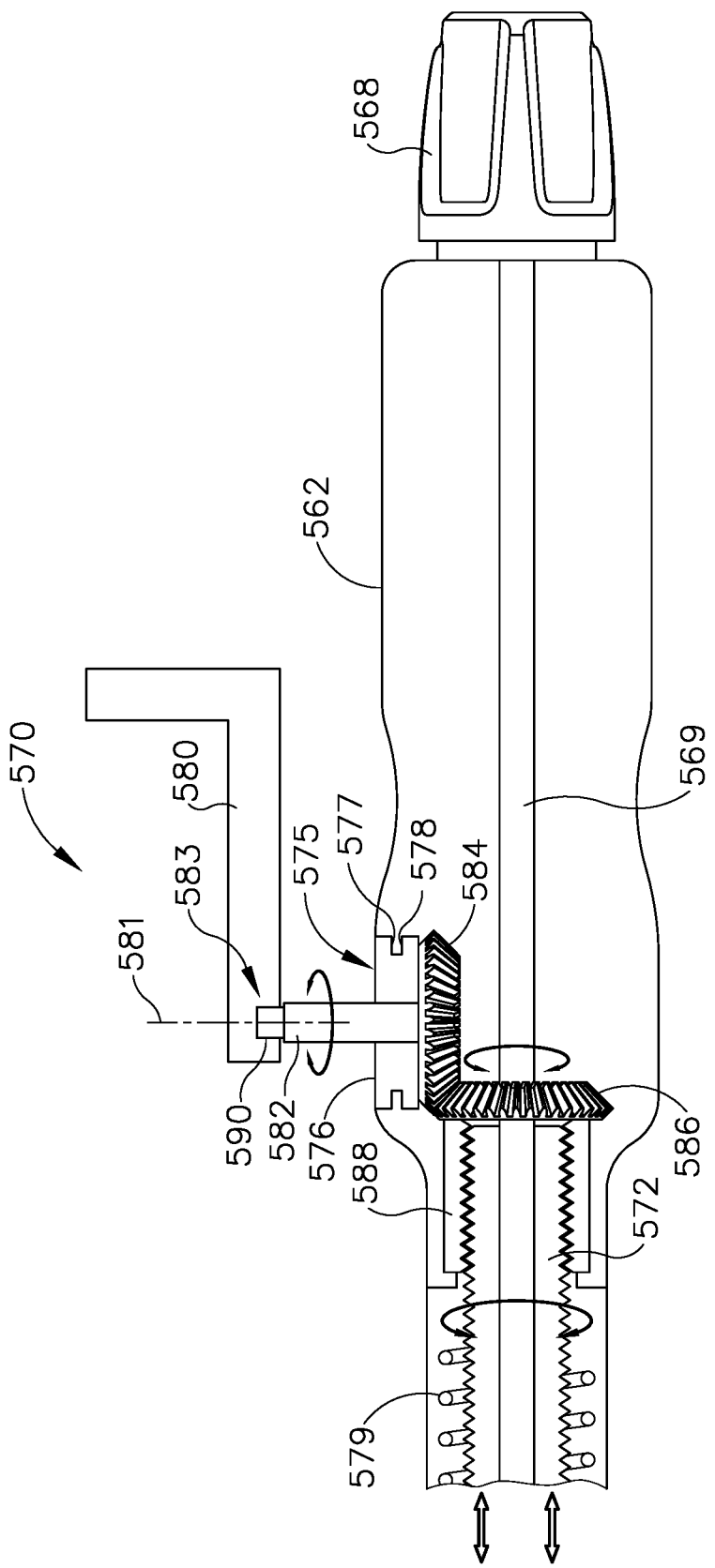
FIG. 25 depicts a cross-sectional side view of the actuator handle assembly of FIG. 18 with an additional resilient input bevel housing attached to the body.

In one example, as shown in FIG. 25, instead of body (562) defining an opening (564), body (562) includes a resilient input bevel housing (576) that houses input bevel gear (584) and a portion of input shaft (582). Resilient input bevel housing (576) includes a first shoulder (578) and a second shoulder (577). Additionally, bevel housing (576) and a portion of second shoulder (577) defines a disengaged pocket (575). Input bevel (584) is configured to abut against first shoulder (578) when input bevel (584) is engaged with output bevel (586). Therefore, the operator may rotate input shaft (582) in order to suitably actuate carriage (572) in accordance with the description above. After firing is complete, the operator may actuate input shaft (582) and input bevel gear (584) along axis (581) such that bevel gear (584) disengages output bevel gear (586). Input bevel gear (584) may flex resilient input bevel housing (576) such that a portion of bevel gear (584) is now within disengaged pocket (575) and abutting against second shoulder (577). Thus, biasing element (579) may actuate carriage (572) and driving nut (588) proximally such that knife (240) and staple driver (250) return to the pre-fired position. With input bevel gear (584) disengaged from output bevel gear (586), rotation of input shaft (582) may no longer actuate carriage (572).

E. Exemplary Alternative Trigger Actuation Assembly with Multi-Pumping Trigger

Figure 26:
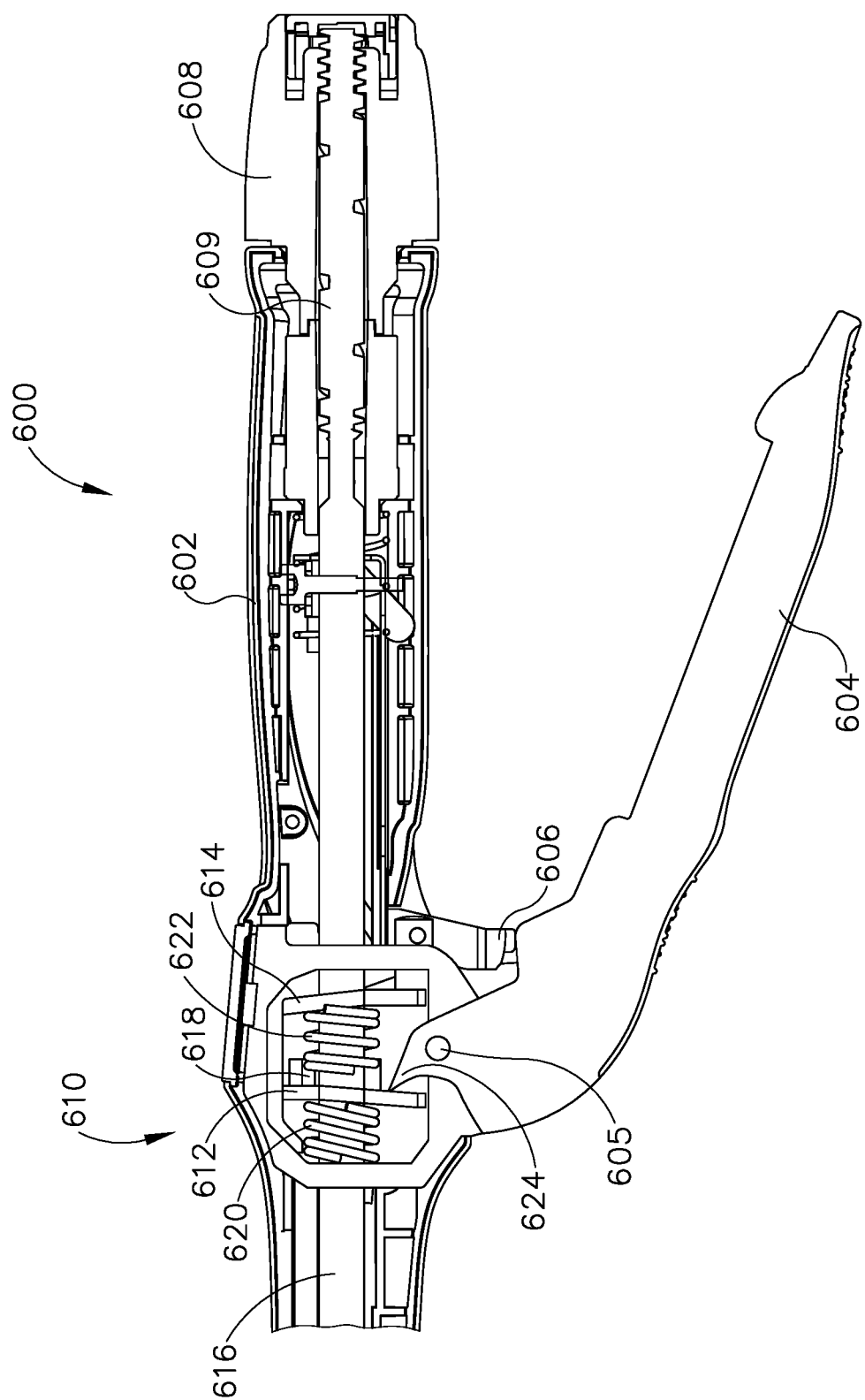
FIG. 26 depicts an elevational side view of an alternative actuator handle assembly that may be readily incorporated into the surgical instrument of FIG. 1, with a portion of the body removed.

FIG. 26 show an exemplary alternative actuator handle assembly (600) that may be readily incorporated into instrument (10) described above. Actuator handle assembly (600) is substantially similar to actuator handle assembly (70) described above, with differences elaborated below. Therefore, if not explicitly shown or described, actuator handle assembly (600) may have the various features and functionality of actuator handle assembly (70) described above.

Actuator handle assembly (600) includes a body (602), a trigger (604), a lockout feature (606), an adjustment knob (608), and a trocar actuator (609); which are substantially similar to body (72), trigger (74), lockout feature (82), adjustment knob (98), and trocar actuator (231), described above, respectively, with differences elaborated below. Trigger (604) is pivotably coupled with body (602) via pivot pin (605). Trigger (604) also includes a driving projection (624). Additionally, actuator handle assembly (600) includes an alternative trigger actuation assembly (610) configured to reduce the input force required to suitably actuate staple driver (250) and knife (240) in accordance with the description above to fully form staples (66).

Trigger actuation assembly (610) includes a driver actuator (616) that may be substantially similar to driver actuator (64) described above, with differences elaborated below. Additionally, trigger actuation assembly (610) includes a driving plate (612), a lock and release plate (614), a driving plate bias element (620), a locking plate bias element (622), and a release button (630). As will be described in greater detail below, trigger (604) may be pivoted toward and away from body (602) multiple times such that driving projection (624) incrementally actuates driving plate (612) and driver actuator (616) distally.

Figure 27:
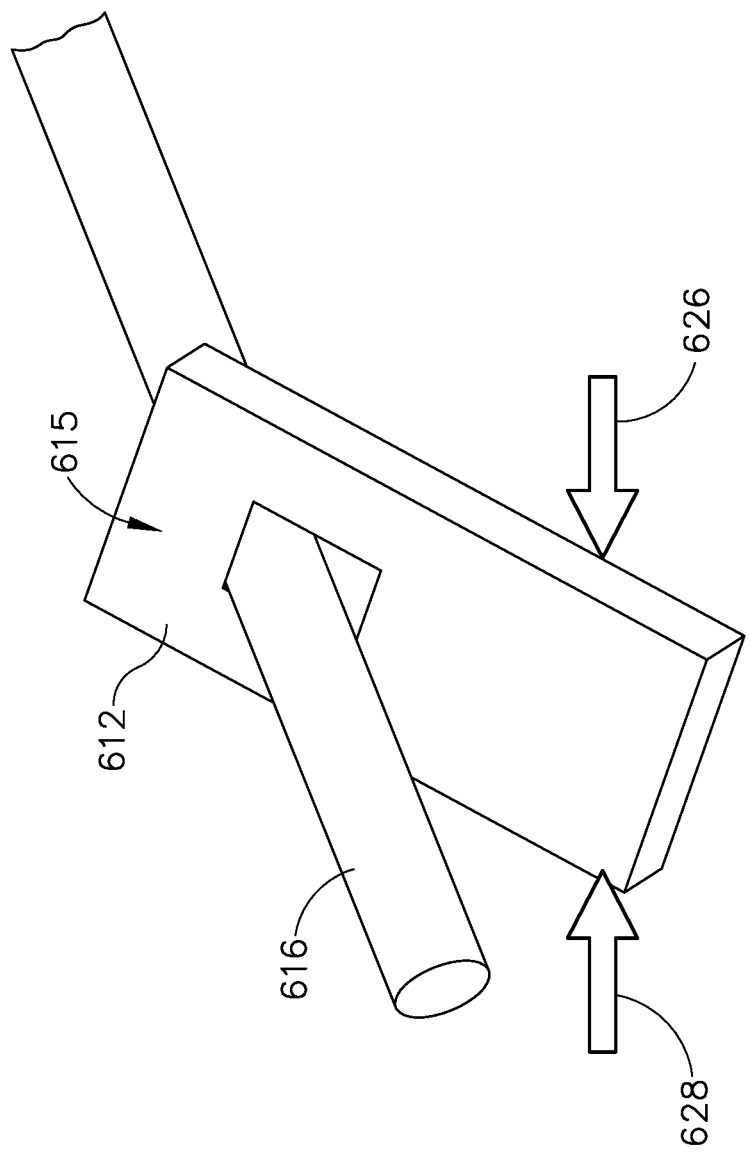
FIG. 27 depicts a perspective view of a driver actuator and a driving plate of the alternative actuator handle assembly of FIG. 26.

Driving plate (612) and lock and release plate (614) each define an opening (615) that receives driver actuator (616). As shown in FIG. 27, driving plate (612) may be actuated in a first direction (626) in order to grip driver actuator (616) and a second direction (628) in order to release driver actuator (616). It should be understood that lock and release plate (614) may also be actuated in a first direction to grip driver actuator (616) and in a second direction to release driver actuator (616).

Driving plate bias element (620), such as a spring, extends between driving plate (612) and body (602); while locking plate bias element (622), such as a spring, extends between ribs (618) of body (602) and lock and release plate (614). Driving plate bias element (620) biases driving plate (612) in a direction associated with plate (612) releasing engagement with driver actuator (616); while locking plate bias element (622) biases lock and release plate (614) in a direction associated with plate (614) gripping driver actuator (616).

When the operator desires to distally actuate driver actuator (616) in accordance with the description above, the operator may pivot trigger (604) such that driving projection (624) pushes driving plate (612) in the direction associated with driving plate (612) gripping driver actuator (616). Therefore, driving projection (624) overcomes the biasing force of biasing element (620) such that driving plate (612) grips driver actuator (616) and incrementally pushes driver actuator (616) distally. The force from driving plate (612) incrementally pushing driver actuator (616) distally is greater than the locking force of locking plate (614). The operator may release trigger (604) such that trigger (604) pivots away from body (602). Therefore, biasing element (620) pushes driving plate (612) back to the original position where driving plate (612) no longer grips driver actuator (616). It should be understood that lock and release plate (614) engages driver actuator (616) to maintain a longitudinal position of driver actuator (616) relative to body (602) when biasing element (620) pushes driving plate (612) proximally and when driving plate (612) is disengaged with driver actuator (616). The operator may again pivot trigger (604) toward body (602) to incrementally drive driver actuator (616) distally in accordance with the description above. The operator may repeat this process until knife (240) and staple driver (250) suitably actuate to sever and staple tissue. Therefore, the operator may be required to have reduced force to actuate trigger (604) toward body (602); and may instead pump trigger (604) multiple times toward and away from body (602) in order to incrementally fire driver actuator (616).

Once trigger (604) has been pivoted between the open and closed position enough times for knife (240) and staple driver (250) to suitably sever and staple tissue, the operator may push release button (630), which pushes lock and release plate (614) to the disengaged position by overcoming the biasing force of biasing element (622). With both plates (612, 614) in the disengaged position, knife (240) and staple driver (250) may actuate toward the proximal, pre-fired, position.

F. Exemplary Alternative Trigger Actuation Assembly with Hydraulic Force Multiplier FIG. 28 shows an exemplary alternative actuator handle assembly (650) that may be readily incorporated into instrument (10) described above. Actuator handle assembly (650) is substantially similar to actuator handle assembly (70) described above, with differences elaborated below. Therefore, if not explicitly shown or described, actuator handle assembly (650) may have the various features and functionality of actuator handle assembly (70) described above.

Actuator handle assembly (650) includes a body (652) which is substantially similar to body (72) described above, with differences elaborated below. While not explicitly shown, it should be understood actuator handle assembly (650) also includes a trigger, which is substantially similar to trigger (74) described above. Additionally, actuator handle assembly (650) includes an alternative trigger actuation assembly (660) configured to reduce the input force required to suitably actuate staple driver (250) and knife (240) in accordance with the description above to fully form staples (66). In particular, trigger actuation assembly (660) includes a hydraulic force multiplier assembly (570) interposed between the input force provided by a trigger and the output force actuating a driver actuator (666).

Trigger actuation assembly (660) includes a slidable trigger carriage (662), hydraulic force multiplier (670), and driver actuator (666). Slidably trigger carriage (662) may be substantially similar to trigger carriage (86) described above. Therefore, slidable trigger carriage (662) is configured to convert rotational motion/force of a trigger into translational motion/force. Driver actuator (666) may be substantially similar to driver actuator (64) described above. Therefore, driver actuator (666) may be connected at a distal end to knife (240) and staple driver (250) such that driver actuator (666) may communicate forces imparted on a proximal end of driver actuator (666) onto knife (240) and staple driver (250). Hydraulic force multiplier (670) is interposed between trigger carriage (662) and driver actuator (660). Hydraulic force multiplier (670) defines a longitudinal through hole (668) exiting at a proximal end and a distal end of hydraulic force multiplier (670). Through hole (668) is dimensioned to slidably receive various other components of instrument (10), such as trocar actuator (231).

Hydraulic force multiplier (670) includes an external cylinder (672) fixed to body (652). External cylinder (672) slidably houses a proximal cap (674), a distal cap (676), a proximal piston (680), and a distal piston (682). Proximal cap (674) and distal cap (676) include cap seals (675, 677) respectively. Cap seals (675, 677) are interposed between an external portion of caps (674, 676) and an internal portion of external cylinder (672). Cap seals (675, 677) provide a fluid-tight pressure seal between the internal sidewall of external cylinder (672) and caps (674, 676) while allowing caps (674, 676) to translate relative to cylinder (672).

Pistons (680, 682) each include piston seals (686, 688), respectively. Piston seals (686, 688) are disposed within an internal sidewall of caps (674, 676). Piston seals (686, 688) provide a fluid-tight pressure seal between internal sidewalls of caps (674, 676). Pistons (680, 682) are connected to each other such that pistons (680, 682) translate together within external cylinder (672). Proximal piston (680) includes a proximal face (694) that is housed within the confines of cap (674). Proximal face (694) and cap (674) together define an input hydraulic fluid chamber (690). Distal piston (682) include a distal face (696) that is housed within the confines of cap (676). Distal face (696) and cap (676) together define an output hydraulic fluid chamber (692). Output hydraulic fluid chamber (692) and input hydraulic fluid chamber (690) may be filled with any suitable hydraulic fluid as would be apparent to one having ordinary skill in the art in view of the teachings herein.

It should be noted that the surface area of distal face (696) is dimensioned smaller than the surface areas of proximal face (694); while the surface area of the proximal end of piston (680) is larger than the surface are of the distal end of piston (682). These differences may provide for a force multiplier from the trigger carriage (662) to the driver actuator (666). In particular, when the operator pivots the trigger to provide a distally presented force on trigger carriage (662), the distally presented force is transferred to proximal cap (674). Proximal cap (674) then exerts a pressure onto input hydraulic fluid chamber (690) which in turn drives both pistons (680, 682) forward. Distal piston (682) exerts a pressure on output hydraulic chamber (692), which in turn actuates distal cap (676), which in turn applies a multiplied force onto driver actuator (666).

III. Exemplary Alternative Anvil

Figure 30C:
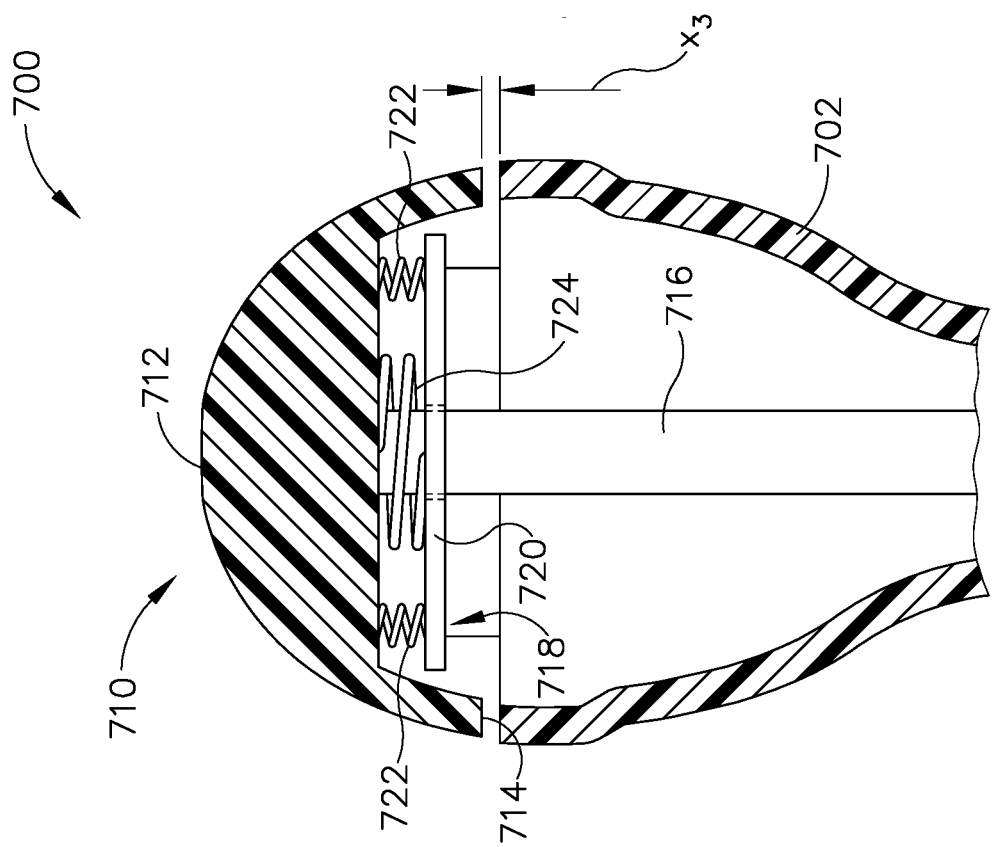
FIG. 30C depicts a cross-sectional front view of the anvil of FIG. 29 coupled with the alternative staple head assembly of FIG. 20A, where the staple head assembly has fired a plurality of staples against a proximal surface of the anvil such that the staples are formed, the tissue is severed, and the knife is actuated further distally.

FIGS. 29-30C show an exemplary alternative staple head assembly (700) and exemplary alternative anvil (710) that may be readily incorporated into instrument (10) described above. Staple head assembly (700) is substantially similar to staple head assembly (200) described above. Therefore, if not explicitly shown or described, staple head assembly (700) may include various features and functionality of staple head assembly (200) described above. Additionally, anvil (710) is substantially similar to anvil (40) described above, with differences elaborated below. Therefore, if not explicitly shown or described, anvil (710) may include various features and functionality of anvil (40) described above.

Anvil (710) includes an anvil head (712) defining an annular recess (718), a proximal surface (714), and a proximal shaft (716); which are substantially similar to anvil head (48) defining annular recess (56), proximal surface (50), and proximal shaft (44) described above, respectively, with differences elaborated below. Therefore, proximal surface (714) may define a plurality of staple forming pockets configured to suitably deform staples (66) in accordance with the description above; while proximal shaft (716) may be configured to selectively couple with a trocar in order to actuate anvil (710) relative to staple head assembly (700) in order to define a suitable gap distance d. Additionally, anvil (710) includes a translating cutting board (720) housed within annular recess (718). As will be described in greater detail below, cutting board (720) is configured to actuate within annular recess (718) during exemplary firing of staple head assembly (700) in order to help reduce the amount of force required to suitably sever and staple tissue captured between anvil (710) and staple head assembly (700) in accordance with the description above.

Cutting board (720) is coupled to anvil head (712) via a first spring (722). A second spring (724) is housed between cutting board (720) and anvil head (712). However, second spring (724) is shorter than first spring (722) such that second spring (724) does not come into contact with cutting board (720) while cutting board (720) is in the initial at rest position. The spring constant of second spring (724) is greater than the spring constant of first spring (722).

FIG. 30A shows anvil (710) coupled with staple head assembly (700) during the firing process where staples (66) are initially forming. At this moment, cutting board (720) is actuated within annular recess (718) such that first spring (722) is compressed. Movement of cutting board (720) due to compression of first spring (722) may allow for staples (66) to initially form by staple driver (250) actuating staples (66) against proximal surface (714) without knife (240) severing tissue. This may help even out the load profile of staple driver (250) and knife (240).

Figure 30B:
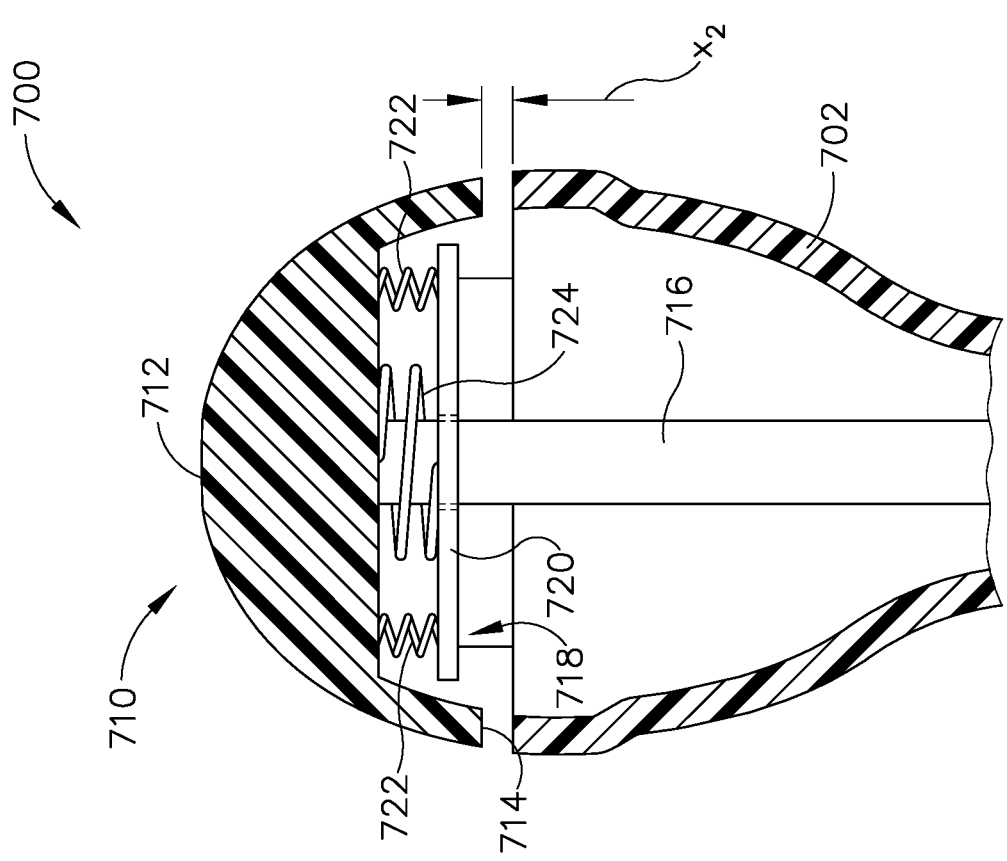
FIG. 30B depicts a cross-sectional front view of the anvil of FIG. 29 coupled with the alternative staple head assembly of FIG. 20A, where the staple head assembly has fired a plurality of staples against a proximal surface of the anvil such that the staples are formed, and the tissue is severed.

FIG. 30B shows anvil (710) coupled with staple head assembly (700) during the firing process where staple (66) are formed and cutting is complete. At this moment, cutting board (720) is actuated within annular recess (718) such that cutting board (720) engages and compresses second spring (724). FIG. 30C shows anvil coupled with staple head assembly (700) during the firing process where knife (240) is further actuated distally. At the moment in FIG. 30C, both springs (722, 724) are fully compressed. This allows for knife (240) to perform an "overstroke" to make sure tissue is sufficiently severed.

Allowing cutting board (720) to actuate during the firing stroke may allow for staples (66) to form, then for tissue to be severed subsequently, which may in turn even out the load profile. This may reduce the amount of input force required to sufficiently staple and sever tissue.

IV. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body assembly comprising: (i) a handle portion, and (ii) a shaft portion extending distally from the handle portion; (b) an end effector comprising: (i) a staple deck fixed relative to the shaft portion, (ii) a trocar, wherein the trocar is operable to actuate relative to the staple deck, and (iii) a staple driver, wherein the staple driver is operable to actuate relative to the staple deck a distance between an unfired position and a fired position; (c) an anvil operable to selectively attach to the trocar, wherein the trocar is operable to actuate the anvil relative to the staple deck to define a gap distance; and (d) a firing assembly comprising: (i) a trigger pivotably coupled with the body assembly via a first pivot, (ii) a driver actuator configured to actuate the staple driver the distance between the unfired position and the fired position, and (iii) a linkage assembly pivotably coupled with the trigger and the driver actuator, wherein the linkage assembly is pivotably coupled with the trigger via a second pivot, wherein the second pivot is proximal relative to the first pivot, wherein the linkage assembly is configured to drive the driver actuator along a path in response to the trigger pivoting about the first pivot.

Example 2

The apparatus of Example 1, wherein the linkage assembly comprise a driving link, wherein the driving link is pivotably coupled with the trigger via the second pivot.

Example 3

The apparatus of Example 2, wherein the driving link is pivotably coupled with the driver actuator.

Example 4

The apparatus of Example 3, wherein the driving link defines an elongated slot, wherein the driver actuator comprises a projection slidably housed within the elongated slot.

Example 5

The apparatus of Example 4, wherein the linkage assembly is pivotably coupled with the driver actuator via the projection and the elongated slot.

Example 6

The apparatus of any one or more of Examples 1 through 5, wherein the path the linkage assembly is configured to drive the driver actuator along corresponds with a first portion of the distance between the unfired position and the fired position.

Example 7

The apparatus of Example 6, wherein the trigger is configured to drive the driver actuator between a second portion of the distance between the unfired position and the fired position.

Example 8

The apparatus of Example 7, wherein the second portion is proximal relative to the first portion.

Example 9

The apparatus of any one or more of Examples 7 through 8, wherein the trigger is coupled with the driver actuator via a pin and a slot relationship, wherein the trigger is configured to drive the driver actuator along the second position of the distance between the unfired position and the fired position via the pin and slot relationship.

Example 10

The apparatus of any one or more of Examples 1 through 9, wherein the linkage assembly comprises a first link and a second link, wherein the first link is pivotably coupled with the trigger via the second pivot, wherein the second link is pivotably coupled with the driver actuator, wherein the first link and the second link are pivotably coupled via an intermediate pivot.

Example 11

The apparatus of Example 10, wherein the linkage assembly comprises a third link pivotably coupled to the body assembly, wherein the third link is also pivotably coupled to the first link and the second link via the intermediate pivot.

Example 12

The apparatus of Example 11, wherein the linkage assembly comprises a constraining body fixed relative to the body assembly, wherein the constraining body is configured to guide the first link as the linkage assembly drives the driver actuator along the path.

Example 13

The apparatus of any one or more of Examples 10 through 12, wherein the driver actuator defines a channel, wherein the second link is pivotably coupled with the driver actuator within the channel.

Example 14

The apparatus of Example 13, wherein the second link comprises a pin housed within the channel.

Example 15

The apparatus of any one or more of Examples 1 through 14, wherein the end effector further comprises a cylindraceous knife configured to actuate with the staple driver between the unfired position and the fired position.

Example 16

The apparatus of any one or more of Examples 1 through 15, further comprising a lockout feature, wherein the lockout feature is configured to prevent the trigger form pivoting toward the body until the gap distance is within a predetermined range.

Example 17

The apparatus of any one or more of Examples 1 through 16, further comprising an adjustment knob rotationally disposed on a proximal end of the handle portion, wherein the adjustment knob is configured to actuate the trocar relative to the staple deck.

Example 18

An apparatus, comprising: (a) a body assembly comprising: (i) a handle portion, and (ii) a shaft portion extending distally from the handle portion; (b) an end effector comprising: (i) a staple deck fixed relative to the shaft portion, (ii) a trocar, wherein the trocar is operable to actuate relative to the staple deck, and (iii) a staple driver, wherein the staple driver is operable to actuate relative to the staple deck a distance between an unfired position and a fired position; (c) an anvil operable to selectively attach to the trocar, wherein the trocar is operable to actuate the anvil relative to the staple deck to define a gap distance; and (d) a firing assembly comprising: (i) a carriage coupled to the staple driver, (ii) a trigger pivotably coupled with the body assembly, wherein the trigger is configured to pivot between an open position, a first closed position, and a second closed position, wherein the trigger is configured drive the carriage and the staple driver from the unfired position to an intermediate position in response to the trigger pivoting between the open position and the first closed position, and (iii) a driving link rotatably coupled with the carriage and the trigger, wherein the driving link is configured to drive the carriage and the staple driver from the intermediate position to the first position in response to the trigger pivoting between the first closed position and the second closed position. the driver actuator and the staple driver.

Example 19

The apparatus of Example 18, wherein the driving link defines a channel, wherein the carriage comprises a projection, wherein the projection is slidably housed within the channel.

Example 20

An apparatus, comprising: (a) a body assembly comprising: (i) a handle portion, and (ii) a shaft portion extending distally from the handle portion; (b) an end effector comprising: (i) a staple deck fixed relative to the shaft portion, (ii) a trocar, wherein the trocar is operable to actuate relative to the staple deck, and (iii) a staple driver, wherein the staple driver is operable to actuate relative to the staple deck a distance between an unfired position and a fired position; (c) an anvil operable to selectively attach to the trocar, wherein the trocar is operable to actuate the anvil relative to the staple deck to define a gap distance; and (d) a firing assembly comprising: (i) a trigger pivotably coupled with the body assembly, (ii) a driver actuator configured to actuate the staple driver the distance between the unfired position and the fired position, and (iii) a linkage assembly comprising an input link, an actuating link, and a guide link all coupled at an intermediary pivot, wherein the guide link is coupled with the body assembly, wherein the actuating link is coupled with the driver actuator, and wherein the input link is coupled with the trigger, wherein the linkage assembly is configured to actuate the driver actuator and the staple driver the distance between the unfired position and the fired position in response to the trigger pivoting toward the body assembly.

V. Miscellaneous

Any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pat. No. 9,572,573, entitled "Trans-Oral Circular Anvil Introduction System with Dilation Feature," issued Feb. 21, 2017, the disclosure of which is incorporated by reference herein; U.S. Pat. No. 9,289,207, entitled "Surgical Staple with Integral Pledget for Tip Deflection," issued Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pat. No. 9,498,222, entitled "Pivoting Anvil for Surgical Circular Stapler," issued Nov. 22, 2016, the disclosure of which is incorporated by reference herein; U.S. Pat. No. 9,724,100, entitled "Circular Anvil Introduction System with Alignment Feature," issued Aug. 8, 2017, the disclosure of which is incorporated by reference herein; U.S. Pat. No. 9,532,783, entitled "Circular Stapler with Selectable Motorized and Manual Control, Including a Control Ring," issued Jan. 3, 2017, the disclosure of which is incorporated by reference herein; U.S. Pat. No. 9,597,081, entitled "Motor Driven Rotary Input Circular Stapler with Modular End Effector," issued Mar. 21, 2017, the disclosure of which is incorporated by reference herein; and/or U.S. Pat. No. 9,463,022, entitled "Motor Driven Rotary Input Circular Stapler with Lockable Flexible Shaft," issued Oct. 11, 2016, the disclosure of which is incorporated by reference herein. Various suitable ways in which such teachings may be combined will be apparent to those of ordinary skill in the art.

Further, any one or more of the teachings, expressions, embodiments, examples, etc. described herein may be combined with any one or more of the teachings, expressions, embodiments, examples, etc. described in U.S. application Ser. No. 16/159,848, entitled "Latch to Prevent Back-Driving of Circular Surgical Stapler," filed on Oct. 15, 2018, issued as U.S. Pat. No. 11,051,819 on Jul. 6, 2021; U.S, application Ser. No. 16/159,851,entitled "Dual Stage Closure System for Circular Surgical Stapler," filed on Oct. 15, 2018, published as U.S. Pub No. 2020/0116566 0n Apr. 16, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body assembly comprising:
      (i) a handle portion, and
      (ii) a shaft portion extending distally from the handle portion;
   (b) an end effector comprising:
      (i) a staple deck fixed relative to the shaft portion,
      (ii) an elongated coupling element, wherein the elongated coupling element is operable to actuate relative to the staple deck, and
      (iii) a staple driver, wherein the staple driver is operable to actuate relative to the staple deck and the elongated coupling element a distance between an unfired position and a fired position;
   (c) an anvil operable to selectively attach to the elongated coupling element, wherein the elongated coupling element is operable to actuate the anvil relative to the staple deck to define a gap distance to thereby capture tissue between the anvil and the staple deck; and
   (d) a firing assembly comprising:
      (i) a trigger pivotably coupled with the body assembly via a first pivot,
      (ii) a driver actuator configured to actuate the staple driver the distance between the unfired position and the fired position, wherein the driver actuator is slidably contained within the body assembly, wherein a proximal portion of the driver actuator defines an elongated channel, and
      (iii) a linkage assembly pivotably coupled with the trigger and the driver actuator, wherein the linkage assembly is pivotably coupled with the driver actuator via a pin housed within the elongated channel, wherein the linkage assembly is pivotably coupled with the trigger via a second pivot, wherein the second pivot is proximal relative to the first pivot, wherein the linkage assembly is configured to drive the driver actuator along a path in response to the trigger pivoting about the first pivot.

2. The apparatus of claim 1, wherein the linkage assembly comprise a driving link, wherein the driving link is pivotably coupled with the trigger via the second pivot.

3. The apparatus of claim 2, wherein the driving link is pivotably coupled with the driver actuator.

4. The apparatus of claim 3, wherein the driving link defines an elongated slot, wherein the driver actuator comprises a projection slidably housed within the elongated slot.

5. The apparatus of claim 4, wherein the linkage assembly is pivotably coupled with the driver actuator via the projection and the elongated slot.

6. The apparatus of claim 1, wherein the path the linkage assembly is configured to drive the driver actuator along corresponds with a first portion of the distance between the unfired position and the fired position.

7. The apparatus of claim 6, wherein the trigger is configured to drive the driver actuator between a second portion of the distance between the unfired position and the fired position.

8. The apparatus of claim 7, wherein the second portion is proximal relative to the first portion.

9. The apparatus of claim 7, wherein the trigger is coupled with the driver actuator via a pin and a slot relationship, wherein the trigger is configured to drive the driver actuator along the second portion of the distance between the unfired position and the fired position via the pin and slot relationship.

10. The apparatus of claim 1, wherein the linkage assembly comprises a first link and a second link, wherein the first link is pivotably coupled with the trigger via the second pivot, wherein the second link is pivotably coupled with the driver actuator, wherein the first link and the second link are pivotably coupled via an intermediate pivot.

11. The apparatus of claim 10, wherein the linkage assembly comprises a third link pivotably coupled to the body assembly, wherein the third link is also pivotably coupled to the first link and the second link via the intermediate pivot.

12. The apparatus of claim 11, wherein the linkage assembly comprises a constraining body fixed relative to the body assembly, wherein the constraining body is configured to guide the first link as the linkage assembly drives the driver actuator along the path.

13. The apparatus of claim 10, wherein the second link is pivotably coupled with the driver actuator within the elongated channel.

14. The apparatus of claim 13, wherein the second link comprises the pin housed within the elongated channel.

15. The apparatus of claim 1, wherein the end effector further comprises a cylindraceous knife configured to actuate with the staple driver between the unfired position and the fired position.

16. The apparatus of claim 1, further comprising a lockout feature, wherein the lockout feature is configured to prevent the trigger from pivoting toward the body assembly until the gap distance is within a predetermined range.

17. The apparatus of claim 1, further comprising an adjustment knob rotationally disposed on a proximal end of the handle portion, wherein the adjustment knob is configured to actuate the elongated coupling element relative to the staple deck.

18. An apparatus, comprising:
(a) a body assembly comprising:
  (i) a handle portion, and
  (ii) a shaft portion extending distally from the handle portion;
(b) an end effector comprising:
  (i) a staple deck fixed relative to the shaft portion,
  (ii) an elongated coupling element, wherein the elongated coupling element is operable to actuate relative to the staple deck, and
  (iii) a staple driver, wherein the staple driver is operable to actuate relative to the staple deck a distance between an unfired position and a fired position;
(c) an anvil operable to selectively attach to the elongated coupling element, wherein the elongated coupling element is operable to actuate the anvil relative to the staple deck to define a gap distance; and
(d) a firing assembly comprising:
  (i) a trigger pivotably coupled with the body assembly,
  (ii) a driver actuator configured to actuate the staple driver the distance between the unfired position and the fired position, wherein the driver actuator comprises a proximal carriage defining a slot, wherein the proximal carriage is configured to actuate relative to the body assembly, and
  (iii) a linkage assembly comprising an input link, an actuating link, and a guide link all coupled at an intermediary pivot, wherein the guide link is coupled with the body assembly, wherein the actuating link is coupled with the driver actuator via a pin slidably contained within the slot of the proximal carriage, and wherein the input link is coupled with the trigger, wherein the linkage assembly is configured to actuate the driver actuator and the staple driver the distance between the unfired position and the fired position in response to the trigger pivoting toward the body assembly.

19. An apparatus, comprising:
(a) a body assembly comprising:
  (i) a handle portion, and
  (ii) a shaft portion extending distally from the handle portion;
(b) an end effector comprising:
  (i) a staple deck fixed relative to the shaft portion,
  (ii) an elongated coupling element, wherein the elongated coupling element is operable to actuate relative to the staple deck, and
  (iii) a staple driver, wherein the staple driver is operable to actuate relative to the staple deck and the elongated coupling element a distance between an unfired position and a fired position;
(c) an anvil operable to selectively attach to the elongated coupling element, wherein the elongated coupling element is operable to actuate the anvil relative to the staple deck to define a gap distance to thereby capture tissue between the anvil and the staple deck; and
(d) a firing assembly comprising:
  (i) a trigger pivotably coupled with the body assembly via a first pivot,
  (ii) a driver actuator coupled to a proximal portion of the staple driver and defining a slot, wherein the driver actuator is configured to actuate the staple driver the distance between the unfired position and the fired position, and
  (iii) a linkage assembly pivotably coupled with the trigger and the driver actuator, wherein the linkage assembly comprises an input link and a driving link pivotally coupled together, wherein the input link is pivotally coupled with the trigger, wherein the driving link is directly pivotally attached to the driver actuator via a pin housed within the slot of the driver actuator, wherein the linkage assembly is configured to drive the driver actuator along a path in response to the trigger pivoting about the first pivot.

* * * * *